US011008593B2

(12) United States Patent
Hellingwerf et al.

(10) Patent No.: US 11,008,593 B2
(45) Date of Patent: May 18, 2021

(54) PROCESS FOR PRODUCING 1,3-PROPANEDIOL COMPOUND

(71) Applicant: Photanol B.V., Amsterdam (NL)

(72) Inventors: Klaas Jan Hellingwerf, Amsterdam (NL); Maarten Joost Teixeira De Mattos, Amsterdam (NL)

(73) Assignee: Photanol, B.V.

( * ) Notice: Subject to any disclaimer, the term of this patent is extended or adjusted under 35 U.S.C. 154(b) by 45 days.

(21) Appl. No.: 16/195,566

(22) Filed: Nov. 19, 2018

(65) Prior Publication Data

US 2019/0177752 A1 Jun. 13, 2019

Related U.S. Application Data

(60) Continuation of application No. 14/956,470, filed on Dec. 2, 2015, now Pat. No. 10,131,924, which is a division of application No. 12/808,480, filed as application No. PCT/NL2008/050804 on Dec. 17, 2008, now Pat. No. 9,228,210.

(60) Provisional application No. 61/014,092, filed on Dec. 17, 2007.

(30) Foreign Application Priority Data

Dec. 17, 2007 (EP) ..................... 07123340

(51) Int. Cl.
C12P 7/56 (2006.01)
C12N 1/20 (2006.01)
C12N 15/74 (2006.01)
C12P 5/02 (2006.01)
C12P 7/04 (2006.01)
C12P 7/06 (2006.01)
C12P 7/16 (2006.01)
C12P 7/18 (2006.01)
C12P 7/20 (2006.01)
C12P 7/24 (2006.01)
C12P 7/28 (2006.01)
C12N 15/82 (2006.01)
C12P 7/30 (2006.01)

(52) U.S. Cl.
CPC ............... C12P 7/56 (2013.01); C12N 1/20 (2013.01); C12N 15/74 (2013.01); C12N 15/82 (2013.01); C12P 5/026 (2013.01); C12P 7/04 (2013.01); C12P 7/06 (2013.01); C12P 7/065 (2013.01); C12P 7/16 (2013.01); C12P 7/18 (2013.01); C12P 7/20 (2013.01); C12P 7/24 (2013.01); C12P 7/28 (2013.01); C12P 7/30 (2013.01); Y02E 50/10 (2013.01)

(58) Field of Classification Search
None
See application file for complete search history.

(56) References Cited

U.S. PATENT DOCUMENTS

| 4,778,759 | A | 10/1988 | Szalay et al. |
| 6,699,696 | B2 | 3/2004 | Woods et al. |
| 7,682,821 | B2 | 3/2010 | Woods et al. |
| 8,349,587 | B2 | 1/2013 | Fischer et al. |
| 8,669,094 | B2 | 3/2014 | Anthony et al. |
| 8,735,651 | B2 | 5/2014 | Lee |
| 2007/0072279 | A1 | 3/2007 | Meynial-Salles et al. |
| 2009/0104656 | A1 | 4/2009 | Weiss et al. |

FOREIGN PATENT DOCUMENTS

| EP | 0635574 | | 1/1995 |
| EP | 1731604 | | 12/2006 |
| EP | 1932910 | A1 | 6/2008 |
| WO | 9821341 | | 5/1998 |
| WO | 9839457 | | 9/1998 |
| WO | 9914335 | | 3/1999 |
| WO | 9928480 | | 6/1999 |
| WO | 2005052168 | A2 | 6/2005 |
| WO | 2005052168 | A3 | 6/2005 |
| WO | 2005073364 | | 8/2005 |
| WO | 2007029664 | A1 | 3/2007 |
| WO | 2007041269 | | 4/2007 |
| WO | 2007084477 | | 7/2007 |
| WO | 2007130518 | | 11/2007 |
| WO | 2008137404 | | 11/2008 |

OTHER PUBLICATIONS

Hirokawa et al. (Metab. Engin., vol. 39 (2017), pp. 192-199.*
McGinn et al., (Plant Physiol., vol. 132, pp. 218-229, 2003).
Lan et al., (Metabol. Engin., vol. 13, 2011, pp. 353-363).
Oliver et al. (PNAS, vol. 110, No. 4, 2013, pp. 1249-1254).
Varman et al., Microbial Cell Factories 2013, 12:117.
Shen et al., (Energy & Environ. Sci., vol. 5, 2012, pp. 9574-9583).
Fu et al., (J. Phycol. vol. 43, pp. 485-496, 2007).
Lu (Biotech. Advances, vol. 28, 2010, pp. 742-746).
Ogawa (Plant Physiol., 1992, vol. 99, pp. 1604-1608).
Zhou et al., (Metab. Engin., vol. 14, 2012, pp. 394-400).
Hollinshead, Whitney D., et al. "Boosting d-lactate production in engineered cyanobacteria using sterilized anaerobic digestion effluents." Bioresource technology 169 (2014): 462-467.

(Continued)

Primary Examiner — Hope A Robinson
(74) Attorney, Agent, or Firm — McDonnell Boehnen Hulbert & Berghoff LLP

(57) ABSTRACT

A process of producing an organic compound and/or an intermediary compound as defined herein by feeding carbon dioxide to a culture of a cyanobacterial cell and subjecting said culture to light, wherein said cell is capable of expressing a nucleic acid molecule, wherein the expression of said nucleic acid molecule confer on the cell the ability to convert a glycolytic intermediate into said organic compound and/or into said intermediary compound and wherein said nucleic acid molecule is under the control of a regulatory system which responds to a change in the concentration of a nutrient in said culture.

12 Claims, 4 Drawing Sheets

Specification includes a Sequence Listing.

(56) References Cited

OTHER PUBLICATIONS

Stal, Lucas J., and Roy Moezelaar. "Fermentation in cyanobacteria." FEMS microbiology reviews 21.2 (1997): 179-211.

Li, Han, and James C. Liao. "Engineering a cyanobacterium as the catalyst for the photosynthetic conversion of CO 2 to 1, 2-propanediol." Microbial cell factories 12.1 (2013): 4.

Deng, Ming-De, and John R. Coleman. "Ethanol synthesis by genetic engineering in cyanobacteria." Applied and environmental microbiology 65.2 (1999): 523-528.

Singh, Sudheer K., Syed U. Ahmed, and Ashok Pandey. "Metabolic engineering approaches for lactic acid production." Process Biochemistry 41.5 (2006): 991-1000.

Ishida, Nobuhiro, et al. "D-Lactic acid production by metabolically engineered Saccharomyces cerevisiae." Journal of Bioscience and Bioengineering 101.2 (2006): 172-177.

Niederholtmeyer, Henrike, et al. "Engineering cyanobacteria to synthesize and export hydrophilic products." Applied and environmental microbiology 76.11 (2010): 3462-3466.

Zhou, Jie, et al. "Production of optically pure d-lactate from CO2 by blocking the PHB and acetate pathways and expressing d-lactate dehydrogenase in cyanobacterium *Synechocystis* sp. PCC 6803." Process Biochemistry 49.12 (2014): 2071-2077.

Li, Chao, et al. "Enhancing the light-driven production of d-lactate by engineering cyanobacterium using a combinational strategy." Scientific reports 5 (2015): 9777.

\* cited by examiner

N-sufficiency          N-depletion

Fig 6

| Product | donor strain | Cassette | Pathway |
|---|---|---|---|
| Ethanol | Sarcina ventriculi / Lactobacillus brevis | pdc adh1 | pyruvate —pdc→ acetaldehyde —adh1→ ethanol |
| Acetone | Clostridium acetobutylicum | thl ctfAB adc | Ac-CoA —thl→ acetoacylCoA —ctfAB→ Ac.acetate —adc→ acetone |
| Propanol | Clostridium acetobutylicum / Klebsiella pneumoniae | thl ctfAB adc / aad | .... acetone —aad→ propanol |
| Ethylene | Pseudomonas syringiae | efe | 2-ketoglutarate —efe→ ethylene |
| Butanol | Clostridium acetobutylicum | thl 3hbd crt etf ald bdh | ...—3hbd/crt/etf→ butyrylCoA —ald→ butyraldehyde —bdh→ butanol |
| Butanol | Lactococcus lactis / Klebsiella pneumoniae | als aldb butabutb / dhaB dhaT | pyruvate —als→ 2-acetolactate —aldb→ acetoin —butb→ 2,3 butanediol —dhaB→ 2-butanone —dhaT→ 2-butanol |
| Lactic acid | Lactococcus lactis | ldh | pyruvate —ldh→ lactic acid |
| 1,3 Propanediol | Synechocystis spec PCC 6803 / Saccharomyces cer. / Klebsiella pneumoniae | gpd1 gpp1 dha ygd | glyceraldehyde-P —gpd1→ glycerol-P —gpp1→ glycerol —dha→ OHprop.aldehyde —ygd→ 1,3 propanediol |

PROCESS FOR PRODUCING 1,3-PROPANEDIOL COMPOUND

CROSS REFERENCE TO RELATED APPLICATIONS

This application is a continuation of U.S. application Ser. No. 14/956,470 filed Dec. 2, 2015 and issuing as U.S. Pat. No. 10,131,924, which is a division of U.S. application Ser. No. 12/808,480 filed Aug. 12, 201 and issuing as U.S. Pat. No. 9,228,210, which was a national stage application under 35 U.S.C. § 371 of International Application No. PCT/NL2008/050804, filed on Dec. 17, 2008. This invention relates to and claims the benefit of priority to European Patent Application No. 07123340.7, filed on Dec. 17, 2007, and to Provisional Application No. 61/014,092, filed on Dec. 17, 2007, the disclosures of each of which are explicitly herein incorporated by reference in their entirety.

FIELD OF THE INVENTION

The invention relates to a process of producing an organic compound and/or an intermediary compound produced in the pathway leading to said organic compound by feeding carbon dioxide to a culture of a cyanobacterial cell and subjecting said culture to light, wherein said cell is capable of expressing a nucleic acid molecule wherein the expression of said nucleic acid molecule confers on said cell the ability to convert a glycolytic intermediate such as pyruvate or glyceraldehyde 3-phosphate into said organic compound and/or into said intermediary compound and wherein expression of said nucleic acid molecule is under the control of a regulatory system which responds to a change in the concentration of a nutrient in said culture. The invention further relates to a cyanobacterial cell for use in this process.

BACKGROUND OF THE INVENTION

Our economy is driven by the use of fossil fuels. Shortages caused by exhausting oil supplies primarily affect the transport sector of our society and the chemical industry, but secondarily affect all aspects of human activities. As an additional problem, the use of oil supplies has caused the build-up of a high $CO_2$ concentration in the atmosphere. Energy ultimately comes from the sun and this energy drives photosynthetic process in plants and photoautotrophic bacteria. This knowledge has led to new methods for the synthesis of biofuels. In essence, these processes employ plants and algal species to reduce $CO_2$ to the level of sugars and cell material. After harvesting, these end products are converted to ethanol by yeast fermentation (in the case of crops) or converted chemically to biofuels (in the case of algae). The overall energy conservation of these methods is highly inefficient and therefore demands large surface areas. In addition, the processes are rather labor-intensive, are demanding with respect to water consumption and affect foodstock prices with adverse consequences for food supplies. A more remotely similar process is based on the conversion of solar energy into hydrogen. Also this process suffers from a severely decreased efficiency.

Numerous biotechnological processes make use of genetically engineered organisms in order to produce bulk or fine chemicals, proteins or antibiotics. In many cases, increased production has been obtained by improved gene expression and by optimization of growth conditions. In all processes we are aware of, the initial carbon-precursor has been and still is sugar (notably glucose, but many other mono- and polysaccharides are in use) or related organic substrates: solventogenesis (including butanol and ethanol) and organic acid production (e.g. lactic-, citric- or succinic acid) always starts from glucose, which makes it inefficient as the production process uses a high energy initial compound as substrate.

U.S. Pat. No. 6,699,696 describes a process of producing ethanol by feeding carbon dioxide to a cyanobacterial cell, especially a *Synechococcus* comprising a nucleic acid molecule encoding an enzyme enabling the cell to convert pyruvate into ethanol, subjecting said cyanobacterial cell to sun energy and collecting ethanol. This system has several drawbacks among others the expression system used is temperature sensitive which demands to adapt the production system for such regulation.

Therefore, there is still a need for an alternative and even improved production process of an organic compound, which do not have all the drawbacks of existing processes.

DESCRIPTION OF THE INVENTION

The present invention relates to a scalable process for the production of an organic compound suitable as chemical feedstock or as a biofuel. The invention combines metabolic properties of photoautotrophic and chemoorganotrophic prokaryotes and is based on the employment of recombinant oxyphototrophs with high rates of conversion of Calvin cycle intermediates to a fermentative end product. Its novelty resides in the fact a) that its core chemical reactions use $CO_2$ as the sole carbon-containing precursor and light (preferably sunlight) as the sole energy source to drive $CO_2$ reduction and b) that a great variety of end products can be realized by the same principle, namely introduction of a nucleic acid molecule cassette encoding a specific fermentative pathway and c) that production is controlled by a medium component and starts at the most appropriate time, namely at the highest possible cell density. Whereas in current applications of fuel production, organisms are substrate (crops in ethanol production) or product (microalgae as biodiesel), here microorganisms are used as highly specialized catalysts for the conversion of $CO_2$ as substrate to a useful end product. These catalysts can be subjected to optimization strategies through physical- and chemical systems-biology approaches. The biochemical background of the invention is more extensively described in example 1. Each aspect of the invention is more extensively described below.

Cyanobacteria

In a first aspect, the invention provides a Cyanobacteria capable of expressing a nucleic acid molecule, wherein the expression of said nucleic acid molecule confers on the Cyanobacteria the ability to convert a glycolytic intermediate into an organic compound and/or into an intermediary compound produced in the pathway leading to said organic compound and wherein the nucleic acid molecule is under the control of a regulatory system which responds to a change in the concentration of a nutrient when culturing said Cyanobacteria.

In the context of the invention a Cyanobacterium or a cyanobacterial cell is a blue-green algae which is a photosynthetic unicellular prokaryote. Examples of Cyanobacteria include the genera *Aphanocapsa, Anabaena, Nostoc, Oscillatoria, Synechococcus, Gloeocapsa, Agmenellum, Scytonema, Mastigocladus, Arthrosprira, Haplosiphon*. A preferred genus is *Synechococcus*. A more preferred species of this genus is a *Synechocystis* species. Even more preferably, the *Synechocystis* is a Pasteur Culture Collection (PCC) 6083 *Synechocystis*, which is a publicly available strain via ATCC for example. A preferred organism used is the phototrophic *Synechocystis* PCC 6083: this is a fast growing cyanobacterium with no specific nutritional demands. Its physiological traits are well-documented: it is able to survive and grow in a wide range of conditions. For example, *Synechocystis* sp. PCC 6803 can grow in the absence of photosynthesis if a suitable fixed-carbon source such as glucose is provided. Perhaps most significantly, *Synechocystis* sp. PCC 6803 was the first photosynthetic organism for which the entire genome sequence was determined (available on http://www.kazusa.or.jp/cyano/cyano.html). In addition, an efficient gene deletion strategy (Shestakov S V et al, (2002), Photosynthesis Research, 73: 279-284 and Nakamura Y et al, (1999), Nucleic Acids Res. 27:66-68) is available for *Synechocystis* sp. PCC 6803, and this organism is furthermore easily transformable via homologous recombination (Grigirieva G A et al, (1982), FEMS Microbiol. Lett. 13: 367-370).

A Cyanobacteria as defined herein is capable of converting a glycolytic intermediate into an organic compound and/or into an intermediary compound as defined herein. A biochemical background of the Cyanobacteria of the invention is given in Example 1.

A Cyanobacteria as defined herein preferably comprises a nucleic acid molecule encoding an enzyme capable of converting a glycolytic intermediate into an organic compound and/or into an intermediary compound as defined herein. An organic compound is herein preferably defined as being a compound being more reduced than $CO_2$. A Cyanobacteria is therefore capable of expressing a nucleic acid molecule as defined herein, whereby the expression of a nucleic acid molecule as defined herein confers on the Cyanobacteria the ability to convert a glycolytic intermediate into an organic compound and/or into an intermediary compound all as defined herein. A glycolytic intermediate may be dihydroxyacetone-phosphate, glyceraldehyde-3-phosphate, 1,3-bis-phosphoglycerate, 2-phosphoglycerate, 3-phosphoglycerate, phospho-enol-pyruvate and pyruvate. Preferred glycolytic intermediates are pyruvate and glyceraldehyde-3-phosphate. The skilled person knows that the identity of the glycolytic intermediate converted into an organic product to be produced depends on the identity of the organic product to be produced.

Preferred organic products are selected from: a C1, C2, C3, C4, C5, or C6 alkanol, alkanediol, alkanone, alkene, or organic acid. Preferred alkanols are C2, C3 or C4 alkanols. More preferred are ethanol, propanol, butanol. A preferred alkanediol is 1,3-propanediol. A preferred alkanone is acetone. A preferred organic acid is D-lactate. A preferred alkene is ethylene.

A preferred glycolytic intermediate for the production of ethanol, propanol, butanol, acetone or D-lactate is pyruvate. A preferred glycolytic intermediate for the production of 1,3-propanediol is glyceraldehyde-3-phosphate. A preferred glycolytic intermediate for the production of ethylene is alpha-oxoglutarate "Converting a glycolytic intermediate into an organic compound" preferably means that detectable amounts of an organic compound are detected in the culture of a Cyanobacteria as defined herein cultured in the presence of light and dissolved carbon dioxide and/or bicarbonate ions during at least 1 day using a suitable assay for the organic compound. A preferred concentration of said dissolved carbon dioxide and/or bicarbonate ions is at least the natural occurring concentration at neutral to alkaline conditions (pH 7 to 8) being approximately 1 mM. A more preferred concentration of carbon dioxide and/or bicarbonate ions is higher than this natural occurring concentration. A preferred method to increase the carbon dioxide and/or bicarbonate ions in solution is by enrichment with waste carbon dioxide from industrial plants. The concentration of carbon dioxide in the gas that is sparged into the culture broth may be increased from the equivalent of 0.03% (air) up to 0.2%.

In another preferred embodiment, a Cyanobacterium converts a glycolytic intermediate into an intermediary component of the pathway leading to a given organic compound. In this embodiment, detectable amounts of an intermediary compound are detected in a Cyanobacterium and/or in its culture, wherein said Cyanobacterium is cultured in the presence of sunlight and carbon dioxide during at least 1 day using a given assay for the intermediary compound. Depending on the identity of the organic compound, the skilled person will know which intermediary compound may be produced.

All organic compounds or intermediary compounds produced are produced within the cell and may spontaneously diffuse into the culture broth. A preferred assay for said intermediates and alkanols, alkanones, alkanediols and organic acids is High Performance Liquid Chromatography (HPLC). A detectable amount for said intermediates and alkanols, alkanones, alkanediols and organic acids is preferably at least 0.1 mM under said culture conditions and using said assay. Preferably, a detectable amount is at least 0.2 mM, 0.3 mM, 0.4 mM, or at least 0.5 mM.

Ethanol as Organic Compound

When an organic product to be produced is ethanol, preferred nucleic acid molecules code for enzymes capable of converting pyruvate into ethanol and/or into an intermediary compound produced in the pathway leading to ethanol, said enzymes comprise a pyruvate decarboxylase (pdc) and an alcohol dehydrogenase (adh). The intermediary compound is acetaldehyde. A preferred assay for acetaldehyde is HPLC. A detectable amount of acetaldehyde is preferably at least 0.1 mM under said culture conditions as defined earlier herein and using said assay. Therefore in this preferred embodiment, a Cyanobacterium comprises a nucleic acid molecule encoding a pdc and another one encoding an adh. Accordingly, this preferred embodiment relates to a Cyanobacterium capable of expressing the following nucleic acid molecules being represented by nucleotide sequences, wherein the expression of these nucleotide sequences confers on the cell the ability to convert pyruvate into acetaldehyde and/or into ethanol:

(a) a nucleotide sequence encoding a pdc, wherein said nucleotide sequence is selected from the group consisting of:
  i. nucleotide sequences encoding a pdc, said pdc comprising an amino acid sequence that has at least 40% sequence identity with the amino acid sequence of SEQ ID NO:1.
  ii. nucleotide sequences comprising a nucleotide sequence that has at least 40% sequence identity with the nucleotide sequence of SEQ ID NO:2.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code and
(b) a nucleotide sequence encoding an adh, wherein said nucleotide sequence is selected from the group consisting of:

i. nucleotide sequences encoding an adh, said adh comprising an amino acid sequence that has at least 40% sequence identity with the amino acid sequence of SEQ ID NO:3.
ii. nucleotide sequences comprising a nucleotide sequence that has at least 40% sequence identity with the nucleotide sequence of SEQ ID NO:4.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code.

Propanol as Organic Compound

When an organic product to be produced is propanol, the preferred nucleic acid molecules code for enzymes capable of converting pyruvate into propanol and/or into an intermediary compound produced in the pathway leading to propanol, said enzymes comprise a thiolase, an acetoacetyl-CoA transferase, an acetoacetate decarboxylase and a propanol dehydrogenase. The intermediary compound is acetone. A preferred assay for acetone is HPLC. A detectable amount of acetone is preferably at least 0.1 mM under said culture conditions as defined earlier herein and using said assay. Therefore in this preferred embodiment, a Cyanobacterium comprises a nucleic acid molecule encoding a thiolase, an acetoacetylCoA transferase, an acetoacetate decarboxylase and another one encoding a propanol dehydrogenase. Accordingly, this preferred embodiment relates to a Cyanobacterium capable of expressing the following nucleic acid molecules being represented by nucleotide sequences, wherein the expression of these nucleotide sequences confers on the cell the ability to convert pyruvate into acetone and/or into propanol:

(a) a nucleotide sequence encoding a thiolase, wherein said nucleotide sequence is selected from the group consisting of:
i. nucleotide sequences encoding a thiolase, said thiolase comprising an amino acid sequence that has at least 40% sequence identity with the amino acid sequence of SEQ ID NO:5.
ii. nucleotide sequences comprising a nucleotide sequence that has at least 40% sequence identity with the nucleotide sequence of SEQ ID NO:6.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code, (b) a nucleotide sequence encoding an acetoacetylCoA transferase, wherein said nucleotide sequence is selected from the group consisting of:
i. nucleotide sequences encoding an acetoacetylCoA transferase, said acetoacetylCoA transferase comprising an amino acid sequence that has at least 40% sequence identity with the amino acid sequence of SEQ ID NO:95 and another one having the same sequence identity with SEQ ID NO: 96.
ii. nucleotide sequences comprising a nucleotide sequence that has at least 40% sequence identity with the nucleotide sequence of SEQ ID NO:97 and another one having the same sequence identity with SEQ ID NO: 98.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code, (c) a nucleotide sequence encoding an acetoacetylCoA decarboxylase, wherein said nucleotide sequence is selected from the group consisting of:
i. nucleotide sequences encoding an acetoacetylCoA decarboxylase, said acetoacetylCoA decarboxylase comprising an amino acid sequence that has at least 40% sequence identity with the amino acid sequence of SEQ ID NO:7.
ii. nucleotide sequences comprising a nucleotide sequence that has at least 40% sequence identity with the nucleotide sequence of SEQ ID NO:8.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code and (d) a nucleotide sequence encoding a propanol dehydrogenase, wherein said nucleotide sequence is selected from the group consisting of:
i. nucleotide sequences encoding a propanol dehydrogenase, said propanol dehydrogenase comprising an amino acid sequence that has at least 40% sequence identity with the amino acid sequence of SEQ ID NO:9.
ii. nucleotide sequences comprising a nucleotide sequence that has at least 40% sequence identity with the nucleotide sequence of SEQ ID NO:10.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code.

A preferred acetoacetylCoA transferase is formed by two subunits: one is represented by SEQ ID NO:95, the other one by SEQ ID NO:96. Corresponding encoding nucleotide sequences are preferably represented by SEQ ID NO: 97, 98 respectively.

Butanol as Organic Product

Butanol is a preferred organic product. The invention encompasses at least two pathways for producing butanol.

In a first pathway, when an organic product to be produced is butanol, preferred nucleic acid molecules code for enzymes capable of converting pyruvate into butanol and/or into an intermediary compound produced in the pathway leading to butanol, said enzymes comprise a thiolase, a hydroxybutyrylCoA dehydrogenase, a crotonase, a butyryl-CoA dehydrogenase, a butyraldehyde dehydrogenase and a butanol dehydrogenase. A preferred intermediary compound is butyraldehyde. A preferred assay for butyraldehyde is HPLC. A detectable amount of butyraldehyde is at least 0.1 mM under said culture conditions as defined earlier herein and using said assay. Therefore in this preferred embodiment, a Cyanobacterium comprises a nucleic acid molecule encoding a thiolase, a hydroxybutyrylCoA dehydrogenase, a crotonase, a butyryl-CoA dehydrogenase, a butyraldehyde dehydrogenase and a butanol dehydrogenase. Accordingly, this preferred embodiment relates to a Cyanobacterium capable of expressing the following nucleotide molecules being represented by nucleotide sequences, wherein the expression of these nucleotide sequences confers on the cell the ability to convert pyruvate into butyraldehyde and/or into butanol:

(a) a nucleotide sequence encoding a thiolase, wherein said nucleotide sequence is selected from the group consisting of:
  i. nucleotide sequences encoding a thiolase, said thiolase comprising an amino acid sequence that has at least 40% sequence identity with the amino acid sequence of SEQ ID NO:11.
  ii. nucleotide sequences comprising a nucleotide sequence that has at least 40% sequence identity with the nucleotide sequence of SEQ ID NO:12.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code,
(b) a nucleotide sequence encoding a hydroxybutyrylCoA dehydrogenase, wherein said nucleotide sequence is selected from the group consisting of:
  i. nucleotide sequences encoding an hydroxybutyrylCoA dehydrogenase, said hydroxybutyrylCoA dehydrogenase comprising an amino acid sequence that has at least 40% sequence identity with the amino acid sequence of SEQ ID NO:13.
  ii. nucleotide sequences comprising a nucleotide sequence that has at least 40% sequence identity with the nucleotide sequence of SEQ ID NO:14.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code,
(c) a nucleotide sequence encoding a crotonase, wherein said nucleotide sequence is selected from the group consisting of:
  i. nucleotide sequences encoding a crotonase, said crotonase comprising an amino acid sequence that has at least 40% sequence identity with the amino acid sequence of SEQ ID NO:15.
  ii. nucleotide sequences comprising a nucleotide sequence that has at least 40% sequence identity with the nucleotide sequence of SEQ ID NO:16.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code,
(d) a nucleotide sequence encoding a butyryl-CoA dehydrogenase, wherein said nucleotide sequence is selected from the group consisting of:
  i. nucleotide sequences encoding a butyryl-CoA dehydrogenase, said butyryl-CoA dehydrogenase comprising an amino acid sequence that has at least 40% sequence identity with the amino acid sequence of SEQ ID NO:17.
  ii. nucleotide sequences comprising a nucleotide sequence that has at least 40% sequence identity with the nucleotide sequence of SEQ ID NO:18.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code,
(e) a nucleotide sequence encoding an butyraldehyde dehydrogenase, wherein said nucleotide sequence is selected from the group consisting of:
  i. nucleotide sequences encoding a butyraldehyde dehydrogenase, said butyraldehyde dehydrogenase comprising an amino acid sequence that has at least 40% sequence identity with the amino acid sequence of SEQ ID NO:19.
  ii. nucleotide sequences comprising a nucleotide sequence that has at least 40% sequence identity with the nucleotide sequence of SEQ ID NO:20.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code and
(f) a nucleotide sequence encoding an butanol dehydrogenase, wherein said nucleotide sequence is selected from the group consisting of:
  i. nucleotide sequences encoding a butanol dehydrogenase, said butanol dehydrogenase comprising an amino acid sequence that has at least 40% sequence identity with the amino acid sequence of SEQ ID NO:21.
  ii. nucleotide sequences comprising a nucleotide sequence that has at least 40% sequence identity with the nucleotide sequence of SEQ ID NO:22.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code.

In a second pathway, when an organic product to be produced is butanol, preferred nucleic acid molecules code for enzymes capable of converting pyruvate into butanol and/or into an intermediary compound produced in the pathway leading to butanol, said enzymes comprise a 2-acetolactate synthetase, an acetolactate decarboxylase, a diacetyl reductase, an acetoin reductase, a glycerol dehydratase (a large, medium and small subunits thereof), a 1,3-propanediol dehydrogenase.

A preferred intermediary compound is 2,3-butanediol. A preferred assay for 2,3-butanediol is HPLC. A detectable amount of 2,3-butanediol is at least 0.1 mM under said culture conditions as defined earlier herein and using said assay. Therefore in this preferred embodiment, a Cyanobacterium comprises a nucleic acid molecule encoding a 2-acetolactate synthetase, an acetolactate decarboxylase, a diacetyl reductase, an acetoin reductase, a glycerol dehydratase (a large, medium and small subunits thereof), a 1,3-propanediol dehydrogenase.

Accordingly, this preferred embodiment relates to a Cyanobacterium capable of expressing the following nucleotide molecules being represented by nucleotide sequences, wherein the expression of these nucleotide sequences confers on the cell the ability to convert pyruvate into 2,3-butanediol and/or into butanol:
  (a) a nucleotide sequence encoding a 2-acetolactate synthetase, wherein said nucleotide sequence is selected from the group consisting of:
    i. nucleotide sequences encoding a 2-acetolactate synthetase, said 2-acetolactate synthetase e comprising an amino acid sequence that has at least 40% sequence identity with the amino acid sequence of SEQ ID NO:75.

ii. nucleotide sequences comprising a nucleotide sequence that has at least 40% sequence identity with the nucleotide sequence of SEQ ID NO:76.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code, (b) a nucleotide sequence encoding an acetolactate decarboxylase, wherein said nucleotide sequence is selected from the group consisting of:
i. nucleotide sequences encoding an acetolactate decarboxylase, said acetolactate decarboxylase comprising an amino acid sequence that has at least 40% sequence identity with the amino acid sequence of SEQ ID NO:77.
ii. nucleotide sequences comprising a nucleotide sequence that has at least 40% sequence identity with the nucleotide sequence of SEQ ID NO:78.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code, (c) a nucleotide sequence encoding a diacetyl reductase, wherein said nucleotide sequence is selected from the group consisting of:
i. nucleotide sequences encoding a diacetyl reductase, said diacetyl reductase comprising an amino acid sequence that has at least 40% sequence identity with the amino acid sequence of SEQ ID NO:79
ii. nucleotide sequences comprising a nucleotide sequence that has at least 40% sequence identity with the nucleotide sequence of SEQ ID NO:80
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code, (d) a nucleotide sequence encoding an acetoin reductase, wherein said nucleotide sequence is selected from the group consisting of:
i. nucleotide sequences encoding an acetoin reductase, said acetoin reductase comprising an amino acid sequence that has at least 40% sequence identity with the amino acid sequence of SEQ ID NO:81.
ii. nucleotide sequences comprising a nucleotide sequence that has at least 40% sequence identity with the nucleotide sequence of SEQ ID NO:82.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code, (e) a nucleotide sequence encoding a glycerol dehydratase (i.e. a large, medium and small subunit thereof), wherein said nucleotide sequence is selected from the group consisting of:
i. nucleotide sequences encoding a large, medium and small subunits of a glycerol dehydratase, said large, medium and small subunits of a glycerol dehydratase comprising an amino acid sequence that has at least 40% sequence identity with the amino acid sequence of SEQ ID NO:83, 84 and 85 respectively.
ii. nucleotide sequences encoding a large, medium and small subunits of said enzyme, said nucleotide sequence comprising a nucleotide sequence that has at least 40% sequence identity with the nucleotide sequence of SEQ ID NO:86, 87 and 88 respectively.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code and (f) a nucleotide sequence encoding a 1,3-propanediol dehydrogenase, wherein said nucleotide sequence is selected from the group consisting of:
i. nucleotide sequences encoding a 1,3-propanediol dehydrogenase, said 1,3-propanediol dehydrogenase. comprising an amino acid sequence that has at least 40% sequence identity with the amino acid sequence of SEQ ID NO:89.
ii. nucleotide sequences comprising a nucleotide sequence that has at least 40% sequence identity with the nucleotide sequence of SEQ ID NO:90.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code.

Acetone as Organic Product

When an organic product to be produced is acetone, preferred nucleic acid molecules code for enzymes capable of converting pyruvate into acetone and/or into an intermediary compound produced in the pathway leading to acetone, said enzymes comprise a thiolase, an acetoacetyl-CoA transferase and an acetoacetate decarboxylase. Therefore, in this preferred embodiment, a Cyanobacterium comprises a nucleic acid molecule encoding a thiolase, an acetoacetylCoA transferase and another one encoding an acetoacetylCoA decarboxylase. Accordingly, this preferred embodiment relates to a Cyanobacterium capable of expressing the following nucleic acid molecules being represented by nucleotide sequences, wherein the expression of these nucleotide sequences confers on the cell the ability to convert pyruvate into acetone:

(a) a nucleotide sequence encoding a thiolase, wherein said nucleotide sequence is selected from the group consisting of:
i. nucleotide sequences encoding a thiolase, said thiolase comprising an amino acid sequence that has at least 40% sequence identity with the amino acid sequence of SEQ ID NO:23.
ii. nucleotide sequences comprising a nucleotide sequence that has at least 40% sequence identity with the nucleotide sequence of SEQ ID NO:24.
iii. nucleotide sequences the complementary strand of which hybridizes to a nucleic acid molecule of sequence of (i) or (ii);
iv. nucleotide sequences the sequences of which differs from the sequence of a nucleic acid molecule of (iii) due to the degeneracy of the genetic code, (b) a nucleotide sequence encoding an acetoacetylCoA transferase, wherein said nucleotide sequence is selected from the group consisting of:
i. nucleotide sequences encoding an acetoacetylCoA transferase, said acetoacetylCoA transferase comprising an amino acid sequence that has at least 40% sequence identity with the amino acid sequence of SEQ ID NO:95 and another one having the same sequence identity with SEQ ID NO: 96.
  ii. nucleotide sequences comprising a nucleotide sequence that has at least 40% sequence identity with the nucleotide sequence of SEQ ID NO:97 and another one having the same sequence identity with SEQ ID NO: 98.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code and
(c) a nucleotide sequence encoding an acetoacetylCoA decarboxylase, wherein said nucleotide sequence is selected from the group consisting of:
  i. nucleotide sequences encoding an acetoacetylCoA decarboxylase, said acetoacetylCoA decarboxylase comprising an amino acid sequence that has at least 40% sequence identity with the amino acid sequence of SEQ ID NO:25.
  ii. nucleotide sequences comprising a nucleotide sequence that has at least 40% sequence identity with the nucleotide sequence of SEQ ID NO:26.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code.

1,3-Propanediol as Organic Product

When an organic product to be produced is 1,3-propanediol, preferred nucleic acid molecules code for enzymes capable of converting glyceraldehyde-3-phosphate into propanediol and/or into an intermediary compound produced in the pathway leading to 1,3-propanediol, said enzymes comprise a glycerol-3-P-dehydrogenase, a glycerol-3-P-phosphatase, a glycerol dehydratase and an oxidoreductase. A first intermediary product is glycerol. A preferred assay for glycerol is HPLC. A detectable amount of glycerol is preferably at least 0.1 mM under said culture conditions as defined earlier herein and using said assay. A second intermediary product is hydroxypropionaldehyde. A preferred assay for hydroxypropionaldehyde is HPLC. A detectable amount of hydroxypropionaldehyde is preferably at least 0.1 mM under said culture conditions as defined earlier herein and using said assay. Alternatively, a cell may produce a combination of a first and a second intermediary product as defined above. In this case, a detectable amount of a first and a second intermediary product as defined above is at least 0.1 mM of each intermediary product. Therefore in this preferred embodiment, a Cyanobacterium comprises a nucleic acid molecule encoding a glycerol-3-P-dehydrogenase, a glycerol-3-P-phosphatase, a glycerol dehydratase and an oxidoreductase. Accordingly, this preferred embodiment relates to a Cyanobacterium capable of expressing the following nucleic acid molecules being represented by nucleotide sequences, wherein the expression of these nucleotide sequences confers on the cell the ability to convert glyceraldehyde-3-phosphate into glycerol, hydroxypropionaldehyde and/or 1,3-propanediol:
  (a) a nucleotide sequence encoding a glycerol-3-P-dehydrogenase, wherein said nucleotide sequence is selected from the group consisting of:
    i. nucleotide sequences encoding a glycerol-3-P-dehydrogenase, said glycerol-3-P-dehydrogenase comprising an amino acid sequence that has at least 40% sequence identity with the amino acid sequence of SEQ ID NO:27.
    ii. nucleotide sequences comprising a nucleotide sequence that has at least 40% sequence identity with the nucleotide sequence of SEQ ID NO:28.
    iii. nucleotide sequences the complementary strand of which hybridizes to a nucleic acid molecule of sequence of (i) or (ii);
    iv. nucleotide sequences the sequences of which differs from the sequence of a nucleic acid molecule of (iii) due to the degeneracy of the genetic code,
  (b) a nucleotide sequence encoding a glycerol-3-P-phosphatase, wherein said nucleotide sequence is selected from the group consisting of:
    i. nucleotide sequences encoding a glycerol-3-P-phosphatase, said glycerol-3-P-phosphatase comprising an amino acid sequence that has at least 40% sequence identity with the amino acid sequence of SEQ ID NO:29.
    ii. nucleotide sequences comprising a nucleotide sequence that has at least 40% sequence identity with the nucleotide sequence of SEQ ID NO:30.
    iii. nucleotide sequences the complementary strand of which hybridizes to a nucleic acid molecule of sequence of (i) or (ii);
    iv. nucleotide sequences the sequences of which differs from the sequence of a nucleic acid molecule of (iii) due to the degeneracy of the genetic code,
  (c) a nucleotide sequence encoding a glycerol dehydratase, wherein said nucleotide sequence is selected from the group consisting of:
    i. nucleotide sequences encoding a glycerol dehydratase, said glycerol dehydratase comprising an amino acid sequence that has at least 40% sequence identity with the amino acid sequence of SEQ ID NO:31.
    ii. nucleotide sequences comprising a nucleotide sequence that has at least 40% sequence identity with the nucleotide sequence of SEQ ID NO:32.
    iii. nucleotide sequences the complementary strand of which hybridizes to a nucleic acid molecule of sequence of (i) or (ii);
    iv. nucleotide sequences the sequences of which differs from the sequence of a nucleic acid molecule of (iii) due to the degeneracy of the genetic code, and
  (d) a nucleotide sequence encoding an oxidoreductase, wherein said nucleotide sequence is selected from the group consisting of:
    i. nucleotide sequences encoding an oxidoreductase, said oxidoreductase comprising an amino acid sequence that has at least 40% sequence identity with the amino acid sequence of SEQ ID NO:33.
    ii. nucleotide sequences comprising a nucleotide sequence that has at least 40% sequence identity with the nucleotide sequence of SEQ ID NO:34.
    iii. nucleotide sequences the complementary strand of which hybridizes to a nucleic acid molecule of sequence of (i) or (ii);
    iv. nucleotide sequences the sequences of which differs from the sequence of a nucleic acid molecule of (iii) due to the degeneracy of the genetic code.

D-Lactate as Organic Product

When an organic product to be produced is D-lactate, preferred nucleic acid molecules code for enzymes capable of converting pyruvate into D-lactate, said enzyme comprise a lactate dehydrogenase. Preferred assays for D-lactate are HPLC and enzymatic assays.

A detectable amount by HPLC of D-lactate is preferably at least 0.1 mM under said culture conditions as defined earlier herein and using said assay. A detectable amount by enzymatic assays of D-lactate is preferably at least 0.2 mg/l under said culture conditions as defined earlier herein and using said assay. Therefore, in this preferred embodiment, a Cyanobacterium comprises a nucleic acid molecule encoding a lactate dehydrogenase. Accordingly, this preferred embodiment relates to a Cyanobacterium capable of expressing at least one nucleic acid molecule, said nucleic acid molecule being represented by a nucleotide sequence, wherein the expression of this nucleotide sequence confers on the cell the ability to convert pyruvate into D-lactate:

(a) a nucleotide sequence encoding a lactate dehydrogenase, wherein said nucleotide sequence is selected from the group consisting of:
  i. nucleotide sequences encoding a lactate dehydrogenase, said lactate dehydrogenase comprising an amino acid sequence that has at least 40% sequence identity with the amino acid sequence of SEQ ID NO:35.
  ii. nucleotide sequences comprising a nucleotide sequence that has at least 40% sequence identity with the nucleotide sequence of SEQ ID NO:36.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code.

Ethylene as Organic Product

When an organic product to be produced is ethylene, preferred nucleic acid molecules code for enzymes capable of converting 2-oxoglutarate into ethylene and succinate, said enzyme comprise a ethylene forming enzyme (2-oxoglutarate-dependent ethylene-forming enzyme). A preferred assay for ethylene is GC (gas chromatography) under said culture conditions as defined earlier herein and using said assay. As shown by (Pirkov I et al, (2008), Metabolic Engineering, 10: 276-280). A detectable amount of ethylene is preferably at least 10 μg/lh. Therefore, in this preferred embodiment, a Cyanobacterium comprises a nucleic acid molecule encoding a ethylene forming enzyme. Accordingly, this preferred embodiment relates to a Cyanobacterium capable of expressing at least one nucleic acid molecule, said nucleic acid molecule being represented by a nucleotide sequence, wherein the expression of this nucleotide sequence confers on the cell the ability to convert 2-oxoglutarate into ethylene and succinate:

(a) a nucleotide sequence encoding a ethylene forming enzyme, wherein said nucleotide sequence is selected from the group consisting of:
  i. nucleotide sequences encoding a ethylene forming enzyme, said ethylene forming enzyme comprising an amino acid sequence that has at least 40% sequence identity with the amino acid sequence of SEQ ID NO:91.
  ii. nucleotide sequences comprising a nucleotide sequence that has at least 40% sequence identity with the nucleotide sequence of SEQ ID NO:92.
  iii. nucleotide sequences the complementary strand of which hybridizes to a nucleic acid molecule of sequence of (i) or (ii);
  iv. nucleotide sequences the sequences of which differs from the sequence of a nucleic acid molecule of (iii) due to the degeneracy of the genetic code.

Each nucleotide sequence or amino acid sequence described herein by virtue of its identity percentage (at least 40%) with a given nucleotide sequence or amino acid sequence respectively has in a further preferred embodiment an identity of at least 45%, 50%, 55%, 60%, 65%, 70%, 75%, 80%, 85%, 90%, 95%, 98%, 99% or more identity with the given nucleotide or amino acid sequence respectively. In a preferred embodiment, sequence identity is determined by comparing the whole length of the sequences as identified herein.

Each nucleotide sequence encoding an enzyme as described herein may encode either a prokaryotic or an eukaryotic enzyme, i.e. an enzyme with an amino acid sequence that is identical to that of an enzyme that naturally occurs in a prokaryotic or eukaryotic organism. The present inventors have found that the ability of a particular enzyme or to a combination of particular enzymes as defined herein to confer to a Cyanobacterial cell the ability to convert a glycolytic intermediate into an organic product and/or into an intermediary compound produced in the pathway leading to the organic compound does not depend so much on whether the enzyme is of prokaryotic or eukaryotic origin. Rather this depends on the relatedness (identity percentage) of the enzyme amino acid sequence or corresponding nucleotide sequence to that of the corresponding identified SEQ ID NO.

Alternatively or in combination with previous preferred embodiments, the invention relates to a further preferred embodiment, wherein at least one enzyme as defined herein is substantially not sensitive towards oxygen inactivation. "Being substantially not sensitive towards oxygen inactivation" preferably means that when such enzyme is expressed in a Cyanobacterium as described herein and when this Cyanobacterium is cultured in a process of the invention, significant activity of said enzyme is detectable using a specific assay known to the skilled person. More preferably, a significant activity of said enzyme is at least 20% of the activity of the same enzyme expressed in the same Cyanobacterium but cultured in the absence of oxygen. Even more preferably, at least 30%, 35%, 40%, 45%, 50%, 55%, 60%, 65%, 70%, 75%, 80%, 85%, 90%, 95% of the activity is detectable. Most preferably, the activity of said enzyme as expressed in a Cyanobacterium as described herein and when this Cyanobacterium is cultured in the process of the invention is identical with the activity of the same enzyme as expressed in a same Cyanobacterium as described herein and when this Cyanobacterium is cultured in the absence of oxygen. This is an advantage of the present invention that the Cyanobacterium hence obtained is preferably used in a process of the invention wherein oxygen is produced, since it will substantially not affect the activity of the enzymes used herein.

Alternatively or in combination with previous preferred embodiments, the invention relates to a further preferred embodiment wherein, a Cyanobacterium as defined herein is a Cyanobacterium that has been transformed with a nucleic acid construct comprising a nucleotide sequence encoding an enzyme as defined above depending on the organic product to be produced. A nucleic acid construct comprising a nucleic acid molecule coding for a given enzyme as defined herein will ensure expression of the given nucleic acid molecule, and of the corresponding enzyme in a Cyanobacterium. In a more preferred embodiment, a nucleic acid construct comprises more than one nucleic acid molecule, each nucleic acid molecule coding for a given enzyme. In an even more preferred embodiment, a nucleic acid construct comprises two, three, four nucleic acid molecules, each nucleic acid molecule coding for a given enzyme. In a most preferred embodiment, a nucleic acid construct comprises all nucleic acid molecules needed for the conversion of a glycolytic intermediate into an organic product and/or an intermediary compound, each nucleic acid molecule coding for a given enzyme. This most preferred embodiment is illustrated in example 2. In this most preferred embodiment, a nucleic acid construct comprises an expression cassette, said expression cassette comprising each needed nucleic acid molecule. Each nucleic acid molecule is operably linked with other nucleic acid molecule present. Most preferably, a suitable promoter is operably linked with the expression cassette to ensure expression of the nucleic acid molecule in a Cyanobacterium as later defined herein.

To this end, a nucleic acid construct may be constructed as described in e.g. U.S. Pat. Nos. 6,699,696 or 4,778,759. A Cyanobacterium may comprise a single but preferably comprises multiple copies of each nucleic acid construct. A nucleic acid construct may be maintained episomally and thus comprises a sequence for autonomous replication, such as an ARS sequence. Suitable episomal nucleic acid constructs may e.g. be based on the yeast 2µ or pKD1 (Fleer et al., 1991, Biotechnology 9:968-975) plasmids. Preferably, however, each nucleic acid construct is integrated in one or more copies into the genome of a cyanobacterial cell. Integration into a cyanobacterial cell's genome may occur at random by illegitimate recombination but preferably a nucleic acid construct is integrated into the Cyanobacterium cell's genome by homologous recombination as is well known in the art (U.S. Pat. No. 4,778,759). Homologous recombination occurs preferably at a neutral integration site. A neutral integration site is an integration which is not expected to be necessary for the production process of the invention, i.e for the growth and/or the production of an organic compound and/or an intermediary compound as defined herein. A preferred integration site is the nrt operon as illustrated in the examples (Osanai, T., Imamura, S., Asayama, M., Shirai, M., Suzuki, I., Murata, N., Tanaka, K, (2006) Nitrogen induction of sugar catabolic gene expression in *Synechocystis* sp. PCC 6803. *DNA Research* 13, 185-19). Accordingly, in a more preferred embodiment, a cyanobacterial cell of the invention comprises a nucleic acid construct comprising a nucleic acid molecule, said nucleic acid molecule being represented by a nucleotide sequence, said nucleotide sequence being a coding sequence of an enzyme as identified herein. Said cyanobacterial cell is capable of expression of these enzymes. In an even more preferred embodiment, a nucleic acid molecule encoding an enzyme is operably linked to a promoter that causes sufficient expression of a corresponding nucleic acid molecule in a Cyanobacterium to confer to a Cyanobacterium the ability to convert a glycolytic intermediate into a given organic product and/or into an intermediary compound produced in the pathway leading to the organic product. In case of an expression cassette as earlier defined herein, a promoter is upstream of the expression cassette. Accordingly, in a further aspect, the invention also encompasses a nucleic acid construct as earlier outlined herein. Preferably, a nucleic acid construct comprises a nucleic acid molecule encoding an enzyme as earlier defined herein. Nucleic acid molecules encoding an enzyme have been all earlier defined herein.

A promoter that could be used to achieve the expression of a nucleic acid molecule coding for an enzyme as defined herein may be not native to a nucleic acid molecule coding for an enzyme to be expressed, i.e. a promoter that is heterologous to the nucleic acid molecule (coding sequence) to which it is operably linked. Although a promoter preferably is heterologous to a coding sequence to which it is operably linked, it is also preferred that a promoter is homologous, i.e. endogenous to a Cyanobacterium. Preferably, a heterologous promoter (to the nucleotide sequence) is capable of producing a higher steady state level of a transcript comprising a coding sequence (or is capable of producing more transcript molecules, i.e. mRNA molecules, per unit of time) than is a promoter that is native to a coding sequence, preferably under conditions where sun light and carbon dioxide are present. A suitable promoter in this context includes both constitutive and inducible natural promoters as well as engineered promoters. A promoter used in a Cyanobacterium cell of the invention may be modified, if desired, to affect its control characteristics. A preferred promoter is a SigE controlled promotor of the glyceraldehyde dehydrogenase gene from *Synechocystis* PCC 6083 as identified in SEQ ID NO:74 (Takashi Osanai, et al, Positive Regulation of Sugar Catabolic Pathways in the Cyanobacterium *Synechocystis* sp. PCC 6803 by the Group 2 sigma Factor SigE. J. Biol. Chem. (2005) 35: 30653-30659). This promoter is quite advantageous to be used as outlined below in the next paragraph.

Alternatively or in combination with previous preferred embodiments, the invention relates to a further preferred embodiment, wherein the expression of a nucleic acid molecule as defined herein is regulated so as to respond to a change in the concentration of a nutrient such as ammonium (Osanai, T., Imamura, S., Asayama, M., Shirai, M., Suzuki, I., Murata, N., Tanaka, K, (2006) Nitrogen induction of sugar catabolic gene expression in *Synechocystis* sp. PCC 6803. *DNA Research* 13, 185-195). In a more preferred embodiment, the expression of a nucleic acid molecule is induced when ammonium concentration is below a given value. As exemplified in example 2, this is preferably achieved by using a SigE promoter in a nucleic acid construct comprising a nucleic acid molecule as defined herein. Such promoter is inactive in a first phase of the process when ammonium is present in a concentration which is approximately above 1 mM. In this first phase, a Cyanobacterium will grow and not produce any organic compound and/or any intermediary compound as defined herein. When the ammonium source, has been used for growth and its concentration is approximately below 1 mM, the SigE promoter is induced. As a consequence, the process is divided in 2 phase, a first phase where cell numbers increase and a second phase of the production process of the invention, which is characterized by the production of an organic compound and/or an intermediary compound as defined herein. This two phased production process has several advantages compared to one phase production processes: a) the growth phase is separated from the production phase and therefore high cell densities can be obtained in a short time b) the yield of an organic product and/or of an intermediary compound as defined herein will be improved due to the fact that no carbon flux to growth will occur in the second phase. The skilled person knows how to assess the concentration of a nutrient such as ammonium in the culture.

Method

In a second aspect, the invention relates to a process of producing an organic compound and/or an intermediary compound as defined herein by feeding carbon dioxide to a culture of a cyanobacterial cell and subjecting said culture to light, wherein said cell is capable of expressing a nucleic acid molecule, wherein the expression of said nucleic acid molecule confer on the cell the ability to convert a glycolytic intermediate into an organic compound and/or into an intermediary compound produced in the pathway leading to the organic compound and wherein said nucleic acid molecule is under the control of a regulatory system which responds to a change in the concentration of a nutrient in said culture.

A Cyanobacterium, a glycolytic intermediate, an organic compound, an intermediary compound, a nucleic acid molecule, and a regulatory system have all earlier been defined herein.

In a process of the invention, carbon dioxide is fed to a culture broth of Cyanobacteria. The skilled person knows that the carbon dioxide concentration is dependent from the temperature, the pH and the concentration of carbon dioxide present in the air used. Therefore, this is quite difficult to give an estimation of the concentration of carbon dioxide which is being used. Below, we give estimations of preferred concentrations used. A preferred feeding concentration of carbon dioxide is air enriched to 5% carbon dioxide. A preferred source of carbon dioxide may be the waste gas from an industrial plant.

Usually a process is started with a culture (also named culture broth) of Cyanobacteria having an optical density measured at 660 nm of approximately 0.2 to 2.0 ($OD_{660}$=0.2 to 2) as measured in any conventional spectrophotometer with a measuring path length of 1 cm. Usually the cell number in the culture doubles every 20 hours. A preferred process takes place in a tank with a depth of 30-50 cm exposed to sun light. In a preferred process, the number of cells increases until the source of ammonium is exhausted or below a given value as earlier explained herein, subsequently the production of said products and/or intermediates will start. In a preferred embodiment, the light used is natural. A preferred natural light is sunlight. Sunlight may have an intensity ranged between approximately 1000 and approximately 1500 $\mu Einstein/m^2/s$. In another preferred embodiment, the light used is artificial. Such artificial light may have an intensity ranged between approximately 70 and approximately 800 $\mu Einstein/m^2/s$.

In a preferred process, an organic compound and/or an intermediate compound produced is separated from the culture broth. This may be realized continuously with the production process or subsequently to it. Separation may be based on membrane technology and/or evaporation methods. Depending on the identity of the organic compound and/or of intermediary compound produced, the skilled person will know which separating method is the most appropriate.

General Definitions

Sequence Identity and Similarity

Sequence identity is herein defined as a relationship between two or more amino acid (polypeptide or protein) sequences or two or more nucleic acid (polynucleotide) sequences, as determined by comparing the sequences. Usually, sequence identities or similarities are compared over the whole length of the sequences compared. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by various methods, known to those skilled in the art. In a preferred embodiment, sequence identity is determined by comparing the whole length of the sequences as identified herein.

Preferred methods to determine identity are designed to give the largest match between the sequences tested. Methods to determine identity and similarity are codified in publicly available computer programs. Preferred computer program methods to determine identity and similarity between two sequences include e.g. the BestFit, BLASTP, BLASTN, and FASTA (Altschul, S. F. et al., J. Mol. Biol. 215:403-410 (1990), publicly available from NCBI and other sources (BLAST Manual, Altschul, S., et al., NCBI NLM NIH Bethesda, Md. 20894). A most preferred algorithm used is EMBOSS (http://www.ebi.ac.uk/emboss/align). Preferred parameters for amino acid sequences comparison using EMBOSS are gap open 10.0, gap extend 0.5, Blosum 62 matrix. Preferred parameters for nucleic acid sequences comparison using EMBOSS are gap open 10.0, gap extend 0.5, DNA full matrix (DNA identity matrix).

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

Hybridising Nucleic Acid Sequences

Nucleotide sequences encoding the enzymes expressed in the cell of the invention may also be defined by their capability to hybridise with the nucleotide sequences of SEQ ID NO.'s 2, 4, 6, 8, 16, 18, 20, 22, 24, 26, 28, 30, 32, 34, 36, 76, 78, 80, 82, 86, 87, 88, 90, 92, 96 respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

Homologous

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically be operably linked to another promoter sequence than in its natural environment. When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as earlier presented. Preferably the region of identity is greater than about 5 bp, more preferably the region of identity is greater than 10 bp. Preferably, two nucleic acid or polypeptides sequences are said to be homologous when they have more than 80% identity.

Heterologous

The term "heterologous" when used with respect to a nucleic acid (DNA or RNA) or protein refers to a nucleic acid or protein (also named polypeptide or enzyme) that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

Operably Linked

As used herein, the term "operably linked" refers to a linkage of polynucleotide elements (or coding sequences or nucleic acid sequence or nucleic acid molecule) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence. Operably linked means that the nucleic acid sequences being linked are typically contiguous and, where necessary to join two protein coding regions, contiguous and in reading frame.

Promoter

As used herein, the term "promoter" refers to a nucleic acid fragment that functions to control the transcription of one or more nucleic acid molecules, located upstream with respect to the direction of transcription of the transcription initiation site of the nucleic acid molecule, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active under most environmental and developmental conditions. An "inducible" promoter is a promoter that is active under environmental or developmental regulation.

Genetic Modifications

For overexpression of an enzyme in a host cells= of the inventions as described above, as well as for additional genetic modification of a host cell=, preferably Cyanobacteria, host cells are transformed with the various nucleic acid constructs of the invention by methods well known in the art. Such methods are e.g. known from standard handbooks, such as Sambrook and Russel (2001) "Molecular Cloning: A Laboratory Manual ($3^{rd}$ edition), Cold Spring Harbor Laboratory, Cold Spring Harbor Laboratory Press, or F. Ausubel et al, eds., "Current protocols in molecular biology", Green Publishing and Wiley Interscience, New York (1987). Methods for transformation and genetic modification of cyanobacterial cells are known from e.g. U.S. Pat. Nos. 6,699,696 or 4,778,759.

A promoter for use in a nucleic acid construct for overexpression of an enzyme in a cyanobacterial cell of the invention has been described above. Optionally, a selectable marker may be present in a nucleic acid construct. As used herein, the term "marker" refers to a gene encoding a trait or a phenotype which permits the selection of, or the screening for, a Cyanobacterial cell containing the marker. A marker gene may be an antibiotic resistance gene whereby the appropriate antibiotic can be used to select for transformed cells from among cells that are not transformed. Preferably however, a non-antibiotic resistance marker is used, such as an auxotrophic marker (URA3, TRP1, LEU2). In a preferred embodiment, a Cyanobacterial cell transformed with a nucleic acid construct is marker gene free. Methods for constructing recombinant marker gene free microbial host cells are disclosed in EP-A-0 635 574 and are based on the use of bidirectional markers. Alternatively, a screenable marker such as Green Fluorescent Protein, lacZ, luciferase, chloramphenicol acetyltransferase, beta-glucuronidase may be incorporated into a nucleic acid construct of the invention allowing to screen for transformed cells.

Optional further elements that may be present in a nucleic acid construct of the invention include, but are not limited to, one or more leader sequences, enhancers, integration factors, and/or reporter genes, intron sequences, centromers, telomers and/or matrix attachment (MAR) sequences. A nucleic acid construct of the invention can be provided in a manner known per se, which generally involves techniques such as restricting and linking nucleic acids/nucleic acid sequences, for which reference is made to the standard handbooks, such as Sambrook and Russel (2001) "Molecular Cloning: A Laboratory Manual ($3^{rd}$ edition), Cold Spring Harbor Laboratory, *Cold Spring Harbor Laboratory Press*.

Methods for inactivation and gene disruption in Cyanobacterial cells are well known in the art (see e.g. Shestakov S V et al, (2002), Photosynthesis Research, 73: 279-284 and Nakamura Y et al, (1999), Nucleic Acids Res. 27:66-68).

In this document and in its claims, the verb "to comprise" and its conjugations is used in its non-limiting sense to mean that items following the word are included, but items not specifically mentioned are not excluded. In addition the verb "to consist" may be replaced by "to consist essentially of" meaning that a peptide or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety. The following examples are offered for illustrative purposes only, and are not intended to limit the scope of the present invention in any way

DESCRIPTION OF THE FIGURES

FIG. 6: A preferred design of expression cassettes is given in FIG. 6.

EXAMPLES

Example 1: Biochemical Background of the Cyanobacteria of the Invention

Figure 1:
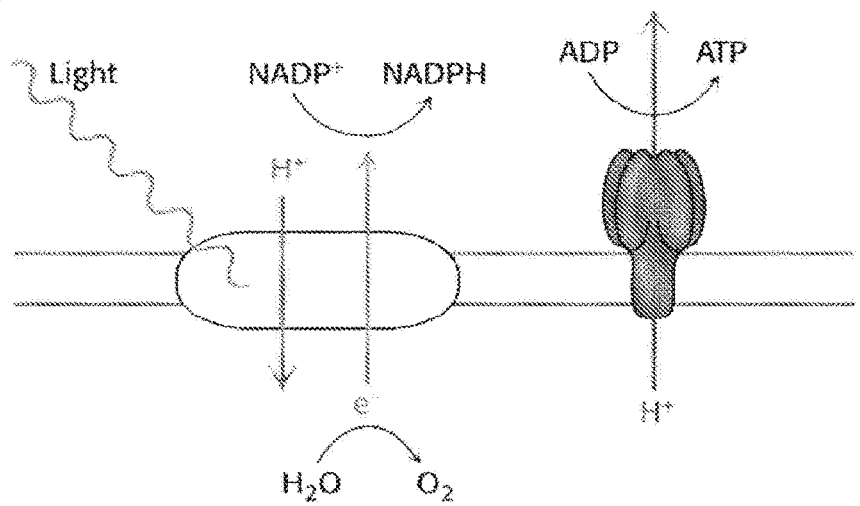
FIG. 1: The light reaction reproduced from Berg, Tymoczko and Stryer: "Biochemistry" WH Freeman and Co, New York, 2006.

The energy, in the form of ATP, as well as the reductive power in the form of NADPH, that are both needed to drive the subsequent highly endergonic dark reactions of photosynthesis, are catalyzed by the two photosystems of oxygenic photosynthesis, PS-II and PS-I, arranged according to the well-known Z-scheme, plus the membrane-bound ATPase (FIG. 1).

Figure 2:
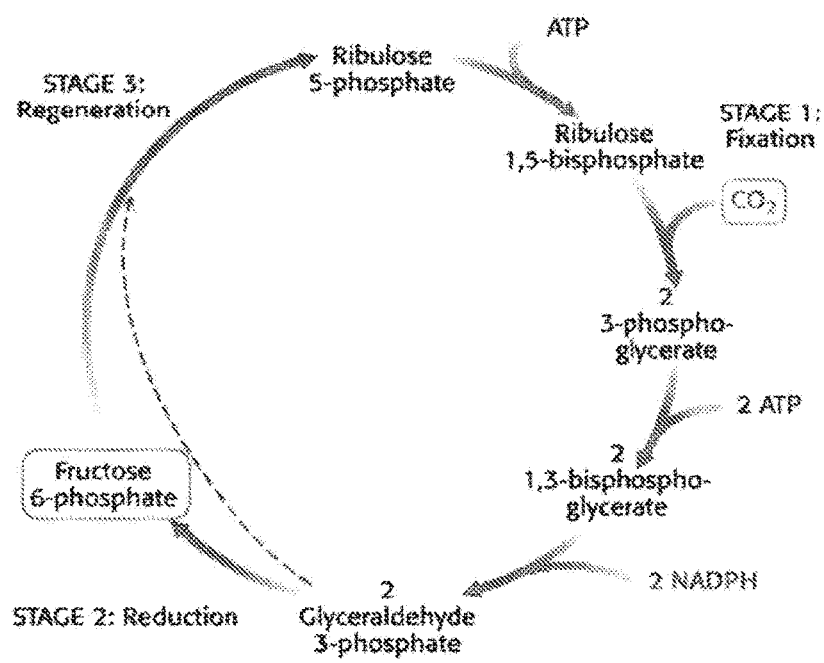
FIG. 2: The Calvin Cycle reproduced from Berg, Tymoczko and Stryer: "Biochemistry" WH Freeman and Co, New York, 1 2006.

In phototrophic organisms like Cyanobacteria, $CO_2$ is fixed in the so-called Calvin cycle. This is a cyclic series of reductive steps that result in the net conversion of $CO_2$ into C3 compounds, such as glyceraldehyde-3-phosphate, phosphoglycerate and pyruvate (FIG. 2).

This pathway is essentially endergonic and in Nature driven by sunlight. It consumes $CO_2$ and water and yields C3 compounds (e.g. pyruvate) and oxygen:

$$CO_2 + H_2O + \text{Solar energy} \rightarrow \text{C3 compounds} + O_2 \qquad (1)$$

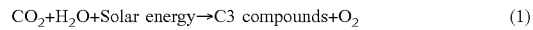

This reaction cannot proceed spontaneously: It is driven by the consumption of the ATP and NADPH, generated in the 'light' reactions of photosynthesis. Subsequently, the C3 compounds are used in Nature (i.e. in phototrophic organisms like plants and Cyanobacteria) as the building blocks to make new cells and/or plants. This requires additional amounts of reducing power (as NADPH) and energy conserved during the light capturing reactions (as ATP) and also allows the organisms to proliferate (grow and survive).

Nature also sustains an entirely different mode of (microbial) life: Numerous bacterial and fungal species are able to conserve sufficient energy (as ATP) to proliferate by fermentation, in which they use so-called substrate level phosphorylation to generate their energy. This respiration-independent mode of energy conservation relies on metabolic pathways that result in redox neutral dissimilation of the energy source. The most abundant pathways have evolved with sugars (e.g. glucose) as energy source and therefore all have glycolysis in common:

$$\text{Glucose} \rightarrow \text{glyceraldehyde-P} \rightarrow \text{pyruvate} + \text{reducing power} \qquad (2)$$

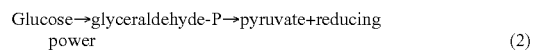

Redox neutrality is maintained by the generalized reaction:

$$\text{pyruvate} + \text{reducing power} \rightarrow \text{fermentation products} \qquad (3)$$

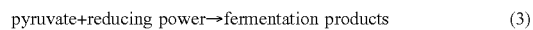

Thus, it will contain the functional biochemistry to reduce the above-mentioned intermediates to the end product and will have as its biocatalytic input and output the combination of (1) and (3), respectively:

$$CO_2 + H_2O + \text{Solar energy} \rightarrow \text{organic product} + O_2$$

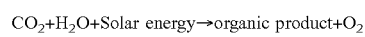

Example 2: Description of the Expression System Used

Genetic Cassettes

Figure 4:
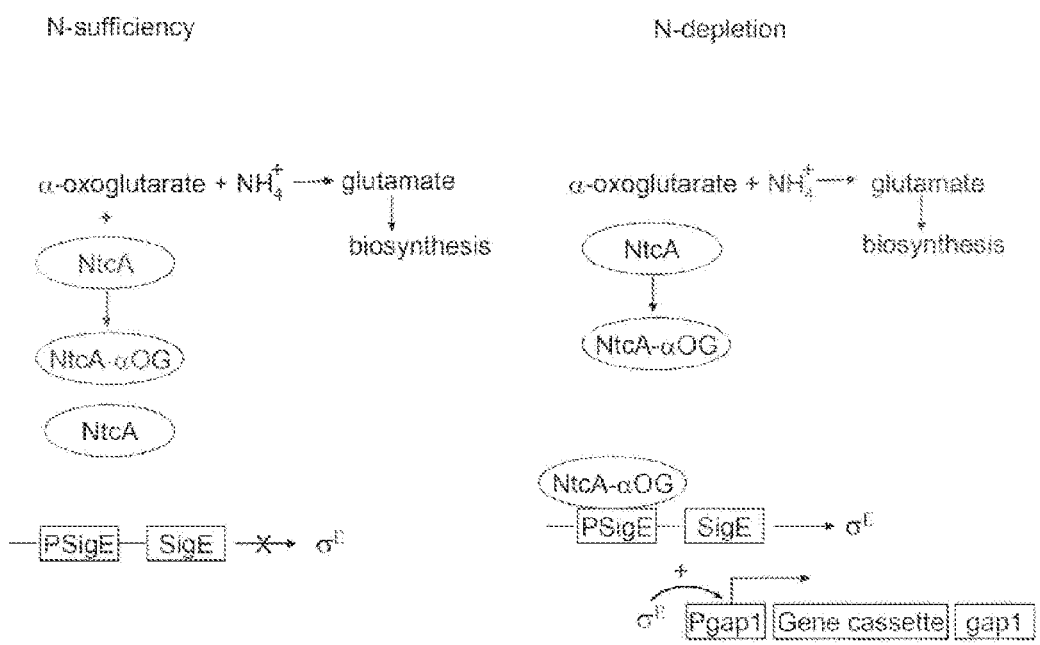
FIG. 4: Ammonium controlled production via the NtcA transcriptional regulator. Conditions allowing growth repress production, ammonium depletion promotes production.

The identity of an organic product formed (and excreted into the environment) in the process of the invention depends on the species-specific gene cassettes (i.e. nucleic acid molecules represented by nucleotide sequences) that encode the respective biochemical pathway (see table 1). Preferred enzymes encoded by nucleic acid molecules are substantially oxygen insensitive.

directed towards biosynthesis whereas in the stationary phase this flux will be directed to production (see FIG. 4). For Synechococcus the external ammonium threshold for the switch to $\sigma^E$ synthesis was found to be submillimolar range[2].

TABLE 1

Examples of preferred donor organisms for the nucleic acid molecules or genes to be introduced into a Cyanobacterium with the pathway they catalyze. For e.g. the production of ethanol and propanediol various alternative donor organisms can be suggested.

| donor | genes | pathway |
|---|---|---|
| Sarcina ventriculi | pyruvate decarboxylase, | Pyruvate → acetaldehyde |
| Lactobacillus brevis | alcohol dehydrogenase | Acetaldehyde → ethanol |
| Clostridium acetobutilicum | thiolase hydroxybutyrylCoA dehydrogenase crotonase butyryl-CoA dehydrogenase Butanol dehydrogenase | pyruvate → acetoacetylCoA acetoacetylCoA → butyrylCoA butyrylCoA → butyraldehyde butyraldehyde → 2-butanol |
| Pseudomonas syringiae | ethylene forming enzyme | 2-ketoglutarate → ethylene |
| Lactococcus lactis | lactate dehydrogenase | pyruvate → D-lactate |
| Lactococcus lactis | acetolactate synthase | pyruvate → 2-acetolactate |
| Klebsiella pneumoniae | acetolactate decarboxylase diacetyl reductase acetoin reductase glycerol dehydratase 1,3 propanediol dehydrogenase | 2-acetolactate → acetoin diacetyl → acetoin acetoin → 2,3 butanediol 2,3 butanediol → 2-butanone 2-butanone → 2-butanol |
| Clostridium acetobutilicum | thiolase ac.acetylCoA transferase acetoacetate decarboxylase | acetylCoA → acetoacetylCoA acetoacetylCoA → acetoacetate acetoacetate → acetone |
| Clostridium acetobutilicum | thiolase ac.acetylCoA transferase acetoacetate decarboxylase propanol dehydrogenase | acetylCoA → acetoacetylCoA acetoacetylCoA → acetoacetate acetoacetate → acetone acetone → propanol |
| Klebsiella pneumoniae | | |
| Synechocystis PCC 6083 | glycerol-3-P dehydrogenase glycerol-3-P Phosphatase | GAP → glycerol-P glycerol-P → glycerol |
| K. pneumoniae | glycerol dehydratase oxidoreductase | glycerol → OHpropionaldehyde OHprop.aldehyde → 1,3-propanediol |

Homologous Integration and Ammonium Controlled Expression

Figure 3:
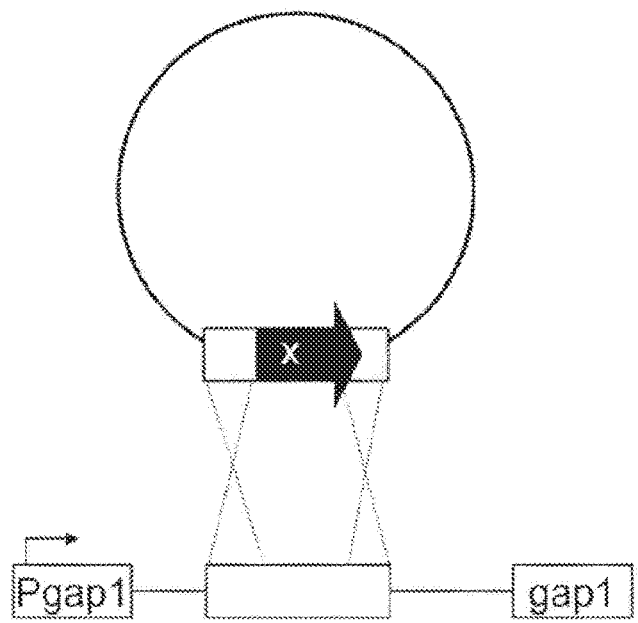
FIG. 3: Construction of a recombinant strain: The cassette is introduced by homologous recombination and positioned downstream the SigE controlled promotor of *Synechocystis* PCC 6803. The black circle shows the suicide plasmid (e.g. pBluescript) that is not able to replicate in *Synechocystis* PCC 6803. The cassette(s) of interest (denoted as arrow "x" in the figure) will be engineered to be flanked by DNA sequences homologous to a non-coding DNA region (shown as a dotted bar in the figure) in the nrt operon. Via a double crossover event, shown in the figure as dashed crosses, the cassettes of interest are integrated into the *Synechocystis* genome. Alternatively, the construct can be inserted at a neutral docking site.

The genes/cassettes, necessary for the different pathways and respective organic products in Synechocystis, are preferably introduced to Synechocystis via chromosomal integration. This will be achieved by homologous recombination which allows to precisely define the chromosomal site of insertion. Appropriate plasmids for this purpose known to be applicable in Synechocystis sp PCC 6830 are pBluescript (Stratagene, USA) or pGEM-T (Promega, USA). A strategy with respect to the construct is exemplified in FIG. 3 but alternative (neutral) docking sites for integration will be considered.

We will make use of the fact that expression of a number of glycolytic genes of Synechocystis are under control of a group 2 sigma-factor, $\sigma^E$. In turn, expression of the gene encoding this factor, SigE, is switched on by the transcriptional regulator NtcA[1,3]. This switch is, amongst other unidentified signals, dependent on the extracellular nitrogen availability via the intracellular α-oxoglutarate/glutamate ratio: under conditions of ammonium depletion of the medium to less than 1 mM[2], NtcA binds to α-oxoglutarate and the resulting NtcA-α-oxoglutarate complex has a high binding affinity for and positive control on the SigE promotor. Thus, a gene cassette under SigE control will be expressed upon ammonium depletion. As a consequence, during ammonium excess conditions, the carbon flux will be Example 3: Alcohol Resistance Synechocystis PCC 6803 strain was grown on BG-11 medium (Stanier R Y, et al. Purification and properties of unicellular blue-green algae (order Chroococcales). Bacteriol. Rev. (1971) 35:171-205) in an orbital shaker at 30° C. under continuous illumination using two TL tubes, which provided average light intensity of approximately 70 µE·m$^{-2}$·s$^{-1}$. To quantify the influence of alcohols on the net growth rate, cells were grown without any addition (control) or with butanol, respectively ethanol added at various concentrations.

After 5 days, 100 µl of each culture was appropriately diluted and transferred to solid medium prepared from BG-11 and supplemented with 0.3% sodium thiosulfate, 10 mM N-tris[hydroxymethyl]-2-aminoethanesulfonic acid (TES) pH 8.2, 5 mM glucose and 1.5% bactoagar. Solid cultures were grown in an incubator 30° C. under continuous illumination. After a week, single colonies were observed and counted. The amount of colonies was compared to the control sample.

Figure 5:
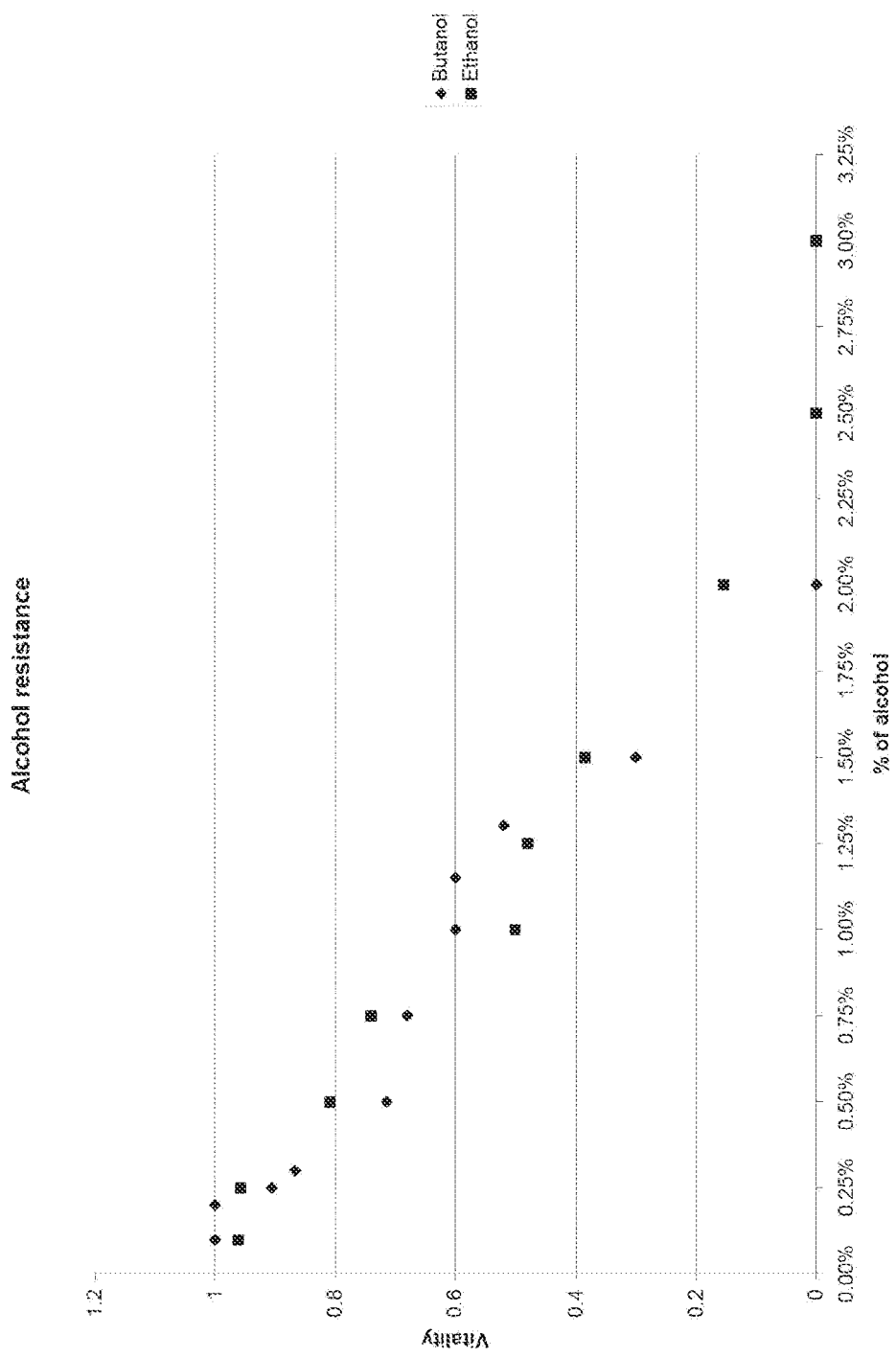
FIG. 5: Alcohol resistance. After five days, 100 µl of each culture was diluted and transferred to solid medium prepared from the BG-11 medium. Solid cultures were grown in an incubator at 30° C. under continuous illumination (70 µEinstein/m²/s) using two TL tubes without any addition (control) or with butanol, respectively ethanol added at various concentrations. After a week, single colonies were observed and counted. The amount of colonies was compared to the control sample.

From the results shown below in FIG. 5, it is concluded that the net specific growth rate decreases linearly with increasing alcohol concentration and that the growth rate is reduced by 50% at concentrations of approximately 0.17 M butanol respectively 0.29 M ethanol. Therefore, it is to be expected that the two phases production process of the invention is much more efficient than a single phase production process.

TABLE 3 list of all primers used

HOMOLOGY REGION 1

| | | |
|---|---|---|
| Forward | AAATGGTACCGAACTGAGATTAGCCCCGGAC | KpnI |
| Reverse | AAATCTCGAGACCAGGACATCCGACTTGC | XhoI |

HOMOLOGY REGION 2

| | | |
|---|---|---|
| Forward | CACGACTAGTGTGACCGGGTCATTTTTTTGCTATTTATTCC | SpeI |
| Reverse | AAATTCTAGATAACTGCGGTAGCACTAAAGCCGCTGCCTTAG | XbaI |

Product: Lactic acid

| | | |
|---|---|---|
| Forward ldh | CAATCTCGAGATGGCTGATAAACAACGTAAG | XhoI |
| Reverse ldh | CAATGAATTCTTAGTTTTTAACTGCAGAAGCAAATTC | EcoRI |

Product: Ethanol

| | | |
|---|---|---|
| Forward pdc | ATAACTCGAGGACAATAGGTGCTTTAATCAC | XhoI |
| Reverse pdc | CGACGATATCAGGTGTAAAATACCATTTATTAAAATAG | EcoRV |
| Forward adh | CATTGATATCATGTCTAACCGTTTGGATGG | EcoRV |
| Reverse adh | CATACTGCAGCTATTGAGCAGTGTAGCCAC | PstI |

Product: 1,3-Propanediol

| | | |
|---|---|---|
| Forward gpd | AAATCTCGAGTCAGTGGAGACAATAGTCG | XhoI |
| Reverse gpd | AAATATCGATATGCGTAATTTCCCAGAAATC | ClaI |
| Forward dhak | CATAAAGCTTATGAAATTCTATACTTCAACGACAG | HindIII |
| Reverse dhak | AAATGATATCTTACCAGGCGAAAGCTC | EcoRV |
| Forward Gl dehydr | AAATATCGATTTATTCAATGGTGTCAGGCTG | ClaI |
| Reverse Gl dehydr | CCAAAAGCTTATGAAAAGATCAAAACGATTTG | HindIII |
| Forward oxidoreductase | GGGTGATATCTTAAGGTAAAGTAAAGTCAACCCAC | EcoRV |
| Reverse oxidoreductase | AAATGAATTCATGTTAAACGGCCTGAAAC | EcoRI |

Lactic acid-II set of primers

| | | |
|---|---|---|
| Forward HomologyI | AAATGGTACCGAACTGAGATTAGCCCCGGAC | KpnI |
| Reverse HomologyI | GTTGTTTATCAGCCATACCAGGACATCCGACTTG | |
| Reverse for ldh | CTGCGTGCAATCCATCTTGTTCAATCATTTAGTTTTTAACTGCAGAAGCAAATTC | |
| Reverse for KAN | GCAAAAAAATGACCCGGTCACTCAGAAGAACTCGTCAAGAAGG | |
| Reverse for HomologyII | AAATTCTAGATAACTGCGGTAGCACTAAAGCCGCTGCCTTAC | XbaI |

Ethanol-II set of primers

| | | |
|---|---|---|
| Forward HomologyI | AAATGGTACCGAACTGAGATTAGCCCCGGAC | KpnI |
| Reverse HomologyII | GATTAAAGCACCTATTGTCACCAGGACATCCGACTTG | |
| Reverse pdc | CTACCTTACCATCCAAACGGTTAGACATAGGTGTAAAATACCATTTATTAAAATAG | |

TABLE 3-continued list of all primers used

| | | |
|---|---|---|
| Reverse adh | CAATCCATCTTGTTCAATCATCTATTGAGCAGTGTAGCCACCGTC | |
| Reverse KAN | GCAAAAAATGACCCGGTCACTCAGAAGAACTCGTCAAGAAGG | |
| Reverse HomologyII | AAATTCTAGATAACTGCGGTAGCACTAAAGCCGCTGCCTTAC | XbaI |

1,3-Propanediol

| | | |
|---|---|---|
| Forward HomologyI | AAATGGTACCGAACTGAGATTAGCCCCGGAC | KpnI |
| Reverse HomologyI | TATTGTCTCCACTGAACCAGGACATCCGACTTG | |
| Reverse dhg | CTGTCGTTGAAGTATAGAATTTCATATGCGTAATTTCCCAGAAATCCAAAATACG | |
| Reverse dha k | GGTTCAGCCTGACACCATTGAATAATTACCAGGCGAAAGCTCCAGTTGGAGC | |
| Reverse glycerol dehydrts | GTGGTTGACTTTACTTTACCTTAAATGAAAAGATCAAAACGATTTGCAGTACTGG | |
| Reverse oxidored | CAATCCATCTTGTTCAATCATATGTTAAACGGCCTGAAACC | |
| Reverse KAN | GCAAAAAATGACCCGGTCACTCAGAAGAACTCGTCAAGAAGG | |
| Reverse HomologyII | AAATTCTAGATAACTGCGGTAGCACTAAAGCCGCTGCCTTAC | XbaI |

Ethylene

| | | |
|---|---|---|
| Forward Efe | TAAAGTCGACAAGGAGACTAGCATGACCAAC | SalI |
| Reverse Efe | TAAAGAATTCTTAGGAGCCGGTGG | EcoRI |

2-Butanol (Clostridium)

| | |
|---|---|
| forward thl | AAGGAGATTCCAATGAGAGATGTAGTAATAGTAAG |
| reverse thl | TTAGTCTCTTTCAACTACGAGAGCTGTTCCCTG |
| forward 3bdh | AAGGAGATTCCAATGAAAAAGGTATGTGTTATAG |
| reverse 3bdh | TTATTTTGAATAATCGTAGAAACCTTTTCCTG |
| forward crt-etf | AAGGAGATTCCAATGTCAAAAGAGATTTATGAATCAG |
| reverse crt-etf | CTACAATTTTTTTACCAAATTCAAAAACATTCC |
| forward ald | AAGGAGATTCCAATGGATTTTAATTTAACAAGAG |
| reverse ald | TTATCTAAAAATTTTCCTGAAATAACTAATTTTCTGAACTTC |
| forward bdh | AAGGAGATTCCAATGCTAAGTTTTGATTATTCAATAC |
| reverse bdh | TTAATATGATTTTTTAAATATCTCAAGAAGCATCCTCTG |

2-Butanol (*L. lactis* and *K. pneumoniae*)

| | |
|---|---|
| Foreward *L. lactis* als | AAGGAGACTACTATGTCTGAGAAACAATTTGGGGC |
| Reverse *L. lactis* als | TCAGTAAAATTCTTCTGGCAAT |
| Foreward *L. lactis* aldB | AAGGAGACTACTATGTCAGAAATCACACAACTTTTTCA |
| Reverse *L. lactis* aldB | TCATTCAGCTACATCAATATCTTTTTTCAAAGC |

TABLE 3-continued list of all primers used

| | |
|---|---|
| Foreward *L. lactis* butA | AAGGAGACTACTATGTCTAAAGTTGCAGCAGTTACTGG |
| Reverse *L. lactis* butA | TTAATGAAATTGCATTCCACCATC |
| Foreward *L. lactis* butB | AAGGAGACTACTGTGGCTTGGTGTGGAATCTGT |
| Reverse *L. lactis* butB | TTATAGACCTTTTCCAGTTGGTG |
| Foreward *K. pneumoniae* dhaB | AAGGAGACTACTATGAAAAGATCAAAACGATTTGCAG |
| Reverse *K. pneumoniae* dhaB | TCAGAATGCCTGGCGGAAAAT |
| Foreward *K. pneumoniae* dhaT | AAGGAGACTACTATGAGCTATCGTATGTTTGATTATCTGG |
| Reverse *K. pneumoniae* dhaT | TCAGAATGCCTGGCGGAAAAT |

Acetone

| | |
|---|---|
| Foreward thl | AAGGAGATTCCAATGAGAGATGTAGTAATAGTAAG |
| Reverse thl | TTAGTCTCTTTCAACTACGAGAGCTGTTCCCTG |
| Foreward ctfAB | AAGGAGGCGGCGATGAACTCTAAAATAATTAG |
| Reverse ctfAB | TTATGCAGGCTCCTTTACTATATAAT |
| Foreward adc | AAGGAGGCGGCGATGTTAAAGGATGAAGTA |
| Reverse adc | CCCTTACTTAAGATAATCATATATAACTTCAGC |

Propanol

| | |
|---|---|
| Foreward thl | AAGGAGATTCCAATGAGAGATGTAGTAATAGTAAG |
| Reverse thl | TTAGTCTCTTTCAACTACGAGAGCTGTTCCCTG |
| Foreward ctfAB | AAGGAGGCGGCGATGAACTCTAAAATAATTAG |
| Reverse ctfAB | TTATGCAGGCTCCTTTACTATATAAT |
| Foreward adc | AAGGAGGCGGCGATGTTAAAGGATGAAGTA |
| Reverse adc | CCCTTACTTAAGATAATCATATATAACTTCAGC |
| Foreward *K. pneumoniae* aad | AAGGAGAATTCCAATGCATACCTTTTCTCTGC |
| Reverse *K. pneumoniae* aad | TCATTGCAGGTTCTCCAGCAGTTGC |

REFERENCES

[1] Aichi, M., Takatani N., Omata T. (2001) Role of NtcB in activation of Nitrate assimilation Genes in the Cyanobacterium *Synechocystis* sp. Strain PCC6803. *J. Bacteriol.* 183, 5840-5847

[2] Gillor, O., Harush, A., Post, A. F., Belkin, S. (2003) A *Synechococcus* PglnA::luxAB fusion for estimation of nitrogen bioavailability to freshwater cyanobacteria. *Appl. Environm. Microbiol.* 69, 1465-1474

[3] Osanai, T., Imamura, S., Asayama, M., Shirai, M., Suzuki, I., Murata, N., Tanaka, K, (2006) Nitrogen induction of sugar catabolic gene expression in *Synechocystis* sp. PCC 6803. *DNA Research* 13, 185-195

---

The invention claimed is:

1. A process of producing 1,3-propanediol compound, comprising:
feeding carbon dioxide to a culture of Cyanobacterial cells; and
subjecting the culture to light,
wherein the cell expresses a nucleic acid molecule and expression of the nucleic acid molecule confers an ability to convert a glycolytic intermediate into 1,3-propanediol, wherein said nucleic acid molecule is under the control of a regulatory system which responds to a change in the concentration of a nutrient in said culture, wherein the glycolytic intermediate is hydroxypropionaldehyde, wherein said nucleic acid molecule encodes an enzyme that converts glyceraldehyde-3-phosphate to 1,3-propanediol, wherein said enzyme is glycerol dehydratase, and wherein the glycerol dehydratase has an amino acid sequence that is at least 95% identical to SEQ ID NO: 31 or is encoded by a polynucleotide sequence that is at least 95% identical to SEQ ID NO: 32.

2. The process of claim 1, wherein said enzyme is not sensitive to oxygen inactivation.

3. The process of claim 1, wherein the regulatory system responds to a change in the concentration of the nutrient ammonium in said culture.

4. The process of claim 1, wherein the 1,3-propanediol compound or glycolytic intermediate is separated from the culture.

5. A Cyanobacterial cell that expresses a nucleic acid molecule, wherein expression of the nucleic acid molecule allows the Cyanobacterial cell to convert a glycolytic intermediate into 1,3-propanediol, wherein the nucleic acid molecule is under the control of a regulatory system which responds to a change in the concentration of a nutrient when culturing said Cyanobacterial cell, wherein the glycolytic intermediate is hydroxypropionaldehyde, wherein said nucleic acid molecule encodes an enzyme that converts glyceraldehyde-3-phosphate to 1,3-propanediol, wherein said enzyme is a glycerol dehydratase, and wherein the glycerol dehydratase has an amino acid sequence that is at least 95% identical to SEQ ID NO: 31 or is encoded by a polynucleotide sequence that is at least 95% identical to SEQ ID NO: 32.

6. The Cyanobacterial cell of claim 5, wherein the regulatory system responds to a change in the concentration of the nutrient ammonium.

7. The process of claim 1, wherein the Cyanobacterial cell is obtained from a *Synechocystis* cell.

8. The process of claim 1, wherein the Cyanobacterial cell is obtained from a *Synechocystis* PCC 6083 cell.

9. The Cyanobacterial cell of claim 5, wherein the Cyanobacterial cell is obtained from a *Synechocystis* cell.

10. The Cyanobacterial cell of claim 5, wherein the Cyanobacterial cell is obtained from a *Synechocystis* PCC 6083 cell.

11. The process of claim 1, wherein the nucleic acid molecule comprised in the cell is integrated into its genome by homologous recombination.

12. The Cyanobacterial cell of claim 5, wherein the nucleic acid molecule comprised in the Cyanobacterial cell is integrated into its genome by homologous recombination.

* * * * *

SEQUENCE LISTING

```
<160> NUMBER OF SEQ ID NOS: 135

<210> SEQ ID NO 1
<211> LENGTH: 552
<212> TYPE: PRT
<213> ORGANISM: Sarcina ventriculi

<400> SEQUENCE: 1

Met Lys Ile Thr Ile Ala Glu Tyr Leu Leu Lys Arg Leu Lys Glu Val
1               5                   10                  15

Asn Val Glu His Met Phe Gly Val Pro Gly Asp Tyr Asn Leu Gly Phe
            20                  25                  30

Leu Asp Tyr Val Glu Asp Ser Lys Asp Ile Glu Trp Val Gly Ser Cys
        35                  40                  45

Asn Glu Leu Asn Ala Gly Tyr Ala Ala Asp Gly Tyr Ala Arg Leu Arg
    50                  55                  60

Gly Phe Gly Val Ile Leu Thr Thr Tyr Gly Val Gly Ser Leu Ser Ala
65                  70                  75                  80

Ile Asn Ala Thr Thr Gly Ser Phe Ala Glu Asn Val Pro Val Leu His
                85                  90                  95

Ile Ser Gly Val Pro Ser Ala Leu Val Gln Asn Arg Lys Leu Val
            100                 105                 110

His His Ser Thr Ala Arg Gly Glu Phe Asp Thr Phe Glu Arg Met Phe
        115                 120                 125

Arg Glu Ile Thr Glu Phe Gln Ser Ile Ile Ser Glu Tyr Asn Ala Ala
    130                 135                 140

Glu Glu Ile Asp Arg Val Ile Glu Ser Ile Tyr Lys Tyr Gln Leu Pro
145                 150                 155                 160

Gly Tyr Ile Glu Leu Pro Val Asp Ile Val Ser Lys Glu Ile Glu Ile
                165                 170                 175

Asp Glu Met Lys Pro Leu Asn Leu Thr Met Arg Ser Asn Glu Lys Thr
            180                 185                 190

Leu Glu Lys Phe Val Asn Asp Val Lys Glu Met Val Ala Ser Ser Lys
        195                 200                 205

Gly Gln His Ile Leu Ala Asp Tyr Glu Val Leu Arg Ala Lys Ala Glu
    210                 215                 220

Lys Glu Leu Glu Gly Phe Ile Asn Glu Ala Lys Ile Pro Val Asn Thr
225                 230                 235                 240

Leu Ser Ile Gly Lys Thr Ala Val Ser Glu Ser Asn Pro Tyr Phe Ala
                245                 250                 255

Gly Leu Phe Ser Gly Glu Thr Ser Ser Asp Leu Val Lys Glu Leu Cys
            260                 265                 270

Lys Ala Ser Asp Ile Val Leu Leu Phe Gly Val Lys Phe Ile Asp Thr
        275                 280                 285

Thr Thr Ala Gly Phe Arg Tyr Ile Asn Lys Asp Val Lys Met Ile Glu
    290                 295                 300

Ile Gly Leu Thr Asp Cys Arg Ile Gly Glu Thr Ile Tyr Thr Gly Leu
```

```
                305                 310                 315                 320
Tyr Ile Lys Asp Val Ile Lys Ala Leu Thr Asp Ala Lys Ile Lys Phe
                    325                 330                 335

His Asn Asp Val Lys Val Glu Arg Glu Ala Val Glu Lys Phe Val Pro
                    340                 345                 350

Thr Asp Ala Lys Leu Thr Gln Asp Arg Tyr Phe Lys Gln Met Glu Ala
                    355                 360                 365

Phe Leu Lys Pro Asn Asp Val Leu Val Gly Glu Thr Gly Thr Ser Tyr
            370                 375                 380

Ser Gly Ala Cys Asn Met Arg Phe Pro Glu Gly Ser Ser Phe Val Gly
385                 390                 395                 400

Gln Gly Ser Trp Met Ser Ile Gly Tyr Ala Thr Pro Ala Val Leu Gly
                    405                 410                 415

Thr His Leu Ala Asp Lys Ser Arg Arg Asn Ile Leu Leu Ser Gly Asp
                    420                 425                 430

Gly Ser Phe Gln Leu Thr Val Gln Glu Val Ser Thr Met Ile Arg Gln
                    435                 440                 445

Lys Leu Asn Thr Val Leu Phe Val Val Asn Asn Asp Gly Tyr Thr Ile
            450                 455                 460

Glu Arg Leu Ile His Gly Pro Glu Arg Glu Tyr Asn His Ile Gln Met
465                 470                 475                 480

Trp Gln Tyr Ala Glu Leu Val Lys Thr Leu Ala Thr Glu Arg Asp Ile
                    485                 490                 495

Gln Pro Thr Cys Phe Lys Val Thr Thr Glu Lys Glu Leu Ala Ala Ala
                    500                 505                 510

Met Glu Glu Ile Asn Lys Gly Thr Glu Gly Ile Ala Phe Val Glu Val
                    515                 520                 525

Val Met Asp Lys Met Asp Ala Pro Lys Ser Leu Arg Gln Glu Ala Ser
            530                 535                 540

Leu Phe Ser Ser Gln Asn Asn Tyr
545                 550

<210> SEQ ID NO 2
<211> LENGTH: 3244
<212> TYPE: DNA
<213> ORGANISM: Sarcina ventriculi

<400> SEQUENCE: 2
ataactcgag gacaataggt gctttaatca ctgaattttc gggaataatg ggtgttggat      60
tattatttgg agtatcgaaa tggattacag taccacttgc ggttgcagct cttatattat     120
taagtgttac tggaaaatac aaagtggtcg aaagagttgc cattgtagtt ggggcttttg     180
aacttgtatt tatacctgct atgatatttg ccaaaccaga ttatacatct gttatgatga     240
gtttagttgg aagccaacct ttaaatagtt cagcttattg gttaatgatt tctgcaaatg     300
taggagcagt tataatgcct tggatggtat tttatcaaca aggtgcagta gtggataaag     360
gattaacaga aaaaaatctt aaagcaagta gaatagatac cattttcggt tcaataataa     420
cacaacttat atgttgtgta gtaattatag cggttgcagc gacaatagga atgaaagacc     480
caaatgcatc acttaataca gtacaacaaa ttagtcaagc tttaacacca ttttaggcg      540 catagacagg aaaaatacta tttgcagttg gacttacagg tgcagcgctg gttgcagcta     600
tagttgttac attagcctct tcatggggat tggagaaat atttaaaaaa ccatctagct      660
taaattgcaa atggagtgaa gcacctgcat tttatatatt ttatagtacg cttttaataa     720
```

```
tagctggaat tatagtattg tcaggaattc cattagtacc attaacatta ggtgttgaaa      780
ttttaaatac agttcttctt ccgatagttt taggcttttt gatagctttg gcttggaaag      840
ttctacctaa aaagcatgct ttacatttgt gggaaaaaat aattttaatc attatatata      900
tcgttataac agtgttagga gtgcttacct tatatttaac attctaaata taaagttaat      960
agaaatagac tacattaaac ttttatttaa atgtagtcta ttttattatt taaaataatc     1020
tgaatatttt aaataagatg ataagagtgt atcttatgaa taaactatat tttatgaata     1080
aaatgatagt attgtaaaaa aagaaaatt tacgatagac agagaaaata agatttgtaa      1140
acgctaaaaa tttaaaaata acatcagata aatcgtttat attaattttt actaaaagct     1200
atttaaaggt gtattatata tacatagttt atcttataaa taaaaatga attggaggaa      1260 atacataatg aaaataacaa ttgcagaata cttattaaaa agattaaaag aagtaaatgt     1320
agagcatatg tttggagttc ctggagatta taacttagga ttttagatt atgttgaaga     1380 ttctaaagat attgaatggg ttggaagctg taatgaactt aatgcaggat atgcagcaga     1440
tggatatgca agacttagag gatttggtgt aatacttaca acttatggag ttggttcact     1500
tagtgcaata aatgctacaa caggttcatt tgcagaaaat gttccagtat tacatatatc     1560
aggtgtacca tcagctttag ttcaacaaaa cagaaagcta gttcaccatt caactgctag     1620
aggagaattc gacactttg aaagaatgtt tagagaaata acagaatttc aatcaatcat      1680
aagcgaatat aatgcagctg aagaaatcga tagagttata gaatcaatat ataaatatca     1740
attaccaggt tatatagaat taccagttga tatagtttca aaagaaatag aaatcgacga     1800
aatgaaaccg ctaaacttaa ctatgagaag caacgagaaa actttagaga aattcgtaaa     1860
tgatgtaaaa gaaatggttg caagctcaaa aggacaacat attttagctg attatgaagt     1920
attaagagct aaagctgaaa aagaattaga aggatttata aatgaagcaa aaatcccagt     1980
aaacacttta agtataggaa agacagcagt atcagaaagc aatccatact ttgctggatt     2040
attctcagga gaaactagtt cagatttagt taaagaactt tgcaaagctt ctgatatagt     2100
tttactattt ggagttaaat tcatagatac tacaacagct ggatttagat atataaataa     2160
agatgttaaa atgatagaaa ttggtttaac tgattgtaga attggagaaa ctatttatac     2220
tggactttac attaaagatg ttataaaagc tttaacagat gctaaaataa aattccataa     2280
cgatgtaaaa gtagaaagag aagcagtaga aaaatttgtt ccaacagatg ctaaattaac     2340
tcaagataga tatttcaaac aaatggaagc gttcttaaaa cctaatgatg tattagttgg     2400
tgaaacagga acatcatata gtggagcatg taatatgaga ttcccagaag gatcaagctt     2460
tgtaggtcaa ggatcttgga tgtcaattgg atatgctact cctgcagttt taggaactca     2520
tttagctgat aagagcagaa gaaacattct tttaagtggt gatggttcat tccaattaac     2580
agttcaagaa gtttcaacaa tgataagaca aaaattaaat acagtattat tgtagttaa     2640 caatgatgga tatacaattg aaagattaat ccacggacct gaaagagaat ataaccatat     2700
tcaaatgtgg caatatgcag aacttgtaaa aacattagct actgaaagag atatacaacc     2760
aacttgtttc aaagttacaa ctgaaaaaga attagcagct gcaatggaag aaataaacaa     2820
aggaacagaa ggtattgctt tgttgaagt agtaatggat aaaatggatg ctccaaaatc     2880
attaagacaa gaagcaagtc tatttagttc tcaaaataac tactaatata tattatatat     2940
aaataaaaat taaaaagatt gtaaattaaa tttaaaggtg acttctatta atagaggtca     3000 tcttttatg cttataagtt taattttata aaatacaatt agtaattaaa cactttataa      3060
gaaaaaatta atctttattt gaaaagttaa ttgtataatt ataaaataag ctattttat      3120
```

```
ttaataataa atgggaggag ttcatatgcc ttatacatta ttaattaaca aagaggaatt    3180
acgaggtttt ttatatgagg ataaatctat tttaataaat ggtattttac acctgatatc    3240
gtcg                                                                3244
```

<210> SEQ ID NO 3
<211> LENGTH: 252
<212> TYPE: PRT
<213> ORGANISM: Lactobacillus brevis

<400> SEQUENCE: 3

```
Met Ser Asn Arg Leu Asp Gly Lys Val Ala Ile Ile Thr Gly Gly Thr
1               5                   10                  15

Leu Gly Ile Gly Leu Ala Ile Ala Thr Lys Phe Val Glu Glu Gly Ala
            20                  25                  30

Lys Val Met Ile Thr Gly Arg His Ser Asp Val Gly Glu Lys Ala Ala
        35                  40                  45

Lys Ser Val Gly Thr Pro Asp Gln Ile Gln Phe Gln His Asp Ser
    50                  55                  60

Ser Asp Glu Asp Gly Trp Thr Lys Leu Phe Asp Ala Thr Glu Lys Ala
65                  70                  75                  80

Phe Gly Pro Val Ser Thr Leu Val Asn Asn Ala Gly Ile Ala Val Asn
                85                  90                  95

Lys Ser Val Glu Glu Thr Thr Thr Ala Glu Trp Arg Lys Leu Leu Ala
            100                 105                 110

Val Asn Leu Asp Gly Val Phe Phe Gly Thr Arg Leu Gly Ile Gln Arg
        115                 120                 125

Met Lys Asn Lys Gly Leu Gly Ala Ser Ile Ile Asn Met Ser Ser Ile
    130                 135                 140

Glu Gly Phe Val Gly Asp Pro Ser Leu Gly Ala Tyr Asn Ala Ser Lys
145                 150                 155                 160

Gly Ala Val Arg Ile Met Ser Lys Ser Ala Ala Leu Asp Cys Ala Leu
                165                 170                 175

Lys Asp Tyr Asp Val Arg Val Asn Thr Val His Pro Gly Tyr Ile Lys
            180                 185                 190

Thr Pro Leu Val Asp Asp Leu Pro Gly Ala Glu Glu Ala Met Ser Gln
        195                 200                 205

Arg Thr Lys Thr Pro Met Gly His Ile Gly Glu Pro Asn Asp Ile Ala
    210                 215                 220

Tyr Ile Cys Val Tyr Leu Ala Ser Asn Glu Ser Lys Phe Ala Thr Gly
225                 230                 235                 240

Ser Glu Phe Val Val Asp Gly Gly Tyr Thr Ala Gln
                245                 250
```

<210> SEQ ID NO 4
<211> LENGTH: 779
<212> TYPE: DNA
<213> ORGANISM: Lactobacillus brevis

<400> SEQUENCE: 4

```
cattgatatc atgtctaacc gtttggatgg taaggtagca atcattacag gtggtacgtt     60
gggtatcggt ttagctatcg ccacgaagtt cgttgaagaa ggggctaagg tcatgattac    120
cggccggcac agcgatgttg gtgaaaaagc agctaagagt gtcggcactc ctgatcagat    180 tcaattttc caacatgatt cttccgatga agacggctgg acgaaattat tcgatgcaac    240
```

-continued

```
ggaaaaagcc tttggcccag tttctacatt agttaataac gctgggatcg cggttaacaa    300
gagtgtcgaa gaaaccacga ctgctgaatg gcgtaaatta ttagccgtca accttgatgg    360
tgtcttcttc ggtacccgat tagggattca acggatgaag aacaaaggct tagggggcttc   420
catcatcaac atgtcttcga tcgaaggctt tgtgggtgat cctagcttag ggcttacaa     480
cgcatctaaa ggggccgtac ggattatgtc caagtcagct gccttagatt gtgccctaaa    540
ggactacgat gttcgggtaa acactgttca ccctggctac atcaagacac cattggttga    600
tgacctacca ggggccgaag aagcgatgtc acaacggacc aagacgccaa tgggccatat    660
cggtgaacct aacgatattg cctacatctg tgtttacttg gcttctaacg aatctaaatt    720
tgcaacgggt tctgaattcg tagttgacgg tggctacact gctcaatagc tgcagtatg    779
```

<210> SEQ ID NO 5
<211> LENGTH: 392
<212> TYPE: PRT
<213> ORGANISM: Clostridium acetobutylicum

<400> SEQUENCE: 5

```
Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125

Arg Trp Gly Gln Arg Met Gly Asp Ser Glu Leu Val Asp Glu Met Ile
    130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285
```

```
Gly Tyr Gly Ala Phe Tyr Ala Thr Lys Ala Ala Leu Asp Lys Ile Asn
    290             295                 300
Leu Lys Pro Glu Asp Leu Asp Leu Ile Glu Ala Asn Glu Ala Tyr Ala
305             310                 315                 320
Ser Gln Ser Ile Ala Val Thr Arg Asp Leu Asn Leu Asp Met Ser Lys
            325                 330                 335
Val Asn Val Asn Gly Ala Ile Ala Leu Gly His Pro Ile Gly Ala
            340                 345                 350
Ser Gly Ala Arg Ile Leu Val Thr Leu Leu Tyr Ala Met Gln Lys Arg
        355                 360                 365
Asp Ser Lys Lys Gly Leu Ala Thr Leu Cys Ile Gly Gly Gly Gln Gly
    370                 375                 380
Thr Ala Leu Val Val Glu Arg Asp
385                 390

<210> SEQ ID NO 6
<211> LENGTH: 1179
<212> TYPE: DNA
<213> ORGANISM: Clostridium acetobutylicum

<400> SEQUENCE: 6
```

| | | | | |
|---|---|---|---|---|
| ttagtctctt tcaactacga gagctgttcc ctgacctcca ccaatacata gagtagcaag | 60 |
| accttttttt gaatctcttt tttgcatagc gtatagtaat gttactaaaa tacgtgcacc | 120 |
| agatgcacct attggatgtc caagtgctat agctccacca ttaacattaa ctttactcat | 180 |
| atctaaattt aaatctctag ttactgctat actttgagaa gcatatgcct cgttagcttc | 240 |
| aattaaatct aagtcttcag gttttaaatt aattttatct aaggcagctt tagttgcata | 300 |
| aaaagctcca tatcccatta tgatggatc taccccatat gatccgtaag aagtaatctt | 360 |
| agcaagtggt tttattccga gagcgttagc tttatcagcg ctcattatta ctagtgctgc | 420 |
| agctccatca tttaatccgg atgcattacc tgctgtaaca gtaccatttt ccttgaaaat | 480 |
| aggtttaagt tttcttaatg cttcaatagt gtttccgaat ctaggaaatt catcttgatc | 540 |
| aaagactatt tcaccttttt tagtctttat taatacagga actatttcat ccttaaattc | 600 |
| tccatttta atggcttttt cagcttttg ttgtgacata agtgaaaatt catcttgctc | 660 |
| ttctcttgtt atattccatt gttctgcaat attttctgca gttactccca tatgatatcc | 720 |
| attaaatgca tcccacaaac catcctttat catttcatca actaattcac tatctcccat | 780 |
| tctttgaccc catctctgat tgttaatcaa atatggtgat ctagacatat tttccatacc | 840 |
| acctactaca atggtatcag catctccagc tttatatt tgagctgcta aacttataga | 900 |
| tcttaaacct gaaccacaaa ccttattgat tgtaaacgca ggtgtttcta aaggtaatcc | 960 |
| tgctttact gctgcttgtc ttgctgggtt ttggcctaat ccagcttgaa gtacatttcc | 1020 |
| aaaaataact tcattaatct catttggatt tatattagct cttcttacag cttcctttat | 1080 |
| tactatagct cctaactctg ttgcaggtac atcctttaat gttttcccat atgctcctat | 1140 |
| tgcagttctt acagcactta ctattactac atctctcat | 1179 |

```
<210> SEQ ID NO 7
<211> LENGTH: 244
<212> TYPE: PRT
<213> ORGANISM: Clostridium acetobutylicum

<400> SEQUENCE: 7

Met Leu Lys Asp Glu Val Ile Lys Gln Ile Ser Thr Pro Leu Thr Ser
```

```
              1               5                   10                  15
            Pro Ala Phe Pro Arg Gly Pro Tyr Lys Phe His Asn Arg Glu Tyr Phe
                         20                  25                  30

Asn Ile Val Tyr Arg Thr Asp Met Asp Ala Leu Arg Lys Val Val Pro
                         35                  40                  45

Glu Pro Leu Glu Ile Asp Pro Leu Val Arg Phe Glu Ile Met Ala
                 50              55                  60

Met His Asp Thr Ser Gly Leu Gly Cys Tyr Thr Glu Ser Gly Gln Ala
             65                  70                  75                  80

Ile Pro Val Ser Phe Asn Gly Val Lys Gly Asp Tyr Leu His Met Met
                             85                  90                  95

Tyr Leu Asp Asn Glu Pro Ala Ile Ala Val Gly Arg Glu Leu Ser Ala
                         100                 105                 110

Tyr Pro Lys Lys Leu Gly Tyr Pro Lys Leu Phe Val Asp Ser Asp Thr
                         115                 120                 125

Leu Val Gly Thr Leu Asp Tyr Gly Lys Leu Arg Val Ala Thr Ala Thr
                         130                 135                 140

Met Gly Tyr Lys His Lys Ala Leu Asp Ala Asn Glu Ala Lys Asp Gln
            145                 150                 155                 160

Ile Cys Arg Pro Asn Tyr Met Leu Lys Ile Ile Pro Asn Tyr Asp Gly
                             165                 170                 175

Ser Pro Arg Ile Cys Glu Leu Ile Asn Ala Lys Ile Thr Asp Val Thr
                         180                 185                 190

Val His Glu Ala Trp Thr Gly Pro Thr Arg Leu Gln Leu Phe Asp His
                         195                 200                 205

Ala Met Ala Pro Leu Asn Asp Leu Pro Val Lys Glu Ile Val Ser Ser
                         210                 215                 220

Ser His Ile Leu Ala Asp Ile Ile Leu Pro Arg Ala Glu Val Ile Tyr
            225                 230                 235                 240

Asp Tyr Leu Lys

<210> SEQ ID NO 8
<211> LENGTH: 735
<212> TYPE: DNA
<213> ORGANISM: Clostridium acetobutylicum

<400> SEQUENCE: 8
ttacttaaga taatcatata taacttcagc tctaggcaat attatatctg caagaatgtg      60
agagctagaa acaatctctt ttactggcaa atcattaagt ggcgccatag cgtgatcaaa     120
taactgcagt cgagttggtc ctgtccaagc ttcatgtacg gtaacatctg tgattttcgc     180
atttataagc tcacatattc tagggcttcc atcataattg gtattatttt caacatata      240 attagggcga caaatttgat cctttgcttc attagcatct aaggctttat gtttgtaccc     300
cattgtagct gtcgcaactc taagttttcc atagtctaaa gttcctacta agtatctga     360 atccacaaaa agctttggat acccgagctt tttaggatat gcacttaatt cccttcctac     420
tgcaattgca ggctcattat ctaaatacat catatgaaga atctcccct taactccatt     480 aaagcttacg ggaatagcct gtccgctttc tgtataacaa ccaagtccac tcgtatcatg     540
cattgccata atttcaaacc tgactaaggg ctcatcaatt tctaaaggct ctggcacaac     600
tttacgaagt gcatccatat ctgtacgata caatgttaaa aatactcac gattatgaaa     660 tttatagggt cctctaggaa atgcaggcga agttaatggc gtgctaattt gtttaattac     720
ttcatccttt aacat                                                     735
```

<210> SEQ ID NO 9
<211> LENGTH: 370
<212> TYPE: PRT
<213> ORGANISM: Klebsiella pneumoniae

<400> SEQUENCE: 9

```
Met His Thr Phe Ser Leu Gln Thr Arg Leu Tyr Ser Gly Pro Gly Ser
1               5                   10                  15

Leu Ala Ala Leu Gln Arg Phe Ser His Gln His Ile Trp Ile Val Cys
            20                  25                  30

Asp Gly Phe Leu Ala Arg Ser Pro Leu Leu Asp Arg Leu Arg Ala Ala
        35                  40                  45

Leu Pro Ala Ser Asn Arg Val Ser Val Phe Ser Asp Ile Thr Pro Asp
    50                  55                  60

Pro Thr Ile His Thr Val Ala Lys Gly Ile Ala Gln Met Gln Thr Leu
65                  70                  75                  80

Arg Pro Gln Val Val Ile Gly Phe Gly Gly Ser Ala Met Asp Ala
                85                  90                  95

Ala Lys Ala Ile Val Trp Phe Ser Gln Gln Gly Gly Leu Pro Val Asp
            100                 105                 110

Thr Cys Val Ala Ile Pro Thr Thr Ser Gly Thr Gly Ser Glu Val Thr
        115                 120                 125

Ser Ala Cys Val Ile Ser Asp Pro Glu Lys Gly Ile Lys Tyr Pro Leu
    130                 135                 140

Phe His Glu Ala Leu Cys Pro Asp Met Ala Ile Ile Asp Pro Thr Leu
145                 150                 155                 160

Val Val Ser Val Pro Pro Thr Ile Thr Ala His Thr Gly Leu Asp Ala
                165                 170                 175

Leu Thr His Ala Leu Glu Ala Trp Val Ser Pro Gln Ala Thr Asp Phe
            180                 185                 190

Thr Asp Ala Leu Ala Glu Lys Ala Ala Arg Leu Val Phe Arg Ala Leu
        195                 200                 205

Pro Val Ala Ile Arg Gln Gly Asp Cys Ile Ala Thr Arg Ser Lys Met
    210                 215                 220

His Asn Ala Ser Thr Leu Ala Gly Met Ala Phe Ser Gln Ala Gly Leu
225                 230                 235                 240

Gly Leu Asn His Ala Ile Ala His Gln Leu Gly Gly Gln Phe His Leu
                245                 250                 255

Pro His Gly Leu Ala Asn Ala Leu Leu Leu Thr Ala Val Ile Arg Phe
            260                 265                 270

Asn Ala Gly Glu Pro Arg Ala Ala Lys Arg Tyr Ala Arg Leu Ala Arg
        275                 280                 285

Ala Cys Arg Phe Cys Pro Pro Ala Gly Glu Gln Glu Ala Phe Gln
    290                 295                 300

Ala Leu Leu Thr Ala Val Glu Thr Leu Lys Gln Gln Cys Ala Ile Pro
305                 310                 315                 320

Pro Leu Lys Gly Ala Leu Gln Glu Lys Tyr Pro Leu Phe Leu Ser Arg
                325                 330                 335

Ile Pro Ala Met Val Pro Ala Ala Leu Ala Asp Ala Thr Leu Arg Thr
            340                 345                 350

Asn Pro Arg Pro Val Asp Gly Ala Ala Ile Ala Gln Leu Leu Glu Asn
        355                 360                 365

Leu Gln
```

<210> SEQ ID NO 10
<211> LENGTH: 1113
<212> TYPE: DNA
<213> ORGANISM: Klebsiella pneumoniae

<400> SEQUENCE: 10

```
atgcatacct tttctctgca aacgcgcctc tacagcggcc cgggcagcct ggccgcgctg      60
cagcgcttta gccatcagca catctggatc gtctgcgacg gcttcctggc gcgctcgccg     120
ctgcttgacc gactgcgcgc cgcgctgccc gccagcaacc gcgtcagcgt gttcagcgat     180
attacaccgg atccgaccat tcacaccgtg gcgaaaggga tagcgcagat gcagaccctg     240
cgtccgcagg tggtgatcgg cttcggcggc ggctcggcga tggatgccgc caaggctatc     300
gtctggttca gccagcaggg cggtctgcct gttgacacct cgtggcgat ccccaccacc     360
agcggtaccg gttcggaagt gaccagcgcc tgcgtcatca gcacccggga aaaagggatc     420
aagtacccgc tgttccatga ggcgctctgt cccgacatgg cgatcatcga cccgacgctg     480
gtggttagcg taccgcccac catcacagcc cataccgggc tggacgcgct gacccacgcc     540
ctggaggcat gggtctcgcc gcaggccacc gattttaccg atgcgctggc ggaaaaggcc     600
gccaggctgg tgtttcgcgc cctgcccgtt gcgattcgtc agggcgactg cattgcgacc     660
cgcagcaaaa tgcacaatgc atcaaccctc gccggtatgg cctttagcca ggctggcctt     720
gggctcaatc atgcgatcgc ccatcagctt ggcggccagt tcacctcccc catggcctg    780
gccaatgcgc tgctgctgac cgcggtgatc cgcttcaatg ccggcgagcc gcgagcggct     840
aagcgctatg cgcgcctggc cagggcctgc cgcttctgcc cgcccgcagc tggcgaacag     900
gaggctttcc aggcgctgct taccgcggtg gaaacgctga acagcagtg cgccattccc     960
cccctcaagg gcgcgctgca ggaaaagtat ccccttttct tatcgcgaat cccgccatg    1020
gtgccggccg cgctggccga cgccaccctg cgcaccaacc gcgtccggt cgatggcgcg    1080
gccatcgcgc aactgctgga gaacctgcaa tga                                  1113
```

<210> SEQ ID NO 11
<211> LENGTH: 392
<212> TYPE: PRT
<213> ORGANISM: Clostridium acetobutylicum

<400> SEQUENCE: 11

```
Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
        115                 120                 125
```

Arg Trp Gly Gln Arg Met Gly Asp Ser Glu Leu Val Asp Glu Met Ile
    130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365

Asp Ser Lys Lys Gly Leu Ala Thr Leu Cys Ile Gly Gly Gly Gln Gly
    370                 375                 380

Thr Ala Leu Val Val Glu Arg Asp
385                 390

<210> SEQ ID NO 12
<211> LENGTH: 1179
<212> TYPE: DNA
<213> ORGANISM: Clostridium acetobutylicum

<400> SEQUENCE: 12
ttagtctctt tcaactacga gagctgttcc ctgacctcca ccaatacata gagtagcaag    60 acctttttt gaatctcttt tttgcatagc gtatagtaat gttactaaaa tacgtgcacc    120
agatgcacct attggatgtc caagtgctat agctccacca ttaacattaa ctttactcat   180
atctaaattt aaatctctag ttactgctat actttgagaa gcatatgcct cgttagcttc   240
aattaaatct aagtcttcag gttttaaatt aattttatct aaggcagctt tagttgcata   300
aaaagctcca tatcccatta tgatggatc taccccatat gatccgtaag aagtaatctt    360
agcaagtggt tttattccga gagcgttagc tttatcagcg ctcattatta ctagtgctgc   420
agctccatca tttaatccgg atgcattacc tgctgtaaca gtaccatttt ccttgaaaat   480
aggtttaagt tttcttaatg cttcaatagt gtttccgaat ctaggaaatt catcttgatc   540
aaagactatt tcacctttt tagtctttat taatacagga actatttcat ccttaaattc   600

-continued

```
tccattttta atggctttt  cagcttttg ttgtgacata agtgaaaatt catcttgctc    660
ttctcttgtt atattccatt gttctgcaat attttctgca gttactccca tatgatatcc    720
attaaatgca tcccacaaac catcctttat catttcatca actaattcac tatctcccat    780
tctttgaccc catctctgat tgttaatcaa atatggtgat ctagacatat tttccatacc    840
acctactaca atggtatcag catctccagc ttttataatt tgagctgcta aacttataga    900
tcttaaacct gaaccacaaa ccttattgat tgtaaacgca ggtgtttcta aaggtaatcc    960 tgctttact gctgcttgtc ttgctgggtt ttggcctaat ccagcttgaa gtacatttcc    1020
aaaaataact tcattaatct catttggatt tatattagct cttcttacag cttcctttat    1080
tactatagct cctaactctg ttgcaggtac atcctttaat gttttccat atgctcctat    1140 tgcagttctt acagcactta ctattactac atctctcat    1179
```

<210> SEQ ID NO 13
<211> LENGTH: 282
<212> TYPE: PRT
<213> ORGANISM: Clostridium acetobutylicum

<400> SEQUENCE: 13

```
Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95

Gln Ile Phe Ala Asp Leu Asp Asn Ile Cys Lys Pro Glu Thr Ile Leu
            100                 105                 110

Ala Ser Asn Thr Ser Ser Leu Ser Ile Thr Glu Val Ala Ser Ala Thr
        115                 120                 125

Lys Arg Pro Asp Lys Val Ile Gly Met His Phe Phe Asn Pro Ala Pro
    130                 135                 140

Val Met Lys Leu Val Glu Val Ile Arg Gly Ile Ala Thr Ser Gln Glu
145                 150                 155                 160

Thr Phe Asp Ala Val Lys Glu Thr Ser Ile Ala Ile Gly Lys Asp Pro
                165                 170                 175

Val Glu Val Ala Glu Ala Pro Gly Phe Val Val Asn Arg Ile Leu Ile
            180                 185                 190

Pro Met Ile Asn Glu Ala Val Gly Ile Leu Ala Glu Gly Ile Ala Ser
        195                 200                 205

Val Glu Asp Ile Asp Lys Ala Met Lys Leu Gly Ala Asn His Pro Met
    210                 215                 220

Gly Pro Leu Glu Leu Gly Asp Phe Ile Gly Leu Asp Ile Cys Leu Ala
225                 230                 235                 240

Ile Met Asp Val Leu Tyr Ser Glu Thr Gly Asp Ser Lys Tyr Arg Pro
                245                 250                 255

His Thr Leu Leu Lys Lys Tyr Val Arg Ala Gly Trp Leu Gly Arg Lys
            260                 265                 270
```

```
Ser Gly Lys Gly Phe Tyr Asp Tyr Ser Lys
        275                 280
```

<210> SEQ ID NO 14
<211> LENGTH: 849
<212> TYPE: DNA
<213> ORGANISM: Clostridium acetobutylicum

<400> SEQUENCE: 14

```
ttattttgaa taatcgtaga aaccttttcc tgattttctt ccaagccatc ctgctcttac    60
atacttctta agtaatgtat gtggtctata cttagaatct ccagtttctg agtataaaac   120
atccattata gcaagacata tatcaagacc tataaaatca cctaattcta atggtcccat   180
tgggtgatta gctccaagtt tcatagcttt atctatgtct tctactgaag ctattccttc   240
tgctaatata ccaactgctt cattaatcat tggtattaat attctattta caacaaatcc   300
tggtgcttct gctacttcta caggatcttt tcctattgct atagatgtct ctttaactgc   360
atcaaaagtt tcttgtgatg tagctattcc tcttattacc tctacaagct tcataacagg   420
agctggatta agaaatgca tacctataac cttatcaggt cttttagttg ctgatgccac   480
ttctgttatt gaaagtgatg atgtatttga tgcaagaatt gttctggct tgcatatatt    540
gtctaagtca gcaaaaatct gcttttaat atccattctt tcaacagctg cttctataac   600
taaatcgcaa tcagctgcca tattaaggtc aactgttccg gaaattctag ttaagatttc   660
aactttagta gcttcttcta tctttccttt ttaactaat ttagaaagat ttttattgat    720
aaaatctaat cctctatcaa caaattcatc tttaatatct cttaatacta cttcaaatcc   780
tttagctgca aatgcctgag caattcctga acccatagta cctgcaccta aacacatac    840
ctttttcat                                                            849
```

<210> SEQ ID NO 15
<211> LENGTH: 261
<212> TYPE: PRT
<213> ORGANISM: Clostridium acetobutylicum

<400> SEQUENCE: 15

```
Met Glu Leu Asn Asn Val Ile Leu Glu Lys Glu Gly Lys Val Ala Val
1               5                   10                  15

Val Thr Ile Asn Arg Pro Lys Ala Leu Asn Ala Leu Asn Ser Asp Thr
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
    50                  55                  60

Gly Ala Asp Ile Ser Glu Met Lys Glu Met Asn Thr Ile Glu Gly Arg
65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
        115                 120                 125

Arg Phe Gly Gln Pro Glu Val Gly Leu Gly Ile Thr Pro Gly Phe Gly
    130                 135                 140

Gly Thr Gln Arg Leu Ser Arg Leu Val Gly Met Gly Met Ala Lys Gln
145                 150                 155                 160
```

Leu Ile Phe Thr Ala Gln Asn Ile Lys Ala Asp Glu Ala Leu Arg Ile
            165                 170                 175

Gly Leu Val Asn Lys Val Val Glu Pro Ser Glu Leu Met Asn Thr Ala
        180                 185                 190

Lys Glu Ile Ala Asn Lys Ile Val Ser Asn Ala Pro Val Ala Val Lys
            195                 200                 205

Leu Ser Lys Gln Ala Ile Asn Arg Gly Met Gln Cys Asp Ile Asp Thr
        210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
            245                 250                 255

Gly Phe Lys Asn Arg
            260

<210> SEQ ID NO 16
<211> LENGTH: 786
<212> TYPE: DNA
<213> ORGANISM: Clostridium acetobutylicum

<400> SEQUENCE: 16
ctatctattt ttgaagcctt caatttttct tttctctatg aaagctgtca ttgcatcctt      60
ttgatcctct gttgaaaagc attctccaaa tgcttctgat tcaaatgcta agcagtatc     120 aatatcacac tgcattcctc tattaatagc ctgtttgctt aacttaacag ctactggagc    180
attgctcaca attttgtttg caattctctt tgctgtattc attaattcac taggttctac    240
taccttattt acaagtccga ttcttaatgc ttcatctgcc tttatatttt gtgcagtaaa    300
tataagctgc tttgccatgc ccattccaac taatcttgaa agtctttgtg taccaccaaa    360
accaggtgtt attccgagac tacttctggt tgaccaaat cttgcgttgc ttgaagctat    420
tcttatatca aagacatag ctatttcgca tccgcctcct aaagcaaaac cattaacagc     480
tgctattaca ggcttttcaa gaagttctaa tcttctaaac actttatttc caagtatccc    540
gaattttcta ccttcaatgg tattcatttc cttcatctca gaaatatctg ctcctgctac    600
aaatgatttt tctcctgctc cagttaaaat tactgcaagt acttcgctat cattttcaat    660
ttcacctata acataatcca tttcttttag tgtatcacta tttaacgcat ttaatgcttt    720
aggtctgtta atggtaacta cagcaacttt accttccttt tcaaggatga cattgtttag    780
ttccat                                                               786

<210> SEQ ID NO 17
<211> LENGTH: 379
<212> TYPE: PRT
<213> ORGANISM: Clostridium acetobutylicum

<400> SEQUENCE: 17

Met Asp Phe Asn Leu Thr Arg Glu Gln Glu Leu Val Arg Gln Met Val
1               5                   10                  15

Arg Glu Phe Ala Glu Asn Glu Val Lys Pro Ile Ala Ala Glu Ile Asp
            20                  25                  30

Glu Thr Glu Arg Phe Pro Met Glu Asn Val Lys Lys Met Gly Gln Tyr
        35                  40                  45

Gly Met Met Gly Ile Pro Phe Ser Lys Glu Tyr Gly Gly Ala Gly Gly
    50                  55                  60

Asp Val Leu Ser Tyr Ile Ile Ala Val Glu Glu Leu Ser Lys Val Cys

-continued

```
                65                  70                  75                  80
Gly Thr Thr Gly Val Ile Leu Ser Ala His Thr Ser Leu Cys Ala Ser
                    85                  90                  95
Leu Ile Asn Glu His Gly Thr Glu Glu Gln Lys Gln Lys Tyr Leu Val
                100                 105                 110
Pro Leu Ala Lys Gly Glu Lys Ile Gly Ala Tyr Gly Leu Thr Glu Pro
                115                 120                 125
Asn Ala Gly Thr Asp Ser Gly Ala Gln Gln Thr Val Ala Val Leu Glu
                130                 135                 140
Gly Asp His Tyr Val Ile Asn Gly Ser Lys Ile Phe Ile Thr Asn Gly
145                 150                 155                 160
Gly Val Ala Asp Thr Phe Val Ile Phe Ala Met Thr Asp Arg Thr Lys
                165                 170                 175
Gly Thr Lys Gly Ile Ser Ala Phe Ile Ile Glu Lys Gly Phe Lys Gly
                180                 185                 190
Phe Ser Ile Gly Lys Val Glu Gln Lys Leu Gly Ile Arg Ala Ser Ser
                195                 200                 205
Thr Thr Glu Leu Val Phe Glu Asp Met Ile Val Pro Val Glu Asn Met
210                 215                 220
Ile Gly Lys Glu Gly Lys Gly Phe Pro Ile Ala Met Lys Thr Leu Asp
225                 230                 235                 240
Gly Gly Arg Ile Gly Ile Ala Ala Gln Ala Leu Gly Ile Ala Glu Gly
                245                 250                 255
Ala Phe Asn Glu Ala Arg Ala Tyr Met Lys Glu Arg Lys Gln Phe Gly
                260                 265                 270
Arg Ser Leu Asp Lys Phe Gln Gly Leu Ala Trp Met Met Ala Asp Met
                275                 280                 285
Asp Val Ala Ile Glu Ser Ala Arg Tyr Leu Val Tyr Lys Ala Ala Tyr
                290                 295                 300
Leu Lys Gln Ala Gly Leu Pro Tyr Thr Val Asp Ala Ala Arg Ala Lys
305                 310                 315                 320
Leu His Ala Ala Asn Val Ala Met Asp Val Thr Thr Lys Ala Val Gln
                325                 330                 335
Leu Phe Gly Gly Tyr Gly Tyr Thr Lys Asp Tyr Pro Val Glu Arg Met
                340                 345                 350
Met Arg Asp Ala Lys Ile Thr Glu Ile Tyr Glu Gly Thr Ser Glu Val
                355                 360                 365
Gln Lys Leu Val Ile Ser Gly Lys Ile Phe Arg
                370                 375

<210> SEQ ID NO 18
<211> LENGTH: 1140
<212> TYPE: DNA
<213> ORGANISM: Clostridium acetobutylicum

<400> SEQUENCE: 18
ttatctaaaa attttttcctg aaataactaa tttctgaact tctgaagttc cttcatatat      60
ttcagttatc ttagcatctc tcatcattct tcaactgga  taatcttttg tatatccgta     120
tccaccaaat aattgtactg ccttagttgt tacatccatt gctacatttg cagcatgaag     180
cttagctctt gcagcatcaa ctgtgtatgg aagtcctgct tgtttaagat atgctgcttt     240
atatactaaa tatctagctg attctatagc tacatccata tctgccatca tccatgcaag     300
accttggaat ttgtcaaggc ttcttccaaa ttgtttttctc tccttcatgt aagctcttgc     360
```

```
ttcgttgaaa gcaccttcag ctataccctaa agcttgagct gctataccaa ttcttcctcc      420
atcaagagtt ttcattgcta tagggaagcc ttttccttct ttaccaatca tgttttctac      480
tggtactatc atatcttcaa atacaagttc agttgttgat gaagctctta ttccaagctt      540
ttgttcaact ttaccaatag agaaaccttt gaagcctttt tctattataa atgctgatat      600 acctttgtt cctttagttc tgtcagtcat tgcaaatata acaaagtat ctgcaactcc        660 tccattagtt atgaatattt ttgaaccatt aattacataa tgatctcctt caagtacagc      720
tactgtttgt tgtgctccag aatctgttcc tgcatttggc tcagtcaatc cataagcacc      780 tatttttca cctttagcta aaggtactaa atattttgt tttttgttctt ctgtaccatg       840 ttcatttatt aatgaagcac aaagtgatgt atgtgctgaa agaataactc ctgtagtacc      900
gcaaaccttt gataattcct caacggcgat tatataagat aatacatctc cacctgcgcc      960
accatactct tttgaaaatg gaattcccat cataccatac tgacccattt tctttacatt      1020
ttccattgga aatctttctg tttcatcaat ttctgctgct ataggtttaa cttcatttc      1080 agcaaattct ctaaccatct gtcttactaa ttcttgttct cttgttaaat taaaatccat     1140
```

<210> SEQ ID NO 19
<211> LENGTH: 389
<212> TYPE: PRT
<213> ORGANISM: Clostridium acetobutylicum

<400> SEQUENCE: 19

Met Leu Ser Phe Asp Tyr Ser Ile Pro Thr Lys Val Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160

Leu Gly Val Gly His Asp Asp Met Arg Pro Lys Phe Ser Val Leu Asp
                165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
        195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
            245                 250                 255

Ser Leu Gly Lys Asp Arg Lys Trp Ser Cys His Pro Met Glu His Glu
        260                 265                 270

Leu Ser Ala Tyr Tyr Asp Ile Thr His Gly Val Gly Leu Ala Ile Leu
    275                 280                 285

Thr Pro Asn Trp Met Glu Tyr Ile Leu Asn Asp Asp Thr Leu His Lys
290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
        355                 360                 365

Thr Ile Gly Ser Leu Arg Pro Ile Asn Ala Glu Asp Val Leu Glu Ile
    370                 375                 380

Phe Lys Lys Ser Tyr
385

<210> SEQ ID NO 20
<211> LENGTH: 1170
<212> TYPE: DNA
<213> ORGANISM: Clostridium acetobutylicum

<400> SEQUENCE: 20
ttaataagat tttttaaata tctcaagaac atcctctgca tttattggtc ttaaacttcc      60
tattgttcct ccagaatttc taacagcttg ctttgccatt agttctagtt tatctttcc     120 tattccaact tctctaagct tgaaggaat acccaatgaa ttaaagtatt ctctcgtatt     180
tttaatagcc tctcgtgcta tttcatagtt atctttgttc ttgtctattc cccaaacatt     240
tattccataa gaaacaaatt tatgaagtgt atcgtcattt agaatatatt ccatccaatt     300
aggtgttaaa attgcaagtc ctacaccatg tgttatatca atatgcac ttaactcgtg      360 ttccatagga tgacaactcc atttctatc cttaccaagt gataatagac catttatagc     420
taaacttgaa gcccacatca aattagctct agcctcgtaa tcatcagtct tctccattgc     480
tattttccca tactttatac atgttcttaa gattgcttct gctataccgt cctgcacata     540
agcaccttca acaccactaa agtaagattc aaaggtgtga ctcataatgt cagctgttcc     600
cgctgctgtt tgatttttag gtactgtaaa agtatatgta ggatctaaca ctgaaaattt     660
aggtctcata tcatcatgtc ctactccaag cttttcatta gtctccatat ttgaaattac     720
tgcaatttga tccatttcag accctgttgc tgaaagagta agtatacttg caattggaag     780
aactttagtt attttagatg gatctttaac catgtcccat gtatcgccat cataataaac     840
tccagctgca attaccttag aacagtctat tgcacttcct cccctattg ctaatactaa      900 atccacatta ttttctctac atatttctat gccttttttt actgttgtta tcctaggatt     960
tggctctact cctgaaagtt catagaaagc tatattgttt tcttttaata tagctgttgc    1020
tctatcatat ataccgttcc tttttatact tcctccgcca taaactataa gcactcttga    1080
gccatatttc ttaattctt ctccaattac gtctattttt cctttccaa aaaaactttt     1140 agttggtatt gaataatcaa aacttagcat                                    1170

```
<210> SEQ ID NO 21
<211> LENGTH: 390
<212> TYPE: PRT
<213> ORGANISM: Clostridium acetobutylicum

<400> SEQUENCE: 21

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Leu Ala Ile Gly
            85                  90                  95

Gly Gly Ser Ala Ile Asp Cys Ala Lys Val Ile Ala Ala Cys Glu
            100                 105                 110

Tyr Asp Gly Asn Pro Trp Asp Ile Val Leu Asp Gly Ser Lys Ile Lys
            115                 120                 125

Arg Val Leu Pro Ile Ala Ser Ile Leu Thr Ile Ala Ala Thr Gly Ser
    130                 135                 140

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
                165                 170                 175

Pro Thr Tyr Thr Tyr Thr Val Pro Thr Asn Gln Thr Ala Ala Gly Thr
            180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380
```

Ile Phe Lys Lys Ser Val
385                 390

<210> SEQ ID NO 22
<211> LENGTH: 1173
<212> TYPE: DNA
<213> ORGANISM: Clostridium acetobutylicum

<400> SEQUENCE: 22

```
ttacacagat tttttgaata tttgtaggac ttcggaggcg tttactggtc ttaggtttcc    60
tatggttcct cctgtaagct ttactgattc ctttgccatt atgtccaatt tttcttcttc   120
aattccaaca tctctcagtc tagatggtaa acctagtaca tttacaaagt aatctcttgt   180
tttttgtatt gcttgatgtg ctatgtcata gtgattttt tctttgtcta ttccccaaac    240
atttacacca tattcaacaa acttgtacac tgtatcatta tttaaaatat actccatcca   300
attaggtgtt aaaattgcaa gccctacgcc gtgtgttatg tcgtaataag cacttaattc   360
atgttccatt aagtgtacac tccaattagt gtctttacca tatgttaaaa gtccattat    420
cgcaagactt gaagcccaca ttagattggc tcttgcctca taatcatccg gcttctcaag   480
agctattcct ccatatttaa tacaagttct taataacgct tctgccattc tatcctgcaa   540
atatgctgtt tttgtattac taaaatacac ctcaaatata tgactcataa tatcagctgt   600
tcctgctgct gtttgattgg taggtacggt atacgtatac gttggatcta atatagaaaa   660
cttaggagcc atatctggat gtgccgcaat tagttttcg tttgtatcca tattatttat    720
tactgcccac gtatccattt ctgatcctgt tgcagcaatg gttaatatac tagctatagg   780
aagcacccett tttattttg agccatctaa cacaatatcc catggatttc catcatattc   840
acatgctgct gctataacct tgcgcaatc tattgcactt cctccaccta gctagtac     900
tacttcaact ccatttttctc tacatatttt aactcctttt tcaactgtag ttactcttgg   960
atttggctct actcctgcaa gttcataaaa tttaatactg ttttttttcaa gtatacttac  1020
agctttatca tatattccat ttctctttat acttcctcca ccataaacta taagcacttt  1080
agaaccatat tttttaagct ctcttccaag tacatttatc ttatctttac cgaaaaaaat  1140
tctagttggt attgaatatt cgaaatcaac cac                               1173
```

<210> SEQ ID NO 23
<211> LENGTH: 392
<212> TYPE: PRT
<213> ORGANISM: Clostridium acetobutylicum

<400> SEQUENCE: 23

Met Arg Asp Val Val Ile Val Ser Ala Val Arg Thr Ala Ile Gly Ala
1               5                   10                  15

Tyr Gly Lys Thr Leu Lys Asp Val Pro Ala Thr Glu Leu Gly Ala Ile
            20                  25                  30

Val Ile Lys Glu Ala Val Arg Arg Ala Asn Ile Asn Pro Asn Glu Ile
        35                  40                  45

Asn Glu Val Ile Phe Gly Asn Val Leu Gln Ala Gly Leu Gly Gln Asn
    50                  55                  60

Pro Ala Arg Gln Ala Ala Val Lys Ala Gly Leu Pro Leu Glu Thr Pro
65                  70                  75                  80

Ala Phe Thr Ile Asn Lys Val Cys Gly Ser Gly Leu Arg Ser Ile Ser
                85                  90                  95

Leu Ala Ala Gln Ile Ile Lys Ala Gly Asp Ala Asp Thr Ile Val Val
            100                 105                 110

Gly Gly Met Glu Asn Met Ser Arg Ser Pro Tyr Leu Ile Asn Asn Gln
            115                 120                 125

Arg Trp Gly Gln Arg Met Gly Asp Ser Glu Leu Val Asp Glu Met Ile
        130                 135                 140

Lys Asp Gly Leu Trp Asp Ala Phe Asn Gly Tyr His Met Gly Val Thr
145                 150                 155                 160

Ala Glu Asn Ile Ala Glu Gln Trp Asn Ile Thr Arg Glu Glu Gln Asp
                165                 170                 175

Glu Phe Ser Leu Met Ser Gln Gln Lys Ala Glu Lys Ala Ile Lys Asn
            180                 185                 190

Gly Glu Phe Lys Asp Glu Ile Val Pro Val Leu Ile Lys Thr Lys Lys
        195                 200                 205

Gly Glu Ile Val Phe Asp Gln Asp Glu Phe Pro Arg Phe Gly Asn Thr
    210                 215                 220

Ile Glu Ala Leu Arg Lys Leu Lys Pro Ile Phe Lys Glu Asn Gly Thr
225                 230                 235                 240

Val Thr Ala Gly Asn Ala Ser Gly Leu Asn Asp Gly Ala Ala Ala Leu
                245                 250                 255

Val Ile Met Ser Ala Asp Lys Ala Asn Ala Leu Gly Ile Lys Pro Leu
            260                 265                 270

Ala Lys Ile Thr Ser Tyr Gly Ser Tyr Gly Val Asp Pro Ser Ile Met
        275                 280                 285

Gly Tyr Gly Ala Phe Tyr Ala Thr Lys Ala Ala Leu Asp Lys Ile Asn
    290                 295                 300

Leu Lys Pro Glu Asp Leu Asp Leu Ile Glu Ala Asn Glu Ala Tyr Ala
305                 310                 315                 320

Ser Gln Ser Ile Ala Val Thr Arg Asp Leu Asn Leu Asp Met Ser Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Leu Tyr Ala Met Gln Lys Arg
        355                 360                 365

Asp Ser Lys Lys Gly Leu Ala Thr Leu Cys Ile Gly Gly Gly Gln Gly
    370                 375                 380

Thr Ala Leu Val Val Glu Arg Asp
385                 390

<210> SEQ ID NO 24
<211> LENGTH: 1179
<212> TYPE: DNA
<213> ORGANISM: Clostridium acetobutylicum

<400> SEQUENCE: 24
ttagtctctt tcaactacga gagctgttcc ctgacctcca ccaatacata gagtagcaag      60 acctttttt gaatctcttt tttgcatagc gtatagtaat gttactaaaa tacgtgcacc      120
agatgcacct attggatgtc caagtgctat agctccacca ttaacattaa ctttactcat     180
atctaaattt aaatctctag ttactgctat actttgagaa gcatatgcct cgttagcttc     240
aattaaatct aagtcttcag gttttaaatt aattttatct aaggcagctt tagttgcata     300
aaaagctcca tatcccatta tgatggatc taccccatat gatccgtaag aagtaatctt     360
agcaagtggt ttattccga gagcgttagc tttatcagcg ctcattatta ctagtgctgc     420
agctccatca tttaatccgg atgcattacc tgctgtaaca gtaccatttt ccttgaaaat    480

-continued

```
aggtttaagt tttcttaatg cttcaatagt gtttccgaat ctaggaaatt catcttgatc    540
aaagactatt tcacctttt tagtctttat taatacagga actatttcat ccttaaattc    600
tccattttta atggctttt cagcttttg ttgtgacata agtgaaaatt catcttgctc    660
ttctcttgtt atattccatt gttctgcaat attttctgca gttactccca tatgatatcc    720
attaaatgca tcccacaaac catcctttat catttcatca actaattcac tatctcccat    780
tctttgaccc catctctgat tgttaatcaa atatggtgat ctagacatat tttccatacc    840
acctactaca atggtatcag catctccagc ttttataatt tgagctgcta aacttataga    900
tcttaaacct gaaccacaaa ccttattgat tgtaaacgca ggtgtttcta aaggtaatcc    960
tgcttttact gctgcttgtc ttgctgggtt ttggcctaat ccagcttgaa gtacatttcc   1020
aaaaataact tcattaatct catttggatt tatattagct cttcttacag cttccttat   1080
tactatagct cctaactctg ttgcaggtac atcctttaat gttttccat atgctcctat   1140
tgcagttctt acagcactta ctattactac atctctcat                          1179
```

<210> SEQ ID NO 25
<211> LENGTH: 244
<212> TYPE: PRT
<213> ORGANISM: Clostridium acetobutylicum

<400> SEQUENCE: 25

```
Met Leu Lys Asp Glu Val Ile Lys Gln Ile Ser Thr Pro Leu Thr Ser
1               5                   10                  15

Pro Ala Phe Pro Arg Gly Pro Tyr Lys Phe His Asn Arg Glu Tyr Phe
                20                  25                  30

Asn Ile Val Tyr Arg Thr Asp Met Asp Ala Leu Arg Lys Val Val Pro
            35                  40                  45

Glu Pro Leu Glu Ile Asp Glu Pro Leu Val Arg Phe Glu Ile Met Ala
        50                  55                  60

Met His Asp Thr Ser Gly Leu Gly Cys Tyr Thr Glu Ser Gly Gln Ala
65                  70                  75                  80

Ile Pro Val Ser Phe Asn Gly Val Lys Gly Asp Tyr Leu His Met Met
                85                  90                  95

Tyr Leu Asp Asn Glu Pro Ala Ile Ala Val Gly Arg Glu Leu Ser Ala
            100                 105                 110

Tyr Pro Lys Lys Leu Gly Tyr Pro Lys Leu Phe Val Asp Ser Asp Thr
        115                 120                 125

Leu Val Gly Thr Leu Asp Tyr Gly Lys Leu Arg Val Ala Thr Ala Thr
    130                 135                 140

Met Gly Tyr Lys His Lys Ala Leu Asp Ala Asn Glu Ala Lys Asp Gln
145                 150                 155                 160

Ile Cys Arg Pro Asn Tyr Met Leu Lys Ile Pro Asn Tyr Asp Gly
                165                 170                 175

Ser Pro Arg Ile Cys Glu Leu Ile Asn Ala Lys Ile Thr Asp Val Thr
            180                 185                 190

Val His Glu Ala Trp Thr Gly Pro Thr Arg Leu Gln Leu Phe Asp His
        195                 200                 205

Ala Met Ala Pro Leu Asn Asp Leu Pro Val Lys Glu Ile Val Ser Ser
    210                 215                 220

Ser His Ile Leu Ala Asp Ile Ile Leu Pro Arg Ala Glu Val Ile Tyr
225                 230                 235                 240

Asp Tyr Leu Lys
```

<210> SEQ ID NO 26
<211> LENGTH: 735
<212> TYPE: DNA
<213> ORGANISM: Clostridium acetobutylicum

<400> SEQUENCE: 26

```
ttacttaaga taatcatata aacttcagc tctaggcaat attatatctg caagaatgtg      60
agagctagaa acaatctctt ttactggcaa atcattaagt ggcgccatag cgtgatcaaa    120
taactgcagt cgagttggtc ctgtccaagc ttcatgtacg gtaacatctg tgattttcgc    180
atttataagc tcacatattc tagggcttcc atcataattg ggtattattt tcaacatata    240
attagggcga caatttgat cctttgcttc attagcatct aaggctttat gtttgtaccc     300
cattgtagct gtcgcaactc taagttttcc atagtctaaa gttcctacta aagtatctga    360
atccacaaaa agctttggat acccgagctt tttaggatat gcacttaatt cccttcctac    420
tgcaattgca ggctcattat ctaaatacat catatgaaga taatctccct taactccatt    480
aaagcttacg ggaatagcct gtccgctttc tgtataacaa ccaagtccac tcgtatcatg    540
cattgccata atttcaaacc tgactaaggg ctcatcaatt tctaaaggct ctggcacaac    600
tttacgaagt gcatccatat ctgtacgata tacaatgtta aaatactcac gattatgaaa    660
tttatagggt cctctaggaa atgcaggcga agttaatggc gtgctaattt gtttaattac    720
ttcatccttt aacat                                                     735
```

<210> SEQ ID NO 27
<211> LENGTH: 553
<212> TYPE: PRT
<213> ORGANISM: Synechocystis species

<400> SEQUENCE: 27

Met Arg Asn Phe Pro Glu Ile Gln Asn Thr Ala Tyr Asp Leu Ile Val
1               5                   10                  15

Ile Gly Gly Gly Ile Asn Gly Val Gly Thr Ala Arg Asp Gly Ala Leu
            20                  25                  30

Arg Gly Leu Lys Thr Leu Leu Ile Glu Lys Asp Asp Phe Ala Ser Gly
        35                  40                  45

Thr Ser Ser Trp Ser Thr Arg Leu Ile His Gly Gly Leu Arg Tyr Leu
    50                  55                  60

Glu Tyr Phe Glu Phe Asn Leu Val Arg Glu Ser Leu Arg Glu Arg Glu
65                  70                  75                  80

Val Leu Leu His Thr Ala Pro His Leu Val Gln Pro Leu Gln Leu Thr
                85                  90                  95

Ile Pro Val Tyr Asp Trp Ser Ser Arg Ala Tyr Trp Glu Ile Gln Ala
            100                 105                 110

Gly Met Ile Leu Tyr Asp Ile Leu Ser Phe Asp Lys Thr Leu Pro Ser
        115                 120                 125

His Arg Met Leu Ser Pro Gln Gln Phe Gln Leu Phe Arg Ala Ala
    130                 135                 140

Glu Lys Lys Gly Leu Lys Gly Ala Gln Tyr Phe Asp Gly Gln Val
145                 150                 155                 160

Glu Tyr Ala Glu Arg Leu Asp Leu Glu Val Thr Leu Ser Ala Gln Lys
                165                 170                 175

Ala Gly Ala Ala Met Leu Asn Tyr Val Ala Val Lys Gly Leu Glu Lys
            180                 185                 190

Gly Glu Asn Asn Leu Ile Thr Ala Ile His Cys Gln Asp Gln Leu Ser

```
                  195                 200                 205
Gly Glu Lys Phe Thr Val Asn Ser Ala Gln Ala Ile Val Ile Asn Thr
    210                 215                 220

Thr Gly Pro Trp Val Asp Glu Val Cys Gly Leu Ala His Arg Gly Gly
225                 230                 235                 240

Glu Pro Val Ala Ile Val Gln Glu Arg Lys Ile Gly Thr Lys Gly
                245                 250                 255

Ser His Ile Val Val Asp Pro Phe Pro Gly Ala Pro Ala Ser Ala Leu
            260                 265                 270

Tyr Val Glu Ala Phe Val Asp Lys Arg Pro Tyr Phe Ile Ile Pro Trp
        275                 280                 285

Leu Gly Lys Tyr Leu Ile Gly Thr Thr Asp His Arg Tyr Asp Gly Ser
    290                 295                 300

Leu Asp Arg Val Lys Ala Ser Asp Asp Glu Ile Asp Tyr Leu Ile Ala
305                 310                 315                 320

Glu Thr Asn Arg Val Met Pro Ala Ala Gln Leu Thr Arg Gln Asp Val
                325                 330                 335

Arg Phe Thr Tyr Ser Gly Val Arg Pro Leu Pro Tyr Thr Asp Gly Lys
            340                 345                 350

Lys Ala Gly Ser Ile Thr Arg Asn His Ile Leu Tyr Asp His Ser Gln
        355                 360                 365

Asp Gly Val Asn Asn Leu Ile Ser Leu Ile Gly Gly Lys Leu Thr Thr
    370                 375                 380

Tyr Arg Gln Val Gly Glu Glu Met Val Asp Lys Val Tyr Gly Lys Leu
385                 390                 395                 400

Arg Arg Ser Ala Pro Pro Cys Pro Thr Leu Thr Gln Pro Leu Pro Gly
                405                 410                 415

Ala Glu Ala Tyr Pro Leu Ser Leu Glu Thr Ala Met Asp Lys Tyr Gly
            420                 425                 430

Asn His Leu Glu Arg His Ser Ile Gln His Leu Phe Cys Leu Tyr Gly
        435                 440                 445

Ala Arg Ala Gly Asp Ile Leu Ala Leu Val His Gly Ala Pro Glu Leu
    450                 455                 460

Gly Glu Arg Ile Ile Pro Ser Leu Pro Asp Ile Lys Ala Gln Val Val
465                 470                 475                 480

Phe Ala Val Gln Ala Glu Met Ala His Thr Leu Val Asp Ile Cys Arg
                485                 490                 495

Arg Arg Thr Ala Ile Ala Met Val Thr Asn Asp Tyr Gly Phe Ser Ala
            500                 505                 510

Leu Ala Gly Ile Cys Gln Thr Leu Thr Asp His Cys Gly Trp Thr Gln
        515                 520                 525

Glu Gln Cys Asp Lys Gln Ile Gln Lys Tyr His Glu Tyr Met Glu Gln
    530                 535                 540

Asn Cys Ile Pro Asp Tyr Cys Leu His
545                 550
```

<210> SEQ ID NO 28
<211> LENGTH: 1682
<212> TYPE: DNA
<213> ORGANISM: Synechocystis species

<400> SEQUENCE: 28
caatctcgag tcagtggaga caatagtcgg gaatgcagtt ttgctccata tattcatggt    60
acttttgaat tgcttgtca cattgctcct gggtccagcc acaatggtct gttaacgttt    120

```
ggcaaatgcc ggccagggcg ctaaagccat aatcgttagt caccatggcg atcgccgtac    180
gtcgtcgaca aatatccacc aaggtgtggg ccatttctgc ttgtactgca aaacaacttt    240
gggctttgat atccggcaag gaaggaataa tcctttcccc caactccggc gctccgtgga    300
ctaaggctaa aatgtctcca gccctggctc cgtaaaggca aaataaatgt tgaatagaat    360
gacgctccaa atgattgcca tatttatcca tggcagtttc caaggacagg ggataggctt    420
ctgcccccgg taaaggttgg gtcagggttg acaggagg agcagagcgt ctcagcttgc    480
cataaacctt atccaccatt tcttctccca cctggcgata ggtggtcaac ttaccgccaa    540
ttagggaaat caaattatta actccgtctt gactatggtc ataaagaata tggttgcggg    600
taatactgcc ggcctttttg ccatcggtgt agggcagagg gcgcaccccg aataggtga    660
aacgcacatc ctgcctggtt aactgagctg ctggcatcac ccggttagtt tccgcaatca    720
ggtaatcaat ctcgtcatca ctggctttaa ccctgtcgag ggaaccatca tagcggtggt    780
ccgtggtgcc aatcagatat ttacccaacc agggaatgat gaaataggc cgtttatcca    840
caaacgcttc cacatataag gctgaagcgg gggctccagg aagggatcc accacaatat    900
gactgcccct ggtgccacca attttctctt cttggacaat ggcaacgggt tctcccctc    960
gatgggctaa ccacaaact tcatctaccc aggggccagt ggtattaatg acgatcgcct   1020
gggcgctatt aacagtaaat ttttctccgc tcagttgatc ctggcaatgg atggcggtaa   1080
tcaggttatt ttcccctttc tccaacccct tcacagccac ataattgagc atggccgccc   1140
cggcctttg ggccgatagg gtcacttcta aatctaaccg ttccgcatat tccacctggc   1200
cgtcaaaata ttgggctcct ccttttaagc cttttttctc cgccgctcgg aacagttgct   1260
ggaactgttg ggggcttaac atcctatggg aagggagggt tttatcaaaa ctgaggatgt   1320
cgtaaagaat catgcccgcc tgaatttccc aataggcccg gctcgaccag tcgtacaccg   1380
gaatggtcaa ctggaggggc tggaccaaat ggggggcggt gtggagcaga acttcccgct   1440
cccgcaggga ttcccgcacc agattaaatt caaaatattc cagatagcgc aggccgccat   1500
ggattaagcg ggtggaccaa ctactcgtac cactggcgaa atcatccttt tcgatcagga   1560
gggttttag gccccgtagg gctccgtccc gggccgtgcc aaccccgtta atgcctcccc   1620
caatcacaat taggtcatag gccgtatttt ggatttctgg gaaattacgc atatcgatat   1680
tt                                                                  1682
```

<210> SEQ ID NO 29
<211> LENGTH: 250
<212> TYPE: PRT
<213> ORGANISM: Saccharomyces cerevisiae

<400> SEQUENCE: 29

```
Met Pro Leu Thr Thr Lys Pro Leu Ser Leu Lys Ile Asn Ala Ala Leu
1               5                   10                  15

Phe Asp Val Asp Gly Thr Ile Ile Ser Gln Pro Ala Ile Ala Ala
            20                  25                  30

Phe Trp Arg Asp Phe Gly Lys Asp Lys Pro Tyr Phe Asp Ala Glu His
        35                  40                  45

Val Ile His Ile Ser His Gly Trp Arg Thr Tyr Asp Ala Ile Ala Lys
    50                  55                  60

Phe Ala Pro Asp Phe Ala Asp Glu Glu Tyr Val Asn Lys Leu Glu Gly
65                  70                  75                  80

Glu Ile Pro Glu Lys Tyr Gly Glu His Ser Ile Glu Val Pro Gly Ala
```

85                  90                  95
Val Lys Leu Cys Asn Ala Leu Asn Ala Leu Pro Lys Glu Lys Trp Ala
                100                 105                 110

Val Ala Thr Ser Gly Thr Arg Asp Met Ala Lys Lys Trp Phe Asp Ile
            115                 120                 125

Leu Lys Ile Lys Arg Pro Glu Tyr Phe Ile Thr Ala Asn Asp Val Lys
        130                 135                 140

Gln Gly Lys Pro His Pro Glu Pro Tyr Leu Lys Gly Arg Asn Gly Leu
145                 150                 155                 160

Gly Phe Pro Ile Asn Glu Gln Asp Pro Ser Lys Ser Lys Val Val Val
                165                 170                 175

Phe Glu Asp Ala Pro Ala Gly Ile Ala Ala Gly Lys Ala Ala Gly Cys
            180                 185                 190

Lys Ile Val Gly Ile Ala Thr Thr Phe Asp Leu Asp Phe Leu Lys Glu
        195                 200                 205

Lys Gly Cys Asp Ile Ile Val Lys Asn His Glu Ser Ile Arg Val Gly
    210                 215                 220

Glu Tyr Asn Ala Glu Thr Asp Glu Val Glu Leu Ile Phe Asp Asp Tyr
225                 230                 235                 240

Leu Tyr Ala Lys Asp Asp Leu Leu Lys Trp
                245                 250

<210> SEQ ID NO 30
<211> LENGTH: 753
<212> TYPE: DNA
<213> ORGANISM: Saccharomyces cerevisiae

<400> SEQUENCE: 30
atgcctttga ccacaaaacc tttatctttg aaaatcaacg ccgctctatt cgatgttgac     60
ggtaccatca tcatctctca accagccatt gctgctttct ggagagattt cggtaaagac    120
aagccttact tcgatgccga acacgttatt cacatctctc acggttggag aacttacgat    180
gccattgcca agttcgctcc agactttgct gatgaagaat acgttaacaa gctagaaggt    240
gaaatcccag aaaagtacgg tgaacactcc atcgaagttc aggtgctgtc aagttgtgt    300 aatgctttga cgccttgcc aaaggaaaaa tgggctgtcg ccacctctgg tacccgtgac    360
atggccaaga atggttcga cattttgaag atcaagagac cagaatactt catcaccgcc    420
aatgatgtca agcaaggtaa gcctcaccca gaaccatact aaagggtag aaacggtttg    480 ggtttcccaa ttaatgaaca agacccatcc aaatctaagg ttgttgtctt tgaagacgca    540
ccagctggta ttgctgctgg taaggctgct ggctgtaaaa tcgttggtat tgctaccact    600
ttcgatttgg acttcttgaa ggaaaagggt tgtgacatca ttgtcaagaa ccacgaatct    660
atcagagtcg gtgaatacaa cgctgaaacc gatgaagtcg aattgatctt tgatgactac    720
ttatacgcta aggatgactt gttgaaatgg taa                                  753

<210> SEQ ID NO 31
<211> LENGTH: 555
<212> TYPE: PRT
<213> ORGANISM: Klebsiella pneumoniae

<400> SEQUENCE: 31

Met Lys Arg Ser Lys Arg Phe Ala Val Leu Ala Gln Arg Pro Val Asn
1               5                   10                  15

Gln Asp Gly Leu Ile Gly Glu Trp Pro Glu Glu Gly Leu Ile Ala Met
            20                  25                  30

```
Asp Ser Pro Phe Asp Pro Val Ser Val Lys Val Asp Asn Gly Leu
        35                  40                  45
Ile Val Glu Leu Asp Gly Lys Arg Arg Asp Gln Phe Asp Met Ile Asp
 50                  55                  60
Arg Phe Ile Ala Asp Tyr Ala Ile Asn Val Glu Arg Thr Glu Gln Ala
 65                  70                  75                  80
Met Arg Leu Glu Ala Val Glu Ile Ala Arg Met Leu Val Asp Ile His
                 85                  90                  95
Val Ser Arg Glu Glu Ile Ile Ala Ile Thr Thr Ala Ile Thr Pro Ala
                100                 105                 110
Lys Ala Val Glu Val Met Ala Gln Met Asn Val Val Glu Met Met Met
                115                 120                 125
Ala Leu Gln Lys Met Arg Ala Arg Arg Thr Pro Ser Asn Gln Cys His
         130                 135                 140
Val Thr Asn Leu Lys Asp Asn Pro Val Gln Ile Ala Ala Asp Ala Ala
145                 150                 155                 160
Glu Ala Gly Ile Arg Gly Phe Ser Glu Gln Glu Thr Thr Val Gly Ile
                165                 170                 175
Ala Arg Tyr Ala Pro Phe Asn Ala Leu Ala Leu Leu Val Gly Ser Gln
         180                 185                 190
Cys Gly Arg Pro Gly Val Leu Thr Gln Cys Ser Val Glu Glu Ala Thr
         195                 200                 205
Glu Leu Glu Leu Gly Met Arg Gly Leu Thr Ser Tyr Ala Glu Thr Val
 210                 215                 220
Ser Val Tyr Gly Thr Glu Ala Val Phe Thr Asp Gly Asp Asp Thr Pro
225                 230                 235                 240
Trp Ser Lys Ala Phe Leu Ala Ser Ala Tyr Ala Ser Arg Gly Leu Lys
                245                 250                 255
Met Arg Tyr Thr Ser Gly Thr Gly Ser Glu Ala Leu Met Gly Tyr Ser
                260                 265                 270
Glu Ser Lys Ser Met Leu Tyr Leu Glu Ser Arg Cys Ile Phe Ile Thr
         275                 280                 285
Lys Gly Ala Gly Val Gln Gly Leu Gln Asn Gly Ala Val Ser Cys Ile
290                 295                 300
Gly Met Thr Gly Ala Val Pro Ser Gly Ile Arg Ala Val Leu Ala Glu
305                 310                 315                 320
Asn Leu Ile Ala Ser Met Leu Asp Leu Glu Val Ala Ser Ala Asn Asp
                325                 330                 335
Gln Thr Phe Ser His Ser Asp Ile Arg Arg Thr Ala Arg Thr Leu Met
             340                 345                 350
Gln Met Leu Pro Gly Thr Asp Phe Ile Phe Ser Gly Tyr Ser Ala Val
         355                 360                 365
Pro Asn Tyr Asp Asn Met Phe Ala Gly Ser Asn Phe Asp Ala Glu Asp
 370                 375                 380
Phe Asp Asp Tyr Asn Ile Leu Gln Arg Asp Leu Met Val Asp Gly Gly
385                 390                 395                 400
Leu Arg Pro Val Thr Glu Ala Glu Thr Ile Ala Ile Arg Gln Lys Ala
                405                 410                 415
Ala Arg Ala Ile Gln Ala Val Phe Arg Glu Leu Gly Leu Pro Pro Ile
             420                 425                 430
Ala Asp Glu Glu Val Glu Ala Ala Thr Tyr Ala His Gly Ser Asn Glu
         435                 440                 445
```

```
Met Pro Pro Arg Asn Val Val Glu Asp Leu Ser Ala Val Glu Glu Met
    450                 455                 460

Met Lys Arg Asn Ile Thr Gly Leu Asp Ile Val Gly Ala Leu Ser Arg
465                 470                 475                 480

Ser Gly Phe Glu Asp Ile Ala Ser Asn Ile Leu Asn Met Leu Arg Gln
                485                 490                 495

Arg Val Thr Gly Asp Tyr Leu Gln Thr Ser Ala Ile Leu Asp Arg Gln
                500                 505                 510

Phe Glu Val Ser Ala Val Asn Asp Ile Asn Asp Tyr Gln Gly Pro
                515                 520                 525

Gly Thr Gly Tyr Arg Ile Ser Ala Glu Arg Trp Ala Glu Ile Lys Asn
    530                 535                 540

Ile Pro Gly Val Val Gln Pro Asp Thr Ile Glu
545                 550                 555

<210> SEQ ID NO 32
<211> LENGTH: 1688
<212> TYPE: DNA
<213> ORGANISM: Klebsiella pneumoniae

<400> SEQUENCE: 32
aaatatcgat ttattcaatg gtgtcaggct gaaccacgcc cggaatattt ttgatctccg      60
cccagcgttc ggcagagatg cgatagccgg tgcccggccc ctgatagtca ttgatgtcgt     120
tgaccgcgct caccacctcg aactgtcgat cgagaatggc cgaggtctgc aggtaatcgc     180
cggtgacccg ctggcgcagc atattgagaa tattgctggc gatatcctca agccgctgc     240 ggctcagcgc gccgacaata tcgaggccgg tgatgttgcg cttcatcatc tcttccaccg     300
cactcagatc ctccaccacg ttacgcggcg catctcgtt gctgccgtgc gcgtaggtgg      360
cggcctccac ctcctcgtcg gcgattggcg gcagccccag ctcgcggaaa accgcctgga     420
tcgcccgcgc cgctttctgg cgaatggcaa tggtttccgc ctcggtcacc ggacgcaggc     480
cgccgtcaac catcaggtca cgctgcagaa tgttgtaatc atcaaaatct ccgcatcga     540 agttcgagcc ggcgaacatg ttgtcgtagt tcggcaccgc gctgtagccg agaaaaataa     600
agtcggtgcc cggcagcatc tgcatcaggg tgcgcgcggt gcggcgaata tccgagtggg     660
agaaagtctg gtcgttggcg gacgccactt cgaggtcgag catagaggcg atcaggtttt     720
ccgccagcac cgcccgaatg cccgacggca cagcgccggt catgccgata cagctcactg     780
cgccgttttg cagcccctga accccggcgc ctttggtaat gaagatgcag cgcgattcga     840
ggtagagcat cgacttgctc tccgaatagc ccatcagcgc ttcggatccg gtgccggagg     900
tgtagcgcat tttcaacccg cgggaggcgt aggccgaggc gaggaacgcc tttgaccacg     960
gagtatcatc gccgtcggta ataccgcctt cagtgccgta gaccgacacc gtctcggcgt    1020
agctggttaa gccacgcatg cccagctcca gctcggtggc ctcttccacc gagcactgcg    1080
tcaacacgcc gggacggccg cactgcgagc cgaccaacag cgccagggcg ttaaacggcg    1140
catagcgcgc gataccgacc gtggtctcct gttctgagaa gccgcggatc ccggcctcgg    1200
cggcgtcagc ggcaatctgc accggattat ctttgagatt ggtgacgtgg cactggttgg    1260 aggggggtccg gcgggcacgc atcttctgca gcgccatcat catctccacc acgttcatct    1320
gcgccatcac ctcgaccgct ttggccggcg tgatggcggt agtgatggca atgatctcct    1380
cccggctgac gtgaatatcc accagcatgc gggctatttc caccgcctcc aggcgcattg    1440
cctgctctgt gcgctcaacg ttgatcgcgt aatcggcgat aaaccggtcg atcatgtcaa    1500
```

```
actggtcccg gcgtttgccg tccagctcga cgatcagacc gttgtccact tttactgaag    1560
agaccgggtc aaaggggctg tccatggcga tcagcccctc ttcaggccac tcgccaatca    1620
gcccgtcctg attgacgggg cgctgggcca gtactgcaaa tcgttttgat cttttcataa    1680
gcttttgg                                                              1688
```

<210> SEQ ID NO 33
<211> LENGTH: 392
<212> TYPE: PRT
<213> ORGANISM: Klebsiella pneumoniae

<400> SEQUENCE: 33

```
Met Leu Asn Gly Leu Lys Pro Leu Ser Arg Ser Leu Arg Trp Gly Met
1               5                   10                  15

Val Gly Gly Gly Thr Ser Gln Ile Gly Tyr Ser His Arg Cys Ala
            20                  25                  30

Ala Leu Arg Asp Asn Val Tyr Thr Leu Leu Ala Gly Ala Leu Asp Val
        35                  40                  45

Asp Ala Glu Arg Gly Arg Ala Phe Gly Glu Gln Leu Gly Ile Ala Pro
    50                  55                  60

Glu Arg Cys Tyr Ala Asp Tyr Gln Thr Leu Phe Arg Glu Glu Ala Gln
65                  70                  75                  80

Arg Pro Asp Gly Ile Glu Val Val Ser Val Thr Thr Pro Asn Asn Thr
                85                  90                  95

His Phe Ala Ile Thr Lys Ala Ala Leu Glu Ala Gly Leu His Val Ile
            100                 105                 110

Cys Glu Lys Pro Leu Cys Phe Thr Ala Glu Glu Ala Arg Glu Leu Val
        115                 120                 125

Asp Leu Ser Lys Lys Gln Asn Lys Ile Val Gly Val Thr Tyr Gly Tyr
    130                 135                 140

Ala Gly Tyr Gln Met Ile Gln Gln Ala Arg Gln Met Ile Ala Asp Gly
145                 150                 155                 160

Leu Leu Gly Glu Ile Arg Ile Val Asn Met Gln Phe Ala His Gly Phe
                165                 170                 175

His Asn Gln Ala Val Glu Leu Gln Ala Glu Ser Thr Arg Trp Arg Val
            180                 185                 190

Thr Pro Lys Phe Ala Gly Pro Ser Tyr Val Leu Gly Asp Leu Ala Thr
        195                 200                 205

His Pro Leu Phe Val Ala Glu Thr Met Ala Pro Gln Leu Asn Ile Lys
    210                 215                 220

Arg Leu Met Cys Ser Arg Gln Ser Phe Val Pro Ser Arg Ala Pro Leu
225                 230                 235                 240

Glu Asp Asn Ala Phe Val Leu Met Glu Tyr Asp Asn Gly Ala Val Gly
                245                 250                 255

Ser Met Trp Thr Ser Ala Val Asn Ser Gly Ala Met His Ser Gln Lys
            260                 265                 270

Val Arg Ile Val Gly Glu Lys Ala Ser Ile Glu Trp Trp Asp Glu His
        275                 280                 285

Pro Asn Gln Leu Ser Tyr Glu Val Gln Gly Glu Pro Ala Arg Ile Leu
    290                 295                 300

Glu Arg Gly Met Pro Tyr Leu Ser Pro Asn Ala Leu Ala Asp Asp Arg
305                 310                 315                 320

Ile Gly Gly Gly His Pro Glu Gly Leu Phe Glu Ala Trp Ala Asn Leu
                325                 330                 335
```

Tyr Arg Arg Tyr Ala Gln Ala Ile Asp Ala Thr Asp Arg Asp Arg
                340                 345                 350

Ala Phe Leu Gln Asp Phe Trp Tyr Pro Asp Val Glu Ala Gly Leu His
            355                 360                 365

Gly Val Tyr Trp Val Glu Gln Cys Val Lys Ser Ala Asp Ala Gly Ser
        370                 375                 380

Gln Trp Val Asp Phe Thr Leu Pro
385                 390

<210> SEQ ID NO 34
<211> LENGTH: 1199
<212> TYPE: DNA
<213> ORGANISM: Klebsiella pneumoniae

<400> SEQUENCE: 34
gggtgatatc ttaaggtaaa gtaaagtcaa cccactggct gccagcgtca gccgatttga      60
cgcactgctc tacccaatag acgccgtgca gcccggcttc gacgtccgga taccagaagt     120
cttgcaggaa ggcgcgatcg tcgcggtccg tggcgtcaat cgcctgcgca tagcggcgat     180
agaggttggc ccaggcttcg aacagcccct tccggatggc gccgccaatg cggtcatccg     240
ccagcgcgtt cggcgacagg tagggcattc cacgttccag aatgcgcgcc ggctcaccct     300
gcacctcata gctgagctgg ttaggatgct catcccacca ttcgatgctt gcttttcgc     360 cgacgatgcg cacttttgc gagtgcatgg cgccgctgtt gaccgcgctg gtccacatgg     420
atccaaccgc gccgttgtca tattccatca ggacaaaggc gttatcttcc agcggcgcgc     480
gggagggaac aaagctctga cgggagcaca tcagccgttt gatattgagc tgcggcgcca     540
tggtttcggc gacaaacagc ggatgggtgg ccagatcccc aagcacatag ctgggcccgg     600
caaacttcgg cgttactcgc cagcgggtgg attctgcctg cagctcgacg gcctggttat     660
ggaagccgtg ggcgaattgc atgttaacga tgcggatctc gccgagcagt ccatcggcaa     720
tcatctgccg cgcctgctgg atcatctgat agccggcata gccgtaggtg acgccgacga     780
ttttgttctg tttttgctc agatccacca gctcgcgcgc ctcttcggcg taaagcaga     840 ggggcttttc gcagataacg tggagtcccg cctccagcgc cgctttggtg atggcgaaat     900
gggtattgtt cggggtggtg accgagacga cctcgatccc gtcagggcgc tgcgcctctt     960
cgcgaaacag ggtctggtag tcggcgtagc agcgctccgg cgcgatgccc agttgctcac    1020
cgaacgcgcg cccgcgctcg gcatcgacgt caagcgcgcc ggccagcagg gtataaacat    1080
tgtcacgcag cgccgcacag cggtggctgt agccgatctg actggttccc cgccgccga    1140 ccatgcccca gcgcagggaa cgggataagg gtttcaggcc gtttaacatg aattcattt    1199

<210> SEQ ID NO 35
<211> LENGTH: 325
<212> TYPE: PRT
<213> ORGANISM: Lactococcus lactis

<400> SEQUENCE: 35

Met Ala Asp Lys Gln Arg Lys Lys Val Ile Leu Val Gly Asp Gly Ala
1               5                   10                  15

Val Gly Ser Ser Tyr Ala Phe Ala Leu Val Asn Gln Gly Ile Ala Gln
            20                  25                  30

Glu Leu Gly Ile Val Asp Leu Phe Lys Glu Lys Thr Gln Gly Asp Ala
        35                  40                  45

Glu Asp Leu Ser His Ala Leu Ala Phe Thr Ser Pro Lys Lys Ile Tyr
    50                  55                  60

Ser Ala Asp Tyr Ser Asp Ala Ser Asp Ala Asp Leu Val Val Leu Thr
65                  70                  75                  80

Ser Gly Ala Pro Gln Lys Pro Gly Glu Thr Arg Leu Asp Leu Val Glu
                85                  90                  95

Lys Asn Leu Arg Ile Thr Lys Asp Val Val Thr Lys Ile Val Ala Ser
            100                 105                 110

Gly Phe Lys Gly Ile Phe Leu Val Ala Ala Asn Pro Val Asp Ile Leu
        115                 120                 125

Thr Tyr Ala Thr Trp Lys Phe Ser Gly Phe Pro Lys Asn Arg Val Val
130                 135                 140

Gly Ser Gly Thr Ser Leu Asp Thr Ala Arg Phe Arg Gln Ala Leu Ala
145                 150                 155                 160

Glu Lys Val Asp Val Asp Ala Arg Ser Ile His Ala Tyr Ile Met Gly
                165                 170                 175

Glu His Gly Asp Ser Glu Phe Ala Val Trp Ser His Ala Asn Val Ala
            180                 185                 190

Gly Val Lys Leu Glu Gln Trp Phe Gln Glu Asn Asp Tyr Leu Asn Glu
        195                 200                 205

Ala Glu Ile Val Glu Leu Phe Glu Ser Val Arg Asp Ala Ala Tyr Ser
210                 215                 220

Ile Ile Ala Lys Lys Gly Ala Thr Phe Tyr Gly Val Ala Val Ala Leu
225                 230                 235                 240

Ala Arg Ile Thr Lys Ala Ile Leu Asp Asp Glu His Ala Val Leu Pro
                245                 250                 255

Val Ser Val Phe Gln Asp Gly Gln Tyr Gly Val Ser Asp Cys Tyr Leu
            260                 265                 270

Gly Gln Pro Ala Val Val Gly Ala Glu Gly Val Val Asn Pro Ile His
        275                 280                 285

Ile Pro Leu Asn Asp Ala Glu Met Gln Lys Met Glu Ala Ser Gly Ala
290                 295                 300

Gln Leu Lys Ala Ile Ile Asp Glu Ala Phe Ala Lys Glu Glu Phe Ala
305                 310                 315                 320

Ser Ala Val Lys Asn
                325

<210> SEQ ID NO 36
<211> LENGTH: 998
<212> TYPE: DNA
<213> ORGANISM: Lactococcus lactis

<400> SEQUENCE: 36
caatctcgag atggctgata acaacgtaa gaaagttatc cttgttggtg acggtgctgt      60
aggttcatca tacgcttttg cccttgttaa ccaaggaatt gcacaagaat taggtattgt     120 tgacctttt aaagaaaaaa ctcaggggga tgcagaagac cttctctcatg ccttggcatt    180 tacatcacct aaaaagattt actctgcaga ctactctgat gcaagcgacg ctgacctcgt    240
tgtcttgact tctggtgctc cacaaaaacc aggtgaaact cgtcttgacc ttgttgaaaa    300
aaatcttcgt attactaaag atgttgtaac taaaattgtt gcttcaggat caaaggaat     360 cttcctcgtt gctgctaacc cagttgacat cttgacatac gcaacttgga aattctctgg    420
tttccctaaa aaccgtgttg taggttcagg tacttcactt gatactgcac gtttccgtca    480
agcattggct gaaaaagttg acgttgatgc tcgttcaatc cacgcataca tcatgggtga    540
acacggtgac tcagaatttg ctgtttggtc acacgctaac gttgctggtg ttaaattgga    600

```
acaatggttc caagaaaatg actaccttaa cgaagcagaa atcgttgaat tgtttgagtc    660
tgtacgtgat gcagcttact caatcatcgc taaaaaaggt gcaacattct acggtgtggc    720 tgtagcccctt gctcgtatta ctaaagcaat tcttgatgat gaacatgcag tacttcctgt    780
atcagtattc caagatggac aatatggggt aagcgactgc taccttggtc aaccagctgt    840
agttggtgct gaaggtgttg ttaacccaat tcacattcca ttgaacgatg ctgaaatgca    900
aaaaatggaa gcttctggag ctcaattgaa agctatcatc gatgaagctt ttgctaaaga    960
agaatttgct tctgcagtta aaaactaaga attcattg                            998
```

<210> SEQ ID NO 37
<211> LENGTH: 31
<212> TYPE: DNA
<213> ORGANISM: artificial
<220> FEATURE:
<223> OTHER INFORMATION: primer

<400> SEQUENCE: 37

```
aaatggtacc gaactgagat tagccccgga c                                   31
```

<210> SEQ ID NO 38
<211> LENGTH: 29
<212> TYPE: DNA
<213> ORGANISM: artificial
<220> FEATURE:
<223> OTHER INFORMATION: primer

<400> SEQUENCE: 38

```
aaatctcgag accaggacat ccgacttgc                                      29
```

<210> SEQ ID NO 39
<211> LENGTH: 41
<212> TYPE: DNA
<213> ORGANISM: artificial
<220> FEATURE:
<223> OTHER INFORMATION: primer

<400> SEQUENCE: 39

```
cacgactagt gtgaccgggt catttttttg ctatttattc c                        41
```

<210> SEQ ID NO 40
<211> LENGTH: 42
<212> TYPE: DNA
<213> ORGANISM: artificial
<220> FEATURE:
<223> OTHER INFORMATION: primer

<400> SEQUENCE: 40

```
aaattctaga taactgcggt agcactaaag ccgctgcctt ag                       42
```

<210> SEQ ID NO 41
<211> LENGTH: 31
<212> TYPE: DNA
<213> ORGANISM: artificial
<220> FEATURE:
<223> OTHER INFORMATION: primer

<400> SEQUENCE: 41

```
caatctcgag atggctgata aacaacgtaa g                                   31
```

<210> SEQ ID NO 42
<211> LENGTH: 37
<212> TYPE: DNA

<213> ORGANISM: artificial
<220> FEATURE:
<223> OTHER INFORMATION: primer

<400> SEQUENCE: 42
caatgaattc ttagtttta actgcagaag caaattc                     37

<210> SEQ ID NO 43
<211> LENGTH: 31
<212> TYPE: DNA
<213> ORGANISM: artificial
<220> FEATURE:
<223> OTHER INFORMATION: primer

<400> SEQUENCE: 43
ataactcgag gacaataggt gctttaatca c                          31

<210> SEQ ID NO 44
<211> LENGTH: 38
<212> TYPE: DNA
<213> ORGANISM: artificial
<220> FEATURE:
<223> OTHER INFORMATION: primer

<400> SEQUENCE: 44
cgacgatatc aggtgtaaaa taccatttat taaaatag                   38

<210> SEQ ID NO 45
<211> LENGTH: 30
<212> TYPE: DNA
<213> ORGANISM: artificial
<220> FEATURE:
<223> OTHER INFORMATION: primer

<400> SEQUENCE: 45
cattgatatc atgtctaacc gtttggatgg                            30

<210> SEQ ID NO 46
<211> LENGTH: 30
<212> TYPE: DNA
<213> ORGANISM: artificial
<220> FEATURE:
<223> OTHER INFORMATION: primer

<400> SEQUENCE: 46
catactgcag ctattgagca gtgtagccac                            30

<210> SEQ ID NO 47
<211> LENGTH: 29
<212> TYPE: DNA
<213> ORGANISM: artificial
<220> FEATURE:
<223> OTHER INFORMATION: primer

<400> SEQUENCE: 47
aaatctcgag tcagtggaga caatagtcg                             29

<210> SEQ ID NO 48
<211> LENGTH: 31
<212> TYPE: DNA
<213> ORGANISM: artificial
<220> FEATURE:
<223> OTHER INFORMATION: primer

<400> SEQUENCE: 48
aaatatcgat atgcgtaatt tcccagaaat c                          31

<210> SEQ ID NO 49
<211> LENGTH: 35
<212> TYPE: DNA
<213> ORGANISM: artificial
<220> FEATURE:
<223> OTHER INFORMATION: primer

<400> SEQUENCE: 49
cataaagctt atgaaattct atacttcaac gacag                35

<210> SEQ ID NO 50
<211> LENGTH: 27
<212> TYPE: DNA
<213> ORGANISM: artificial
<220> FEATURE:
<223> OTHER INFORMATION: primer

<400> SEQUENCE: 50
aaatgatatc ttaccaggcg aaagctc                27

<210> SEQ ID NO 51
<211> LENGTH: 31
<212> TYPE: DNA
<213> ORGANISM: artificial
<220> FEATURE:
<223> OTHER INFORMATION: primer

<400> SEQUENCE: 51
aaatatcgat ttattcaatg gtgtcaggct g                31

<210> SEQ ID NO 52
<211> LENGTH: 32
<212> TYPE: DNA
<213> ORGANISM: artificial
<220> FEATURE:
<223> OTHER INFORMATION: primer

<400> SEQUENCE: 52
ccaaaagctt atgaaaagat caaaacgatt tg                32

<210> SEQ ID NO 53
<211> LENGTH: 35
<212> TYPE: DNA
<213> ORGANISM: artificial
<220> FEATURE:
<223> OTHER INFORMATION: primer

<400> SEQUENCE: 53
gggtgatatc ttaaggtaaa gtaaagtcaa cccac                35

<210> SEQ ID NO 54
<211> LENGTH: 29
<212> TYPE: DNA
<213> ORGANISM: artificial
<220> FEATURE:
<223> OTHER INFORMATION: primer

<400> SEQUENCE: 54
aaatgaattc atgttaaacg gcctgaaac                29

<210> SEQ ID NO 55
<211> LENGTH: 31
<212> TYPE: DNA
<213> ORGANISM: artificial
<220> FEATURE:

```
<223> OTHER INFORMATION: primer

<400> SEQUENCE: 55
aaatggtacc gaactgagat tagccccgga c                                      31

<210> SEQ ID NO 56
<211> LENGTH: 34
<212> TYPE: DNA
<213> ORGANISM: artificial
<220> FEATURE:
<223> OTHER INFORMATION: primer

<400> SEQUENCE: 56
gttgtttatc agccatacca ggacatccga cttg                                   34

<210> SEQ ID NO 57
<211> LENGTH: 55
<212> TYPE: DNA
<213> ORGANISM: artificial
<220> FEATURE:
<223> OTHER INFORMATION: primer

<400> SEQUENCE: 57
ctgcgtgcaa tccatcttgt tcaatcattt agttttttaac tgcagaagca aattc           55

<210> SEQ ID NO 58
<211> LENGTH: 43
<212> TYPE: DNA
<213> ORGANISM: artificial
<220> FEATURE:
<223> OTHER INFORMATION: primer

<400> SEQUENCE: 58
gcaaaaaaat gacccggtca ctcagaagaa ctcgtcaaga agg                         43

<210> SEQ ID NO 59
<211> LENGTH: 42
<212> TYPE: DNA
<213> ORGANISM: artificial
<220> FEATURE:
<223> OTHER INFORMATION: primer

<400> SEQUENCE: 59
aaattctaga taactgcggt agcactaaag ccgctgcctt ac                          42

<210> SEQ ID NO 60
<211> LENGTH: 31
<212> TYPE: DNA
<213> ORGANISM: artificial
<220> FEATURE:
<223> OTHER INFORMATION: primer

<400> SEQUENCE: 60
aaatggtacc gaactgagat tagccccgga c                                      31

<210> SEQ ID NO 61
<211> LENGTH: 37
<212> TYPE: DNA
<213> ORGANISM: artificial
<220> FEATURE:
<223> OTHER INFORMATION: primer

<400> SEQUENCE: 61
gattaaagca cctattgtca ccaggacatc cgacttg                                37
```

```
<210> SEQ ID NO 62
<211> LENGTH: 56
<212> TYPE: DNA
<213> ORGANISM: artificial
<220> FEATURE:
<223> OTHER INFORMATION: primer

<400> SEQUENCE: 62
ctaccttacc atccaaacgg ttagacatag gtgtaaaata ccatttatta aaatag         56

<210> SEQ ID NO 63
<211> LENGTH: 45
<212> TYPE: DNA
<213> ORGANISM: artificial
<220> FEATURE:
<223> OTHER INFORMATION: primer

<400> SEQUENCE: 63
caatccatct tgttcaatca tctattgagc agtgtagcca ccgtc                     45

<210> SEQ ID NO 64
<211> LENGTH: 43
<212> TYPE: DNA
<213> ORGANISM: artificial
<220> FEATURE:
<223> OTHER INFORMATION: primer

<400> SEQUENCE: 64
gcaaaaaaat gacccggtca ctcagaagaa ctcgtcaaga agg                       43

<210> SEQ ID NO 65
<211> LENGTH: 42
<212> TYPE: DNA
<213> ORGANISM: artificial
<220> FEATURE:
<223> OTHER INFORMATION: primer

<400> SEQUENCE: 65
aaattctaga taactgcggt agcactaaag ccgctgcctt ac                        42

<210> SEQ ID NO 66
<211> LENGTH: 31
<212> TYPE: DNA
<213> ORGANISM: artificial
<220> FEATURE:
<223> OTHER INFORMATION: primer

<400> SEQUENCE: 66
aaatggtacc gaactgagat tagccccgga c                                    31

<210> SEQ ID NO 67
<211> LENGTH: 33
<212> TYPE: DNA
<213> ORGANISM: artificial
<220> FEATURE:
<223> OTHER INFORMATION: primer

<400> SEQUENCE: 67
tattgtctcc actgaaccag gacatccgac ttg                                  33

<210> SEQ ID NO 68
<211> LENGTH: 55
<212> TYPE: DNA
<213> ORGANISM: artificial
<220> FEATURE:
<223> OTHER INFORMATION: primer
```

```
<400> SEQUENCE: 68
ctgtcgttga agtatagaat ttcatatgcg taatttccca gaaatccaaa atacg          55

<210> SEQ ID NO 69
<211> LENGTH: 52
<212> TYPE: DNA
<213> ORGANISM: artificial
<220> FEATURE:
<223> OTHER INFORMATION: primer

<400> SEQUENCE: 69
ggttcagcct gacaccattg aataattacc aggcgaaagc tccagttgga gc             52

<210> SEQ ID NO 70
<211> LENGTH: 55
<212> TYPE: DNA
<213> ORGANISM: artificial
<220> FEATURE:
<223> OTHER INFORMATION: primer

<400> SEQUENCE: 70
gtggttgact ttactttacc ttaaatgaaa agatcaaaac gatttgcagt actgg          55

<210> SEQ ID NO 71
<211> LENGTH: 41
<212> TYPE: DNA
<213> ORGANISM: artificial
<220> FEATURE:
<223> OTHER INFORMATION: primer

<400> SEQUENCE: 71
caatccatct tgttcaatca tatgttaaac ggcctgaaac c                         41

<210> SEQ ID NO 72
<211> LENGTH: 43
<212> TYPE: DNA
<213> ORGANISM: artificial
<220> FEATURE:
<223> OTHER INFORMATION: primer

<400> SEQUENCE: 72
gcaaaaaaat gacccggtca ctcagaagaa ctcgtcaaga agg                       43

<210> SEQ ID NO 73
<211> LENGTH: 42
<212> TYPE: DNA
<213> ORGANISM: artificial
<220> FEATURE:
<223> OTHER INFORMATION: primer

<400> SEQUENCE: 73
aaattctaga taactgcggt agcactaaag ccgctgcctt ac                        42

<210> SEQ ID NO 74
<211> LENGTH: 305
<212> TYPE: DNA
<213> ORGANISM: artificial
<220> FEATURE:
<223> OTHER INFORMATION: promoter

<400> SEQUENCE: 74
agcagtttac agaggcgatt tatcggcggg taagactata cagtatcggg aaaaaattaa     60
gaacggtcaa agaatctgga catatcacaa cccacaatct agtattcaaa atccttctgc    120
ctggccttat ttggtcgtat ttacccattg tgcccaaatc cgaccattgt tgccaattat    180
```

-continued

```
tccccaggta accacggcga tcgccaagga aagatttaag tatttttcc cattctccct      240 aatcctgcgg ccaaggagct gggttaacgt tagggcaagt cggatgtcct ggtgtgaccg      300
ggtca                                                                  305
```

<210> SEQ ID NO 75
<211> LENGTH: 554
<212> TYPE: PRT
<213> ORGANISM: Lactococcus lactis

<400> SEQUENCE: 75

```
Met Ser Glu Lys Gln Phe Gly Ala Asn Leu Val Val Asp Ser Leu Ile
1               5                   10                  15

Asn His Lys Val Lys Tyr Val Phe Gly Ile Pro Gly Ala Lys Ile Asp
                20                  25                  30

Arg Val Phe Asp Leu Leu Glu Asn Glu Glu Gly Pro Gln Met Val Val
            35                  40                  45

Thr Arg His Glu Gln Gly Ala Ala Phe Met Ala Gln Ala Val Gly Arg
        50                  55                  60

Leu Thr Gly Glu Pro Gly Val Val Val Thr Ser Gly Pro Gly Val
65                  70                  75                  80

Ser Asn Leu Ala Thr Pro Leu Leu Thr Ala Thr Ser Glu Gly Asp Ala
                85                  90                  95

Ile Leu Ala Ile Gly Gly Gln Val Lys Arg Ser Asp Arg Leu Lys Arg
            100                 105                 110

Ala His Gln Ser Met Asp Asn Ala Gly Met Met Gln Ser Ala Thr Lys
        115                 120                 125

Tyr Ser Ala Glu Val Leu Asp Pro Asp Thr Leu Ser Glu Ser Ile Ala
    130                 135                 140

Asn Ala Tyr Arg Ile Ala Lys Ser Gly His Pro Gly Ala Thr Phe Leu
145                 150                 155                 160

Ser Ile Pro Gln Asp Val Thr Asp Ala Glu Val Ser Ile Lys Ala Ile
                165                 170                 175

Gln Pro Leu Ser Asp Pro Lys Met Gly Asn Ala Ser Ile Asp Asp Ile
            180                 185                 190

Asn Tyr Leu Ala Gln Ala Ile Lys Asn Ala Val Leu Pro Val Ile Leu
        195                 200                 205

Val Gly Ala Gly Ala Ser Asp Val Lys Val Ala Ser Ser Leu Arg Asn
    210                 215                 220

Leu Leu Thr His Val Asn Ile Pro Val Val Glu Thr Phe Gln Gly Ala
225                 230                 235                 240

Gly Val Ile Ser His Asp Leu Glu His Thr Phe Tyr Gly Arg Ile Gly
                245                 250                 255

Leu Phe Arg Asn Gln Pro Gly Asp Met Leu Leu Lys Arg Ser Asp Leu
            260                 265                 270

Val Ile Ala Val Gly Tyr Asp Pro Ile Glu Tyr Glu Ala Arg Asn Trp
        275                 280                 285

Asn Ala Glu Ile Asp Ser Arg Ile Ile Val Ile Asp Asn Ala Ile Ala
    290                 295                 300

Glu Ile Asp Thr Tyr Tyr Gln Pro Glu Arg Glu Leu Ile Gly Asp Ile
305                 310                 315                 320

Ala Ala Thr Leu Asp Asn Leu Leu Pro Ala Val Arg Gly Tyr Lys Ile
                325                 330                 335

Pro Lys Gly Thr Lys Glu Tyr Leu Asp Gly Leu His Glu Val Ala Glu
```

```
                340                 345                 350
Gln His Glu Phe Asp Thr Glu Asn Thr Glu Glu Gly Arg Met His Pro
                355                 360                 365

Leu Asp Leu Val Ser Thr Phe Gln Glu Ile Val Lys Asp Asp Glu Thr
    370                 375                 380

Val Thr Val Asp Val Gly Ser Leu Tyr Ile Trp Met Ala Arg His Phe
385                 390                 395                 400

Lys Ser Tyr Glu Pro Arg His Leu Leu Phe Ser Asn Gly Met Gln Thr
                405                 410                 415

Leu Gly Val Ala Leu Pro Trp Ala Ile Thr Ala Ala Leu Leu Arg Pro
            420                 425                 430

Gly Lys Lys Val Tyr Ser His Ser Gly Asp Gly Phe Leu Phe Thr
        435                 440                 445

Gly Gln Glu Leu Glu Thr Ala Val Arg Leu Asn Leu Pro Ile Val Gln
    450                 455                 460

Ile Ile Trp Asn Asp Gly His Tyr Asp Met Val Lys Phe Gln Glu Glu
465                 470                 475                 480

Met Lys Tyr Gly Arg Ser Ala Ala Val Asp Phe Gly Tyr Val Asp Tyr
                485                 490                 495

Val Lys Tyr Ala Glu Ala Met Gly Ala Thr Gly Tyr Arg Ala His Ser
            500                 505                 510

Lys Glu Glu Leu Ala Glu Ile Leu Lys Ser Ile Pro Asn Thr Thr Gly
        515                 520                 525

Pro Val Val Ile Asp Val Pro Leu Asp Tyr Ser Asp Asn Ile Lys Leu
    530                 535                 540

Ala Glu Lys Leu Leu Pro Glu Glu Phe Tyr
545                 550

<210> SEQ ID NO 76
<211> LENGTH: 1665
<212> TYPE: DNA
<213> ORGANISM: Lactococcus lactis

<400> SEQUENCE: 76
atgtctgaga  acaatttggg  ggcgaacttg  gttgtcgata  gtttgattaa  ccataaagtg    60
aagtatgtat  ttgggattcc  aggagcaaaa  attgaccggg  ttttgatttt  attagaaaat   120
gaagaaggcc  ctcaaatggt  cgtgactcgt  catgagcaag  gagctgcttt  catggctcaa   180
gcagttggcc  gtttgactgg  cgaacctggt  gtagtagttg  ttacgagtgg  tccaggggta   240
tcaaaccttg  caactccact  tttgactgca  acatcagaag  gtgacgctat  tttagccatt   300
ggtggacaag  ttaaacgcag  tgaccgtctc  aaacgtgcac  accaatcaat  ggataatgcc   360
ggaatgatgc  aatcagcaac  aaaatattca  gcagaagtac  ttgatcctga  tacactttct   420
gaatcaattg  ccaatgccta  tcgtattgcc  aaatcaggac  atccaggtgc  aactttcttg   480
tcaatccccc  aagatgtaac  ggatgccgaa  gtatcaatca  agccattca  accactttca   540 gaccctaaaa  tggggaatgc  ctctattgat  gacatcaatt  acctagcgca  agccatcaaa   600
aatgccgttt  tgccagtaat  tttggttgga  gctggagctt  cagatgtcaa  agtcgcttca   660
tcattgcgta  acttattgac  tcatgttaat  attcctgtcg  ttgaaacatt  ccaaggtgct   720
ggtgttattt  cacatgattt  agagcatact  ttttacggac  gtatcggtct  tttccgcaac   780
caaccagggg  atatgctttt  gaaacgctct  gaccttgtta  ttgctgttgg  ttacgaccca   840
atcgaatacg  aagctcgcaa  ctggaatgcc  gaaattgata  gccgcatcat  cgttattgat   900
```

-continued

```
aatgccattg ctgaaattga tacttactac caaccagaac gtgaattaat tggggacatc    960
gcggcaacat tggataatct tttaccagcc gttcgtggtt ataaaattcc aaaaggaaca   1020
aaagaatatc ttgatggcct tcatgaagtt gctgaacaac atgaattcga tactgaaaac   1080
accgaagaag gcagaatgca cccacttgat ttggtcagca ctttccaaga aatcgtcaaa   1140
gatgatgaaa cagtcacagt tgacgtaggt tcactataca tttggatggc acgtcatttc   1200
aaatcatacg aaccacgtca ccttctattc tcaaacggaa tgcaaacact tggtgttgca   1260
ctcccttggg caatcacagc cgcattgttg cgcccaggta agaaagttta ttctcactca   1320
ggtgatggag gtttcctctt cacaggtcaa gaactcgaaa cggccgttcg tttaaatctt   1380
ccaatcgttc aaatcatctg gaatgatggt cattacgaca tggtaaaatt ccaagaagaa   1440
atgaaatatg gacgttcagc agccgttgat ttcggttatg ttgattacgt aaaatatgct   1500
gaagcaatgg gagcaacagg ctaccgtgcc cacagcaaag aagaacttgc cgaaattcta   1560
aaatcaattc caaatactac aggtcctgta gtaattgatg tacctttgga ctactctgat   1620
aatattaagt tagcagaaaa attattgcca gaagaatttt actga                  1665
```

<210> SEQ ID NO 77
<211> LENGTH: 236
<212> TYPE: PRT
<213> ORGANISM: Lactococcus lactis

<400> SEQUENCE: 77

```
Met Ser Glu Ile Thr Gln Leu Phe Gln Tyr Asn Thr Leu Gly Ala Leu
1               5                   10                  15

Met Ala Gly Leu Tyr Glu Gly Thr Met Thr Ile Gly Glu Leu Leu Lys
            20                  25                  30

His Gly Asp Leu Gly Ile Gly Thr Leu Asp Ser Ile Asp Gly Glu Leu
        35                  40                  45

Ile Val Leu Asp Gly Lys Ala Tyr Gln Ala Lys Gly Asp Lys Thr Ile
    50                  55                  60

Val Glu Leu Thr Asp Asp Ile Lys Val Pro Tyr Ala Ala Val Val Pro
65                  70                  75                  80

His Gln Ala Glu Val Val Phe Lys Gln Lys Phe Thr Val Ser Asp Lys
                85                  90                  95

Glu Leu Glu Asp Arg Ile Glu Ser Tyr Phe Asp Gly Gln Asn Leu Phe
            100                 105                 110

Arg Ser Ile Lys Ile Thr Gly Lys Phe Pro Lys Met His Val Arg Met
        115                 120                 125

Ile Pro Arg Ala Lys Ser Gly Thr Lys Phe Val Glu Val Ser Gln Asn
    130                 135                 140

Gln Pro Glu Tyr Thr Glu Glu Asn Ile Lys Gly Thr Ile Val Gly Ile
145                 150                 155                 160

Trp Thr Pro Glu Met Phe His Gly Val Ser Val Ala Gly Tyr His Leu
                165                 170                 175

His Phe Ile Ser Glu Asp Phe Thr Phe Gly Gly His Val Leu Asp Phe
            180                 185                 190

Ile Ile Asp Asn Gly Thr Val Glu Ile Gly Ala Ile Asp Gln Leu Asn
        195                 200                 205

Gln Ser Phe Pro Val Gln Asp Arg Lys Phe Leu Phe Ala Asp Leu Asp
    210                 215                 220

Ile Glu Ala Leu Lys Lys Asp Ile Asp Val Ala Glu
225                 230                 235
```

<210> SEQ ID NO 78
<211> LENGTH: 711
<212> TYPE: DNA
<213> ORGANISM: Lactococcus lactis

<400> SEQUENCE: 78

```
atgtcagaaa tcacacaact tttcaatat aataccttg gggcattaat ggccggactt      60
tatgagggga caatgacgat tggtgagctc ttgaaacatg gtgacttagg aattggaact     120
ttagattcaa ttgatggtga attgattgtt ttagatggta aagcttatca agctaaggga    180
gataaaacga tcgtcgaatt aactgacgat atcaaagttc cttatgctgc agttgttcct    240
catcaggcag aagttgtttt caaacaaaaa tttacagtaa gcgataaaga attggaagac    300
cgaattgaaa gctattttga tggtcaaaac ttattccgct caatcaaaat tactggtaaa    360
tttccaaaaa tgcatgtacg aatgattccg cgtgctaaat caggaacaaa atttgtagaa    420
gtttcacaaa accaaccaga ataccgaa gaaaatatca aaggaacaat tgttggaatt     480
tggactcctg aaatgttcca tggtgtcagc gttgctggtt atcatcttca ttttattagt    540
gaagatttca cttttggtgg acatgttctt gatttattta tgataatgg actgttgaa    600
attggagcaa ttgaccaatt gaatcaatca ttccctgttc aagatcgcaa atttttattt    660
gccgaccttg acattgaggc tttgaaaaaa gatattgatg tagctgaatg a            711
```

<210> SEQ ID NO 79
<211> LENGTH: 253
<212> TYPE: PRT
<213> ORGANISM: Lactococcus lactis

<400> SEQUENCE: 79

```
Met Ser Lys Val Ala Ala Val Thr Gly Ala Gly Gln Gly Ile Gly Phe
1               5                   10                  15

Ala Ile Ala Lys Arg Leu Tyr Asn Asp Gly Phe Lys Val Ala Ile Ile
            20                  25                  30

Asp Tyr Asn Glu Glu Thr Ala Gln Gln Ala Ala Lys Glu Leu Gly Gly
        35                  40                  45

Glu Ser Phe Ala Leu Lys Ala Asp Val Ser Asp Arg Asp Gln Val Val
    50                  55                  60

Ala Ala Leu Glu Ala Val Val Glu Lys Phe Gly Asp Leu Asn Val Val
65                  70                  75                  80

Val Asn Asn Ala Gly Ile Ala Pro Thr Thr Pro Ile Glu Thr Ile Thr
                85                  90                  95

Pro Glu Gln Phe His Gln Val Tyr Asn Ile Asn Val Gly Gly Val Leu
            100                 105                 110

Trp Gly Thr Gln Ala Ala Thr Ala Leu Phe Arg Lys Leu Gly His Gly
        115                 120                 125

Gly Lys Ile Ile Asn Ala Thr Ser Gln Ala Gly Val Val Gly Asn Pro
    130                 135                 140

Asn Leu Met Leu Tyr Ser Ser Lys Phe Ala Val Arg Gly Met Thr
145                 150                 155                 160

Gln Ile Ala Ala Arg Asp Leu Ala Glu Glu Gly Ile Thr Val Asn Ala
                165                 170                 175

Tyr Ala Pro Gly Ile Val Lys Thr Pro Met Met Phe Asp Ile Ala His
            180                 185                 190

Gln Val Gly Lys Asn Ala Gly Lys Asp Asp Glu Trp Gly Met Gln Thr
        195                 200                 205
```

Phe Ala Lys Asp Ile Ala Met Lys Arg Leu Ser Glu Pro Glu Asp Val
              210                 215                 220

Ala Asn Val Val Ser Phe Leu Ala Gly Pro Asp Ser Asn Tyr Ile Thr
225                 230                 235                 240

Gly Gln Thr Ile Ile Val Asp Gly Gly Met Gln Phe His
              245                 250

<210> SEQ ID NO 80
<211> LENGTH: 763
<212> TYPE: DNA
<213> ORGANISM: Lactococcus lactis

<400> SEQUENCE: 80
atgtctaaag ttgcagcagt tactggcgca ggtcaaggaa ttggctttgc tatcgcaaaa      60
cgtttatata atgatgggtt taaagtcgca atcattgatt acaatgaaga aacagctcaa     120
caagcagcta aggaacttgg tggcgaatca tttgctctta aagcagatgt ttctgaccgt     180
gaccaagtag ttgccgcttt agaagctgtt gttgaaaaat tggtgatttg aatgtagta      240 gtaaataatg caggaatcgc cccaaccact ccgattgaaa caattactcc tgaacaattt     300
catcaagttt ataatattaa tgttggtgga gttttgtggg aacacaggc agccacagca      360 cttttccgta aactaggtca tggtggtaag attattaatg caacttcgca agcaggtgtc     420
gtagggaatc ctaacctaat gctttattct tcttcaaaat cgctgttcg tggaatgaca      480 caaattgccg ctcgcgatct agcagaagaa ggaattacag ttaatgccta tgcaccaggg     540
attgttaaaa caccaatgat gtttgatatt gcacatcaag tgggtaaaaa tgcaggtaaa     600
gatgacgaat ggggcatgca gacttttgcc aaagatatcg cgatgaaacg tttgtcagag     660
cctgaggacg tggccaatgt ggtttctttc cttgctggtc ctgattctaa ttatattacg     720
ggtcaaacaa ttattgttga tggtggaatg caatttcatt aag                      763

<210> SEQ ID NO 81
<211> LENGTH: 326
<212> TYPE: PRT
<213> ORGANISM: Lactococcus lactis

<400> SEQUENCE: 81

Met Ala Trp Cys Gly Ile Cys Gly Thr Asp Leu His Glu Phe Leu Asp
1               5                   10                  15

Gly Pro Ile Phe Cys Pro Ser Ala Glu His Pro Asn Pro Ile Thr Gly
              20                  25                  30

Glu Val Pro Pro Val Thr Leu Gly His Glu Met Ser Gly Ile Val Asn
          35                  40                  45

Phe Val Gly Gln Gly Val Ser Gly Leu Lys Val Gly Asp His Val Val
      50                  55                  60

Val Glu Pro Tyr Ile Val Pro Glu Gly Thr Asp Thr Ser Glu Thr Gly
65                  70                  75                  80

His Tyr Asn Leu Ser Glu Gly Asn Phe Ile Gly Leu Gly Gly Asn
              85                  90                  95

Gly Gly Gly Leu Ala Glu Lys Ile Ser Val Asp Glu Arg Trp Val His
              100                 105                 110

Lys Ile Pro Asp Asp Leu Pro Leu Asp Glu Ala Ala Leu Ile Glu Pro
              115                 120                 125

Leu Ser Val Gly Tyr His Ala Val Glu Arg Ala Asn Leu Ser Glu Lys
          130                 135                 140

Ser Thr Val Leu Val Val Gly Ala Gly Pro Ile Gly Leu Leu Thr Ala

```
                145                 150                 155                 160
Ala Val Ala Lys Ala Gln Gly His Thr Val Ile Ile Ser Glu Pro Ser
                165                 170                 175

Gly Leu Arg Arg Lys Ala Gln Glu Ala Glu Val Ala Asp Tyr Phe
                180                 185                 190

Phe Asn Pro Ile Glu Asp Asp Ile Gln Ala Lys Val His Gln Ile Asn
                195                 200                 205

Glu Lys Gly Val Asp Ala Ala Phe Glu Cys Thr Ser Val Gln Pro Gly
                210                 215                 220

Phe Asp Ala Cys Leu Asp Ser Ile Arg Met Gly Gly Thr Val Val Ile
225                 230                 235                 240

Val Ala Ile Trp Gly Lys Pro Ala Ser Val Asp Met Ala Lys Leu Val
                245                 250                 255

Ile Lys Glu Ala Asn Leu Leu Gly Thr Ile Ala Tyr Asn Asn Thr His
                260                 265                 270

Pro Lys Thr Ile Asp Leu Val Ala Thr Gly Lys Ile Lys Leu Asn Gln
                275                 280                 285

Phe Ile Thr Gly Lys Ile Gly Leu Asp Asp Leu Ile Asp Lys Gly Phe
                290                 295                 300

Asp Thr Leu Ile His His Asn Glu Thr Ala Val Lys Ile Leu Val Ser
305                 310                 315                 320

Pro Thr Gly Lys Gly Leu
                325

<210> SEQ ID NO 82
<211> LENGTH: 981
<212> TYPE: DNA
<213> ORGANISM: Lactococcus lactis

<400> SEQUENCE: 82
gtggcttggt gtggaatctg tggtacagat ttgcacgaat ttttagatgg accaattttt     60
tgtccatcag cagaacatcc aaatcctatt acaggtgaag ttccaccagt tactctcgga    120
catgaaatgt ctggtattgt aaactttgta ggtcaagggg taagtgggct caaagtaggt    180
gaccatgtcg ttgttgaacc ttatatcgtt cccgaaggta ctgatacaag tgaaactgga    240
cattacaatc tctcagaagg atcaaacttt attggtttgg gcggaaatgg cggcggtctg    300
gctgaaaaaa tttcagttga tgaacgttgg gtacataaaa ttcctgacga tttaccatta    360
gatgaagcag cactaattga accactttct gtgggatatc atgctgttga acgtgctaat    420
ttgagtgaaa agagtacggt actagttgtt ggagctggtc caatcggact tttgacagct    480
gcagttgcca agctcaaggg catacagta attattagtg agcctagtgg tttgcgtcgt    540
aaaaaagctc aagaagcaga agttgctgat tatttcttta tccaattga agatgatatt    600
caggcaaaag ttcatcaaat taatgaaaaa ggagttgatg ctgcttttga atgtacttct    660
gttcaaccag gatttgatgc gtgtttagat tctattcgca tgggtggaac agttgttatc    720
gttgcaattt ggggtaaacc agctagtgtt gacatggcaa aattagtcat taagaagct    780
aatctttag ggactattgc ttataataat actcatccta aaaccattga tttagttgca    840
actggtaaga ttaaattgaa tcaatttatt acaggtaaaa ttggcttaga tgacctgatt    900
gataaaggtt ttgatacttt gattcatcac aatgaaacag cagttaagat tttagtttca    960
ccaactggaa aaggtctata a                                              981

<210> SEQ ID NO 83
```

<211> LENGTH: 558
<212> TYPE: PRT
<213> ORGANISM: Klebsiella pneumoniae

<400> SEQUENCE: 83

```
Met Lys Arg Gln Lys Arg Phe Glu Glu Leu Glu Lys Arg Pro Ile His
1               5                   10                  15

Gln Asp Thr Phe Val Lys Glu Trp Pro Glu Glu Gly Phe Val Ala Met
            20                  25                  30

Met Gly Pro Asn Asp Pro Lys Pro Ser Val Lys Val Glu Asn Gly Lys
        35                  40                  45

Ile Val Glu Met Asp Gly Lys Lys Leu Glu Asp Phe Asp Leu Ile Asp
50                  55                  60

Leu Tyr Ile Ala Lys Tyr Gly Ile Asn Ile Asp Asn Val Glu Lys Val
65                  70                  75                  80

Met Asn Met Asp Ser Thr Lys Ile Ala Arg Met Leu Val Asp Pro Asn
                85                  90                  95

Val Ser Arg Asp Glu Ile Ile Glu Ile Thr Ser Ala Leu Thr Pro Ala
            100                 105                 110

Lys Ala Glu Glu Ile Ile Ser Lys Leu Asp Phe Gly Glu Met Ile Met
        115                 120                 125

Ala Val Lys Lys Met Arg Pro Arg Lys Pro Asp Asn Gln Cys His
130                 135                 140

Val Thr Asn Thr Val Asp Asn Pro Val Gln Ile Ala Ala Asp Ala Ala
145                 150                 155                 160

Asp Ala Ala Leu Arg Gly Phe Pro Glu Gln Glu Thr Thr Thr Ala Val
                165                 170                 175

Ala Arg Tyr Ala Pro Phe Asn Ala Ile Ser Ile Leu Ile Gly Ala Gln
            180                 185                 190

Thr Gly Arg Pro Gly Val Leu Thr Gln Cys Ser Val Glu Glu Ala Thr
        195                 200                 205

Glu Leu Gln Leu Gly Met Arg Gly Phe Thr Ala Tyr Ala Glu Thr Ile
210                 215                 220

Ser Val Tyr Gly Thr Asp Arg Val Phe Thr Asp Gly Asp Asp Thr Pro
225                 230                 235                 240

Trp Ser Lys Gly Phe Leu Ala Ser Cys Tyr Ala Ser Arg Gly Leu Lys
                245                 250                 255

Met Arg Phe Thr Ser Gly Ala Gly Ser Glu Val Leu Met Gly Tyr Pro
            260                 265                 270

Glu Gly Lys Ser Met Leu Tyr Leu Glu Ala Arg Cys Ile Leu Leu Thr
        275                 280                 285

Lys Ala Ser Gly Val Gln Gly Leu Gln Asn Gly Ala Val Ser Cys Ile
290                 295                 300

Glu Ile Pro Gly Ala Val Pro Asn Gly Ile Arg Glu Val Leu Gly Glu
305                 310                 315                 320

Asn Leu Leu Cys Met Met Cys Asp Ile Glu Cys Ala Ser Gly Cys Asp
                325                 330                 335

Gln Ala Tyr Ser His Ser Asp Met Arg Arg Thr Glu Arg Phe Ile Gly
            340                 345                 350

Gln Phe Ile Ala Gly Thr Asp Tyr Ile Asn Ser Gly Tyr Ser Ser Thr
        355                 360                 365

Pro Asn Tyr Asp Asn Thr Phe Ala Gly Ser Asn Thr Asp Ala Met Asp
370                 375                 380

Tyr Asp Asp Met Tyr Val Met Glu Arg Asp Leu Gly Gln Tyr Tyr Gly
```

-continued

```
385                 390                 395                 400
Ile His Pro Val Lys Glu Thr Ile Ile Lys Ala Arg Asn Lys Ala
                405                 410                 415

Ala Lys Ala Leu Gln Ala Val Phe Glu Asp Leu Gly Leu Pro Lys Ile
                420                 425                 430

Thr Asp Glu Val Glu Ala Thr Tyr Ala Asn Thr His Asp Asp
                435                 440                 445

Met Pro Lys Arg Asp Met Val Ala Asp Met Lys Ala Ala Gln Asp Met
    450                 455                 460

Met Asp Arg Gly Ile Thr Ala Ile Asp Ile Lys Ala Leu Tyr Asn
465                 470                 475                 480

His Gly Phe Lys Asp Val Ala Glu Ala Ile Leu Asn Leu Gln Lys Gln
                485                 490                 495

Lys Val Val Gly Asp Tyr Leu Gln Thr Ser Ile Phe Asp Lys Asp
                500                 505                 510

Trp Asn Val Thr Ser Ala Val Asn Asp Gly Asn Asp Tyr Gln Gly Pro
                515                 520                 525

Gly Thr Gly Tyr Arg Leu Tyr Glu Asp Lys Glu Glu Trp Asp Arg Ile
    530                 535                 540

Lys Asp Leu Pro Phe Ala Leu Asp Pro Glu His Leu Glu Leu
545                 550                 555
```

<210> SEQ ID NO 84
<211> LENGTH: 236
<212> TYPE: PRT
<213> ORGANISM: Klebsiella pneumoniae

<400> SEQUENCE: 84

```
Met Ala Asp Ile Asp Glu Asn Leu Leu Arg Lys Ile Val Lys Glu Val
1               5                   10                  15

Leu Ser Glu Thr Asn Gln Ile Asp Thr Lys Ile Asp Phe Asp Lys Ser
                20                  25                  30

Asn Asp Ser Thr Ala Thr Ala Thr Gln Glu Val Gln Gln Pro Asn Ser
            35                  40                  45

Lys Ala Val Pro Glu Lys Lys Leu Asp Trp Phe Gln Pro Val Gly Glu
 50                 55                  60

Ala Lys Pro Gly Tyr Ser Lys Asp Glu Val Val Ile Ala Val Gly Pro
65                  70                  75                  80

Ala Phe Ala Thr Val Leu Asp Lys Thr Glu Thr Gly Ile Pro His Lys
                85                  90                  95

Glu Val Leu Arg Gln Val Ile Ala Gly Ile Glu Glu Gly Leu Lys
                100                 105                 110

Ala Arg Val Val Lys Val Tyr Arg Ser Ser Asp Val Ala Phe Cys Ala
            115                 120                 125

Val Gln Gly Asp His Leu Ser Gly Ser Gly Ile Ala Ile Gly Ile Gln
130                 135                 140

Ser Lys Gly Thr Thr Val Ile His Gln Lys Asp Gln Asp Pro Leu Gly
145                 150                 155                 160

Asn Leu Glu Leu Phe Pro Gln Ala Pro Val Leu Thr Pro Glu Thr Tyr
                165                 170                 175

Arg Ala Ile Gly Lys Asn Ala Ala Met Tyr Ala Lys Gly Glu Ser Pro
            180                 185                 190

Glu Pro Val Pro Ala Lys Asn Asp Gln Leu Ala Arg Ile His Tyr Gln
        195                 200                 205
```

Ala Ile Ser Ala Ile Met His Ile Arg Glu Thr His Gln Val Val Val
    210                 215                 220

Gly Lys Pro Glu Glu Glu Ile Lys Val Thr Phe Asp
225                 230                 235

<210> SEQ ID NO 85
<211> LENGTH: 171
<212> TYPE: PRT
<213> ORGANISM: Klebsiella pneumoniae

<400> SEQUENCE: 85

Met Ser Glu Val Asp Asp Leu Val Ala Lys Ile Met Ala Gln Met Gly
1               5                   10                  15

Asn Ser Ser Ala Asn Ser Ser Thr Gly Thr Ser Thr Ala Ser Thr
            20                  25                  30

Ser Lys Glu Met Thr Ala Asp Asp Tyr Pro Leu Tyr Gln Lys His Arg
        35                  40                  45

Asp Leu Val Lys Thr Pro Lys Gly His Asn Leu Asp Asp Ile Asn Leu
    50                  55                  60

Gln Lys Val Val Asn Asn Gln Val Asp Pro Lys Glu Leu Arg Ile Thr
65                  70                  75                  80

Pro Glu Ala Leu Lys Leu Gln Gly Glu Ile Ala Ala Asn Ala Gly Arg
                85                  90                  95

Pro Ala Ile Gln Lys Asn Leu Gln Arg Ala Ala Glu Leu Thr Arg Val
            100                 105                 110

Pro Asp Glu Arg Val Leu Glu Met Tyr Asp Ala Leu Arg Pro Phe Arg
        115                 120                 125

Ser Thr Lys Gln Glu Leu Leu Asn Ile Ala Lys Glu Leu Arg Asp Lys
    130                 135                 140

Tyr Asp Ala Asn Val Cys Ala Ala Trp Phe Glu Ala Ala Asp Tyr
145                 150                 155                 160

Tyr Glu Ser Arg Lys Lys Leu Lys Gly Asp Asn
                165                 170

<210> SEQ ID NO 86
<211> LENGTH: 1677
<212> TYPE: DNA
<213> ORGANISM: Klebsiella pneumoniae

<400> SEQUENCE: 86
atgaaacgtc aaaaacgatt tgaagaacta gaaaaacggc caattcatca agatacattt    60
gttaaagaat ggccagaaga aggtttcgtt gcaatgatgg ggcctaatga ccctaagcct   120
agtgtaaaag ttgaaaatgg caagatcgta gagatggatg gtaaaaagct cgaagatttt   180
gatttgattg acttgtacat tgctaagtat ggaatcaata ttgacaacgt tgaaaaagtt   240
atgaatatgg attctaccaa gattgcacgg atgcttgttg atcctaatgt ttctcgtgat   300
gaaattattg aaattacatc agctttgact cctgctaagg ctgaagagat catcagtaag   360
cttgattttg gtgaaatgat tatggctgtc aagaagatgc gcccacgtcg taagcctgac   420
aaccagtgtc acgttaccaa tactgttgat aacccagttc aaattgctgc tgatgctgct   480
gatgccgctc ttcgtggatt tccagaacaa gaaccacga cagctgtggc acgttatgca   540
ccattcaatg ctatttcaat tttaattggt gcacaaacag tcgccctgg tgtattgaca   600 caatgttctg ttgaagaagc tactgaattg caattaggta tgcgtggttt taccgcatat   660
gctgaaacca tttcagttta cggtactgat cgtgtattta ccgatggtga tgatactcca   720

| | |
|---|---|
| tggtctaaag gcttcttggc atcttgttat gcatcacgtg gtttgaagat gcgatttact | 780 |
| tcaggtgccg gttcagaagt tttgatgggt tatccagaag gtaagtcaat gctttacctt | 840 |
| gaagcgcgtt gtattttact tactaaggct tcaggtgttc aaggacttca aaatggtgcc | 900 |
| gtaagttgta ttgaaattcc tggtgctgtt cctaatggta ttcgtgaagt tctcggtgaa | 960 |
| aacttgttat gtatgatgtg tgacatcgaa tgtgcttctg gttgtgacca agcatactca | 1020 |
| cactccgata tgcggcggac tgaacggttt attggtcaat ttattgccgg tactgattat | 1080 |
| attaactctg gttactcatc aactcctaac tacgataata ccttcgctgg ttcaaacact | 1140 |
| gatgctatgg actacgatga tatgtatgtt atggaacgtg acttgggtca atattatggt | 1200 |
| attcaccctg ttaaggaaga aaccattatt aaggcacgta ataaggccgc taaagcccctt | 1260 |
| caagcagtat ttgaagatct tggattacca aagattactg atgaagaggt cgaagcagca | 1320 |
| acgtatgcta cacccatga tgcatgcca aagcgggata tggttgcaga tatgaaggct | 1380 |
| gctcaagata tgatggatcg tggaattact gctattgata ttatcaaggc attgtacaac | 1440 |
| cacggattta aagatgtcgc tgaagcaatt ttgaaccttc aaaaacaaaa agttgttggt | 1500 |
| gattaccttc aaacatcttc tattttttgat aaagattgga acgtcacttc tgctgttaac | 1560 |
| gacgaaaatg attatcaagg accaggtact ggataccgtc tatatgaaga caaggaagaa | 1620 |
| tgggatcgga ttaaagactt accattcgcc cttgatccag aacatttgga actgtag | 1677 |

<210> SEQ ID NO 87
<211> LENGTH: 711
<212> TYPE: DNA
<213> ORGANISM: Klebsiella pneumoniae

<400> SEQUENCE: 87

| | |
|---|---|
| atggctgata ttgatgaaaa cttattacgt aaaatcgtta aagaagtttt aagcgaaact | 60 |
| aatcaaatcg atactaagat tgactttgat aaaagtaatg atagtactgc aacagcaact | 120 |
| caagaggtgc aacaaccaaa tagtaaagct gttccagaaa agaaacttga ctggttccaa | 180 |
| ccagttggag aagcaaaacc tggatattct aaggatgaag ttgtaattgc agtcggtcct | 240 |
| gcattcgcaa ctgttcttga taagacagaa actggtattc ctcataaaga agtgcttcgt | 300 |
| caagttattg ctggtattga agaagaaggg cttaaggcgc gggtagttaa agtttaccgg | 360 |
| agttcagatg tagcattctg tgctgtccaa ggtgatcacc tttctggttc aggaattgct | 420 |
| attggtatcc aatcaaaagg gacgacagtt attcaccaaa aggatcaaga ccctcttggt | 480 |
| aaccttgagt tattcccaca gcgccagta cttactcccg aaacttatcg tgcaattggt | 540 |
| aagaatgccg ctatgtatgc taagggtgaa tctccagaac cagttccagc taaaaacgat | 600 |
| caacttgctc gtattcacta tcaagctatt tcagcaatta tgcatattcg tgaaactcac | 660 |
| caagttgttg ttggtaagcc tgaagaagaa attaaggtta cgtttgatta a | 711 |

<210> SEQ ID NO 88
<211> LENGTH: 516
<212> TYPE: DNA
<213> ORGANISM: Klebsiella pneumoniae

<400> SEQUENCE: 88

| | |
|---|---|
| atgagtgaag ttgatgattt agtagcaaag atcatggctc agatgggaaa cagttcatct | 60 |
| gctaatagct ctacaggtac ttcaactgca agtactagta aggaaatgac agcagatgat | 120 |
| tacccacttt atcaaaagca ccgtgattta gtaaaaacac caaaggaca caatcttgat | 180 |
| gacatcaatt tacaaaaagt agtaaataat caagttgatc ctaaggaatt acggattaca | 240 |

```
ccagaagcat tgaaacttca aggtgaaatt gcagctaatg ctggccgtcc agctattcaa    300
aagaatcttc aacgagctgc agaattaaca cgagtacctg acgaacgggt tcttgaaatg    360
tatgatgcat tgcgtccttt ccgttcaact aagcaagaat tattgaacat tgcaaaggaa    420
ttacgggaca gtatgacgc taatgtttgc gcagcatggt ttgaagaagc tgctgattat    480
tatgaaagtc gtaagaagct aaagggcgat aactaa                             516

<210> SEQ ID NO 89
<211> LENGTH: 390
<212> TYPE: PRT
<213> ORGANISM: Klebsiella pneumoniae

<400> SEQUENCE: 89
```

Met Ala Glu Arg Ser Tyr Asp Phe Leu Met Pro Ser Val Asn Phe Phe
 1               5                  10                  15

Gly Pro Gly Val Ile Ser Lys Ile Gly Asp Arg Ala Lys Met Leu Gly
            20                  25                  30

Met Lys Lys Pro Val Ile Val Thr Asp Lys Phe Leu Glu Gly Leu Lys
        35                  40                  45

Asp Gly Ala Val Glu Gln Thr Leu Asp Ser Leu Lys Ala Ala Gly Val
    50                  55                  60

Asp Tyr Val Val Tyr Asn Asn Val Glu Pro Asn Pro Lys Ile Arg Asn
65                  70                  75                  80

Ile Lys Glu Val Lys Lys Leu Tyr Glu Glu Ser Gly Ala Asp Ser Ile
                85                  90                  95

Ile Thr Val Gly Gly Gly Ser Ala His Asp Thr Gly Lys Gly Ala Gly
            100                 105                 110

Ile Ile Leu Thr Asn Gly Asp Asp Ile Thr Lys Leu Ala Gly Ile Glu
        115                 120                 125

Thr Leu Asp Lys Ala Leu Pro Pro Leu Ile Ala Val Asn Thr Thr Ala
    130                 135                 140

Gly Thr Gly Ser Glu Leu Thr Arg His Ala Val Ile Thr Asn Glu Glu
145                 150                 155                 160

Thr His Leu Lys Phe Val Val Ser Trp Arg Asn Ile Pro Leu Val
                165                 170                 175

Ser Phe Asn Asp Pro Thr Leu Met Leu Asp Val Pro Lys Gly Leu Thr
            180                 185                 190

Ala Ala Thr Gly Met Asp Ala Phe Val Gln Ala Val Glu Pro Tyr Val
        195                 200                 205

Ser Val Asp His Asn Pro Ile Thr Asp Ser Gln Cys Val Glu Ala Ile
    210                 215                 220

Lys Leu Ile Glu Thr Ser Leu Arg Glu Ala Val Ala Asn Gly His Asn
225                 230                 235                 240

Leu Asp Ala Arg Thr Lys Met Val Glu Ala Glu Met Leu Ala Gly Met
                245                 250                 255

Ala Phe Asn Asn Ala Asn Leu Gly Tyr Val His Ala Met Ala His Gln
            260                 265                 270

Leu Gly Gly Gln Tyr Asp Ala Pro His Gly Val Cys Cys Ala Leu Leu
        275                 280                 285

Leu Pro Tyr Val Glu Glu Tyr Asn Ile Ile Ala Cys Pro Asp Arg Phe
    290                 295                 300

Ala Gln Leu Ala Glu Ile Met Gly Glu Asn Thr Glu Gly Leu Ser Thr
305                 310                 315                 320

Arg Asp Ala Ala Glu Leu Ala Ile Lys Ala Met Lys Gln Leu Ser Glu
            325                 330                 335

Asp Val Gly Ile Pro His Ser Ile Lys Glu Ile Gly Ala Lys Pro Glu
        340                 345                 350

Asp Phe Glu Leu Met Ala Glu Asn Ala Leu Lys Asp Gly Asn Ala Phe
    355                 360                 365

Ser Asn Pro Arg Lys Gly Thr Lys Glu Asp Ile Ile Lys Ile Phe Gln
370                 375                 380

Ala Ala Tyr Asp Ala Glu
385                 390

<210> SEQ ID NO 90
<211> LENGTH: 1122
<212> TYPE: DNA
<213> ORGANISM: Klebsiella pneumoniae

<400> SEQUENCE: 90
atggaaaaat tttcactcgc aacaaccatc tattcgggta atgatagcct agaacggtta     60
cggttgctaa aaaagaaac tattttatg gtatgcgatg catttttgcc ggatacgccc      120
acgttgaaac ggatcttgtc agaaattggt gatactaatc aagtgaccat cttctctgat    180
gtgaagcctg atccaccatt ggctaacatc attgaagggg tcaaacaatt tgtcccactc    240
aagccaacta ttgtgattgg gattggtggc ggctcagcta ttgataccgc caagggaatt    300
cgcttctttg gtgaaaagtt gttgaaacaa gacatccaca gtttattgc cattccaacg    360 acgagtggaa ctggatcaga aattacgcaa cactgtgtgc gtcggatcc ggaacaccaa     420 caaaagtacc ccattatgga agactttttg cggccagacg aagcattgtt agatccacaa    480
ttggtgatga cggcgcctaa gagtgtgacg gcatactctg gcttggatgt gttgacacat    540
tcgctggaat cactagttgc ggttgatgcc aacacgatta cggacggctt ggccgaaaag    600
ggcgtcgatg ttatagcgca tgatttggta acttgttacc ggcatggtga tgatgaggcg    660
gctcgtaagc gcgtgcacga gatttcttgt gccgccggaa tttctttcag taatgccggc    720
ctaggtatct gtcattcgat tgctcaccaa cttggggcaa acttccatgt gccgcatgga    780
ttagctaatg cgatgctctt gccatacgtg gtgagctaca atgctagcaa gtctaaggtc    840
gcttgtgcta agtacgcaca ggccgcccgt aaagctggat tggcctctca aggtatgggt    900
gatcgagttg cggttcgacg cttaatcagt tgcattcggc aaatgatgtt acagatggga    960
tgtcctcgga ccctgcaagc ctttggcatt gatgtcaaag acgctgcagc taaggtcgat    1020
gtgattgtgg ctaatgccaa aaaggatgcc accttccctg taatccagt tgtgccatct    1080 gatgatgatt tagctgaaat ttaccaacac gtgattaagt ag                       1122

<210> SEQ ID NO 91
<211> LENGTH: 350
<212> TYPE: PRT
<213> ORGANISM: Pseudomonas syringiae

<400> SEQUENCE: 91

Met Thr Asn Leu Gln Thr Phe Glu Leu Pro Thr Glu Val Thr Gly Cys
1               5                   10                  15

Ala Ala Asp Ile Ser Leu Gly Arg Ala Leu Ile Gln Ala Trp Gln Lys
            20                  25                  30

Asp Gly Ile Phe Gln Ile Lys Thr Asp Ser Glu Gln Asp Arg Lys Thr
        35                  40                  45

Gln Glu Ala Met Ala Ala Ser Lys Gln Phe Cys Lys Glu Pro Leu Thr

```
            50                  55                  60
Phe Lys Ser Ser Cys Val Ser Asp Leu Thr Tyr Ser Gly Tyr Val Ala
 65                  70                  75                  80

Ser Gly Glu Glu Val Thr Ala Gly Lys Pro Asp Phe Pro Glu Ile Phe
                 85                  90                  95

Thr Val Cys Lys Asp Leu Ser Val Gly Asp Gln Arg Val Lys Ala Gly
             100                 105                 110

Trp Pro Cys His Gly Pro Val Pro Trp Pro Asn Asn Thr Tyr Gln Lys
         115                 120                 125

Ser Met Lys Thr Phe Met Glu Glu Leu Gly Leu Ala Gly Glu Arg Leu
     130                 135                 140

Leu Lys Leu Thr Ala Leu Gly Phe Glu Leu Pro Ile Asn Thr Phe Thr
145                 150                 155                 160

Asp Leu Thr Arg Asp Gly Trp His His Met Arg Val Leu Arg Phe Pro
                165                 170                 175

Pro Gln Thr Ser Thr Leu Ser Arg Gly Ile Gly Ala His Thr Asp Tyr
            180                 185                 190

Gly Leu Leu Val Ile Ala Ala Gln Asp Asp Val Gly Gly Leu Tyr Ile
        195                 200                 205

Arg Pro Pro Val Glu Gly Glu Lys Arg Asn Arg Asn Trp Leu Pro Gly
    210                 215                 220

Glu Ser Ser Ala Gly Met Phe Glu His Asp Glu Pro Trp Thr Phe Val
225                 230                 235                 240

Thr Pro Thr Pro Gly Val Trp Thr Val Phe Pro Gly Asp Ile Leu Gln
                245                 250                 255

Phe Met Thr Gly Gly Gln Leu Leu Ser Thr Pro His Lys Val Lys Leu
            260                 265                 270

Asn Thr Arg Glu Arg Phe Ala Cys Ala Tyr Phe His Glu Pro Asn Phe
        275                 280                 285

Glu Ala Ser Ala Tyr Pro Leu Phe Glu Pro Ser Ala Asn Glu Arg Ile
    290                 295                 300

His Tyr Gly Glu His Phe Thr Asn Met Phe Met Arg Cys Tyr Pro Asp
305                 310                 315                 320

Arg Ile Thr Thr Gln Arg Ile Asn Lys Glu Asn Arg Leu Ala His Leu
                325                 330                 335

Glu Asp Leu Lys Lys Tyr Ser Asp Thr Arg Ala Thr Gly Ser
            340                 345                 350

<210> SEQ ID NO 92
<211> LENGTH: 1053
<212> TYPE: DNA
<213> ORGANISM: Pseudomonas syringiae

<400> SEQUENCE: 92
atgaccaact tgcaaacctt tgaattgccc accgaagtga ccggctgtgc ggcggatatc      60
agcttgggcc gcgccttgat tcaagcctgg caaaaagatg cattttca   aattaaaacc     120 gattccgaac aagatcgcaa aacccaagaa gccatggccg cctccaaaca attttgtaaa     180
gaacccttga cctttaaatc ctcctgtgtg tccgatttga cctactccgg ctacgtggcc     240
tccggcgaag aagtgaccgc tggcaagccc gacttccccg aaatctttac cgtgtgtaaa     300
gatttgtccg tgggcgatca acgcgtgaaa gccggctggc cctgtcacgg ccccgtgcca     360
tggcccaaca cacctacca  aaaatccatg aaaacctta  tggaagaatt gggcttggcc     420
ggcgaacgct tgttgaaatt gaccgccttg ggctttgaat tgcccattaa caccttacc     480
```

```
gatttgaccc gcgatggctg gcaccacatg agggttttgc gcttcccccc ccagacctcc    540
accttgtccc gcggcattgg cgcccacacc gattacggct tgttggtgat tgccgcccaa    600
gatgatgtgg gcggcttgta cattcgcccc ccgtggaag gcgaaaaacg caaccgcaac    660
tggttgcccg gcgaatcctc ggcgggcatg ttcgaacacg acgaaccctg gacctttgtg    720 accccaccc ccggcgtgtg gaccgtgttt cccggcgata ttttgcaatt tatgaccggc    780
ggccaattgt tgtccacccc ccacaaagtg aaattgaaca cccgcgaacg ctttgcctgt    840
gcctactttc acgaacccaa ctttgaagcc tccgcctacc ccttgtttga accctccgcc    900
aacgaacgca ttcactacgg cgaacacttt accaacatgt ttatgcgctg ttaccccgat    960
cgcattacca cccaacgcat taacaaagaa aaccgcttgg cccacttgga agatttgaaa   1020
aaatactccg ataccgcgc caccggctcc taa                                1053
```

<210> SEQ ID NO 93
<211> LENGTH: 28
<212> TYPE: DNA
<213> ORGANISM: artificial
<220> FEATURE:
<223> OTHER INFORMATION: primer

<400> SEQUENCE: 93
aaataagctt aaggagacta gcatgacc    28

<210> SEQ ID NO 94
<211> LENGTH: 24
<212> TYPE: DNA
<213> ORGANISM: artificial
<220> FEATURE:
<223> OTHER INFORMATION: primer

<400> SEQUENCE: 94
taaagaattc ttaggagccg gtgg    24

<210> SEQ ID NO 95
<211> LENGTH: 218
<212> TYPE: PRT
<213> ORGANISM: Clostridium acetobytilicum

<400> SEQUENCE: 95

Met Asn Ser Lys Ile Ile Arg Phe Glu Asn Leu Arg Ser Phe Phe Lys
1               5                   10                  15

Asp Gly Met Thr Ile Met Ile Gly Gly Phe Leu Asn Cys Gly Thr Pro
            20                  25                  30

Thr Lys Leu Ile Asp Phe Leu Val Asn Leu Asn Ile Lys Asn Leu Thr
        35                  40                  45

Ile Ile Ser Asn Asp Thr Cys Tyr Pro Asn Thr Gly Ile Gly Lys Leu
    50                  55                  60

Ile Ser Asn Asn Gln Val Lys Lys Leu Ile Ala Ser Tyr Ile Gly Ser
65                  70                  75                  80

Asn Pro Asp Thr Gly Lys Lys Leu Phe Asn Asn Glu Leu Glu Val Glu
                85                  90                  95

Leu Ser Pro Gln Gly Thr Leu Val Glu Arg Ile Arg Ala Gly Gly Ser
            100                 105                 110

Gly Leu Gly Gly Val Leu Thr Lys Thr Gly Leu Gly Thr Leu Ile Glu
        115                 120                 125

Lys Gly Lys Lys Lys Ile Ser Ile Asn Gly Thr Glu Tyr Leu Leu Glu
    130                 135                 140

Leu Pro Leu Thr Ala Asp Val Ala Leu Ile Lys Gly Ser Ile Val Asp
145                 150                 155                 160

Glu Ala Gly Asn Thr Phe Tyr Lys Gly Thr Thr Lys Asn Phe Asn Pro
            165                 170                 175

Tyr Met Ala Met Ala Ala Lys Thr Val Ile Val Glu Ala Glu Asn Leu
        180                 185                 190

Val Ser Cys Glu Lys Leu Glu Lys Glu Lys Ala Met Thr Pro Gly Val
            195                 200                 205

Leu Ile Asn Tyr Ile Val Lys Glu Pro Ala
        210                 215

<210> SEQ ID NO 96
<211> LENGTH: 221
<212> TYPE: PRT
<213> ORGANISM: Clostridium acetobytilicum

<400> SEQUENCE: 96

Met Ile Asn Asp Lys Asn Leu Ala Lys Glu Ile Ala Lys Arg Val
1               5                   10                  15

Ala Arg Glu Leu Lys Asn Gly Gln Leu Val Asn Leu Gly Val Gly Leu
            20                  25                  30

Pro Thr Met Val Ala Asp Tyr Ile Pro Lys Asn Phe Lys Ile Thr Phe
        35                  40                  45

Gln Ser Glu Asn Gly Ile Val Gly Met Gly Ala Ser Pro Lys Ile Asn
    50                  55                  60

Glu Ala Asp Lys Asp Val Val Asn Ala Gly Gly Asp Tyr Thr Thr Val
65                  70                  75                  80

Leu Pro Asp Gly Thr Phe Phe Asp Ser Ser Val Ser Phe Ser Leu Ile
                85                  90                  95

Arg Gly Gly His Val Asp Val Thr Val Leu Gly Ala Leu Gln Val Asp
            100                 105                 110

Glu Lys Gly Asn Ile Ala Asn Trp Ile Val Pro Gly Lys Met Leu Ser
        115                 120                 125

Gly Met Gly Gly Ala Met Asp Leu Val Asn Gly Ala Lys Lys Val Ile
    130                 135                 140

Ile Ala Met Arg His Thr Asn Lys Gly Gln Pro Lys Ile Leu Lys Lys
145                 150                 155                 160

Cys Thr Leu Pro Leu Thr Ala Lys Ser Gln Ala Asn Leu Ile Val Thr
                165                 170                 175

Glu Leu Gly Val Ile Glu Val Ile Asn Asp Gly Leu Leu Leu Thr Glu
            180                 185                 190

Ile Asn Lys Asn Thr Thr Ile Asp Glu Ile Arg Ser Leu Thr Ala Ala
        195                 200                 205

Asp Leu Leu Ile Ser Asn Glu Leu Arg Pro Met Ala Val
    210                 215                 220

<210> SEQ ID NO 97
<211> LENGTH: 657
<212> TYPE: DNA
<213> ORGANISM: Clostridium acetobytilicum

<400> SEQUENCE: 97
atgaactcta aaataattag atttgaaaat ttaaggtcat tctttaaaga tgggatgaca      60
attatgattg gaggtttttt aaactgtggc actccaacca aattaattga tttttagtt     120 aatttaaata taaagaattt aacgattata agtaatgata catgttatcc taatacaggt    180

```
attggtaagt taatatcaaa taatcaagta aaaaagctta ttgcttcata tataggcagc    240
aacccagata ctggcaaaaa acttttaat aatgaacttg aagtagagct ctctccccaa    300
ggaactctag tggaaagaat acgtgcaggc ggatctggct taggtggtgt actaactaaa    360
acaggtttag gaactttgat tgaaaaagga agaaaaaaa tatctataaa tggaacggaa    420
tatttgttag agctacctct tacagccgat gtagcattaa ttaaaggtag tattgtagat    480
gaggccggaa acaccttcta taaaggtact actaaaaact ttaatcccta tatggcaatg    540
gcagctaaaa ccgtaatagt tgaagctgaa aatttagtta gctgtgaaaa actagaaaag    600
gaaaaagcaa tgaccccggg agttcttata aattatatag taaaggagcc tgcataa      657
```

<210> SEQ ID NO 98
<211> LENGTH: 666
<212> TYPE: DNA
<213> ORGANISM: Clostridium acetobytilicum

<400> SEQUENCE: 98

```
atgattaatg ataaaaacct agcgaaagaa ataatagcca aaagagttgc aagagaatta     60
aaaaatggtc aacttgtaaa cttaggtgta ggtcttccta ccatggttgc agattatata    120
ccaaaaaatt tcaaaattac tttccaatca gaaaacggaa tagttggaat gggcgctagt    180
cctaaaataa atgaggcaga taagatgta gtaaatgcag gaggagacta tacaacagta    240
cttcctgacg gcacattttt cgatagctca gtttcgtttt cactaatccg tggtggtcac    300
gtagatgtta ctgttttagg ggctctccag gtagatgaaa agggtaatat agccaattgg    360
attgttcctg gaaaaatgct ctctggtatg ggtggagcta tggatttagt aaatggagct    420
aagaaagtaa taattgcaat gagacataca aataaaggtc aacctaaaat tttaaaaaaa    480
tgtacacttc ccctcacggc aaagtctcaa gcaaatctaa ttgtaacaga acttggagta    540
attgaggtta ttaatgatgg tttacttctc actgaaatta ataaaaacac aaccattgat    600
gaaataaggt ctttaactgc tgcagattta ctcatatcca atgaacttag acccatggct    660
gtttag                                                              666
```

<210> SEQ ID NO 99
<211> LENGTH: 35
<212> TYPE: DNA
<213> ORGANISM: artificial
<220> FEATURE:
<223> OTHER INFORMATION: primer

<400> SEQUENCE: 99

```
aaggagattc caatgagaga tgtagtaata gtaag                               35
```

<210> SEQ ID NO 100
<211> LENGTH: 33
<212> TYPE: DNA
<213> ORGANISM: artificial
<220> FEATURE:
<223> OTHER INFORMATION: primer

<400> SEQUENCE: 100

```
ttagtctctt tcaactacga gagctgttcc ctg                                 33
```

<210> SEQ ID NO 101
<211> LENGTH: 34
<212> TYPE: DNA
<213> ORGANISM: artificial
<220> FEATURE:

<223> OTHER INFORMATION: primer

<400> SEQUENCE: 101
aaggagattc caatgaaaaa ggtatgtgtt atag                              34

<210> SEQ ID NO 102
<211> LENGTH: 32
<212> TYPE: DNA
<213> ORGANISM: artificial
<220> FEATURE:
<223> OTHER INFORMATION: primer

<400> SEQUENCE: 102
ttattttgaa taatcgtaga aacctttttcc tg                                32

<210> SEQ ID NO 103
<211> LENGTH: 37
<212> TYPE: DNA
<213> ORGANISM: artificial
<220> FEATURE:
<223> OTHER INFORMATION: primer

<400> SEQUENCE: 103
aaggagattc caatgtcaaa agagatttat gaatcag                           37

<210> SEQ ID NO 104
<211> LENGTH: 33
<212> TYPE: DNA
<213> ORGANISM: artificial
<220> FEATURE:
<223> OTHER INFORMATION: primer

<400> SEQUENCE: 104
ctacaatttt tttaccaaat tcaaaaacat tcc                               33

<210> SEQ ID NO 105
<211> LENGTH: 34
<212> TYPE: DNA
<213> ORGANISM: artificial
<220> FEATURE:
<223> OTHER INFORMATION: primer

<400> SEQUENCE: 105
aaggagattc caatggattt taatttaaca agag                              34

<210> SEQ ID NO 106
<211> LENGTH: 42
<212> TYPE: DNA
<213> ORGANISM: artificial
<220> FEATURE:
<223> OTHER INFORMATION: primer

<400> SEQUENCE: 106
ttatctaaaa attttcctga ataactaat tttctgaact tc                      42

<210> SEQ ID NO 107
<211> LENGTH: 37
<212> TYPE: DNA
<213> ORGANISM: artificial
<220> FEATURE:
<223> OTHER INFORMATION: primer

<400> SEQUENCE: 107
aaggagattc caatgctaag ttttgattat tcaatac                           37

```
<210> SEQ ID NO 108
<211> LENGTH: 39
<212> TYPE: DNA
<213> ORGANISM: artificial
<220> FEATURE:
<223> OTHER INFORMATION: primer

<400> SEQUENCE: 108
ttaatatgat tttttaaata tctcaagaag catcctctg                              39

<210> SEQ ID NO 109
<211> LENGTH: 35
<212> TYPE: DNA
<213> ORGANISM: artificial
<220> FEATURE:
<223> OTHER INFORMATION: primer

<400> SEQUENCE: 109
aaggagacta ctatgtctga gaaacaattt ggggc                                  35

<210> SEQ ID NO 110
<211> LENGTH: 22
<212> TYPE: DNA
<213> ORGANISM: artificial
<220> FEATURE:
<223> OTHER INFORMATION: primer

<400> SEQUENCE: 110
tcagtaaaat tcttctggca at                                                22

<210> SEQ ID NO 111
<211> LENGTH: 38
<212> TYPE: DNA
<213> ORGANISM: artificial
<220> FEATURE:
<223> OTHER INFORMATION: primer

<400> SEQUENCE: 111
aaggagacta ctatgtcaga aatcacacaa cttttttca                              38

<210> SEQ ID NO 112
<211> LENGTH: 33
<212> TYPE: DNA
<213> ORGANISM: artificial
<220> FEATURE:
<223> OTHER INFORMATION: primer

<400> SEQUENCE: 112
tcattcagct acatcaatat cttttttcaa agc                                    33

<210> SEQ ID NO 113
<211> LENGTH: 38
<212> TYPE: DNA
<213> ORGANISM: artificial
<220> FEATURE:
<223> OTHER INFORMATION: primer

<400> SEQUENCE: 113
aaggagacta ctatgtctaa agttgcagca gttactgg                               38

<210> SEQ ID NO 114
<211> LENGTH: 24
<212> TYPE: DNA
<213> ORGANISM: artificial
<220> FEATURE:
<223> OTHER INFORMATION: primer
```

<400> SEQUENCE: 114
ttaatgaaat tgcattccac catc                                      24

<210> SEQ ID NO 115
<211> LENGTH: 33
<212> TYPE: DNA
<213> ORGANISM: artificial
<220> FEATURE:
<223> OTHER INFORMATION: primer

<400> SEQUENCE: 115
aaggagacta ctgtggcttg gtgtggaatc tgt                            33

<210> SEQ ID NO 116
<211> LENGTH: 23
<212> TYPE: DNA
<213> ORGANISM: artificial
<220> FEATURE:
<223> OTHER INFORMATION: primer

<400> SEQUENCE: 116
ttatagacct tttccagttg gtg                                       23

<210> SEQ ID NO 117
<211> LENGTH: 37
<212> TYPE: DNA
<213> ORGANISM: artificial
<220> FEATURE:
<223> OTHER INFORMATION: primer

<400> SEQUENCE: 117
aaggagacta ctatgaaaag atcaaaacga tttgcag                        37

<210> SEQ ID NO 118
<211> LENGTH: 21
<212> TYPE: DNA
<213> ORGANISM: artificial
<220> FEATURE:
<223> OTHER INFORMATION: primer

<400> SEQUENCE: 118
tcagaatgcc tggcggaaaa t                                         21

<210> SEQ ID NO 119
<211> LENGTH: 40
<212> TYPE: DNA
<213> ORGANISM: artificial
<220> FEATURE:
<223> OTHER INFORMATION: primer

<400> SEQUENCE: 119
aaggagacta ctatgagcta tcgtatgttt gattatctgg                     40

<210> SEQ ID NO 120
<211> LENGTH: 21
<212> TYPE: DNA
<213> ORGANISM: artificial
<220> FEATURE:
<223> OTHER INFORMATION: primer

<400> SEQUENCE: 120
tcagaatgcc tggcggaaaa t                                         21

<210> SEQ ID NO 121
<211> LENGTH: 35

```
<212> TYPE: DNA
<213> ORGANISM: artificial
<220> FEATURE:
<223> OTHER INFORMATION: primer

<400> SEQUENCE: 121
aaggagattc caatgagaga tgtagtaata gtaag                              35

<210> SEQ ID NO 122
<211> LENGTH: 33
<212> TYPE: DNA
<213> ORGANISM: artificial
<220> FEATURE:
<223> OTHER INFORMATION: primer

<400> SEQUENCE: 122
ttagtctctt tcaactacga gagctgttcc ctg                                33

<210> SEQ ID NO 123
<211> LENGTH: 32
<212> TYPE: DNA
<213> ORGANISM: artificial
<220> FEATURE:
<223> OTHER INFORMATION: primer

<400> SEQUENCE: 123
aaggaggcgg cgatgaactc taaaataatt ag                                 32

<210> SEQ ID NO 124
<211> LENGTH: 26
<212> TYPE: DNA
<213> ORGANISM: artificial
<220> FEATURE:
<223> OTHER INFORMATION: primer

<400> SEQUENCE: 124
ttatgcaggc tcctttacta tataat                                       26

<210> SEQ ID NO 125
<211> LENGTH: 30
<212> TYPE: DNA
<213> ORGANISM: artificial
<220> FEATURE:
<223> OTHER INFORMATION: primer

<400> SEQUENCE: 125
aaggaggcgg cgatgttaaa ggatgaagta                                   30

<210> SEQ ID NO 126
<211> LENGTH: 33
<212> TYPE: DNA
<213> ORGANISM: artificial
<220> FEATURE:
<223> OTHER INFORMATION: primer

<400> SEQUENCE: 126
cccttactta agataatcat atataacttc agc                                33

<210> SEQ ID NO 127
<211> LENGTH: 35
<212> TYPE: DNA
<213> ORGANISM: artificial
<220> FEATURE:
<223> OTHER INFORMATION: primer

<400> SEQUENCE: 127
```

-continued

```
aaggagattc caatgagaga tgtagtaata gtaag                              35

<210> SEQ ID NO 128
<211> LENGTH: 33
<212> TYPE: DNA
<213> ORGANISM: artificial
<220> FEATURE:
<223> OTHER INFORMATION: primer

<400> SEQUENCE: 128
ttagtctctt tcaactacga gagctgttcc ctg                                33

<210> SEQ ID NO 129
<211> LENGTH: 32
<212> TYPE: DNA
<213> ORGANISM: artificial
<220> FEATURE:
<223> OTHER INFORMATION: primer

<400> SEQUENCE: 129
aaggaggcgg cgatgaactc taaaataatt ag                                 32

<210> SEQ ID NO 130
<211> LENGTH: 26
<212> TYPE: DNA
<213> ORGANISM: artificial
<220> FEATURE:
<223> OTHER INFORMATION: primer

<400> SEQUENCE: 130
ttatgcaggc tcctttacta tataat                                       26

<210> SEQ ID NO 131
<211> LENGTH: 30
<212> TYPE: DNA
<213> ORGANISM: artificial
<220> FEATURE:
<223> OTHER INFORMATION: primer

<400> SEQUENCE: 131
aaggaggcgg cgatgttaaa ggatgaagta                                   30

<210> SEQ ID NO 132
<211> LENGTH: 33
<212> TYPE: DNA
<213> ORGANISM: artificial
<220> FEATURE:
<223> OTHER INFORMATION: primer

<400> SEQUENCE: 132
cccttactta agataatcat atataacttc agc                               33

<210> SEQ ID NO 133
<211> LENGTH: 32
<212> TYPE: DNA
<213> ORGANISM: artificial
<220> FEATURE:
<223> OTHER INFORMATION: primer

<400> SEQUENCE: 133
aaggagaatt ccaatgcata cctttttctct gc                               32

<210> SEQ ID NO 134
<211> LENGTH: 25
<212> TYPE: DNA
<213> ORGANISM: artificial
```

```
<220> FEATURE:
<223> OTHER INFORMATION: primer

<400> SEQUENCE: 134
tcattgcagg ttctccagca gttgc                                   25

<210> SEQ ID NO 135
<211> LENGTH: 31
<212> TYPE: DNA
<213> ORGANISM: Artificial
<220> FEATURE:
<223> OTHER INFORMATION: Primer

<400> SEQUENCE: 135
taaagtcgac aaggagacta gcatgaccaa c                            31
```